(12) United States Patent
Campana et al.

(10) Patent No.: US 12,129,485 B2
(45) Date of Patent: Oct. 29, 2024

(54) BLOCKADE OF CD2 SURFACE EXPRESSION AND EXPRESSION OF CHIMERIC ANTIGEN RECEPTORS FOR IMMUNOTHERAPY OF T-CELL MALIGNANCIES

(71) Applicant: National University of Singapore, Singapore (SG)

(72) Inventors: Dario Campana, Singapore (SG); Natasha Vinanica, Singapore (SG); Yi Tian Png, Singapore (SG); Takahiro Kamiya, Tokyo (JP)

(73) Assignee: National University of Singapore, Singapore (SG)

( * ) Notice: Subject to any disclaimer, the term of this patent is extended or adjusted under 35 U.S.C. 154(b) by 977 days.

(21) Appl. No.: 17/057,973

(22) PCT Filed: May 23, 2019

(86) PCT No.: PCT/US2019/033836
§ 371 (c)(1),
(2) Date: Nov. 23, 2020

(87) PCT Pub. No.: WO2019/226945
PCT Pub. Date: Nov. 28, 2019

(65) Prior Publication Data
US 2021/0214684 A1 Jul. 15, 2021

Related U.S. Application Data

(60) Provisional application No. 62/675,511, filed on May 23, 2018.

(51) Int. Cl.
| A61K 48/00 | (2006.01) |
| A61K 35/17 | (2015.01) |
| C07H 21/04 | (2006.01) |
| C07K 14/705 | (2006.01) |
| C07K 14/725 | (2006.01) |
| C07K 16/28 | (2006.01) |
| C12N 5/0783 | (2010.01) |
| C12N 15/63 | (2006.01) |
| A01K 67/00 | (2006.01) |

(52) U.S. Cl.
CPC ............ *C12N 5/0636* (2013.01); *A61K 35/17* (2013.01); *C07K 14/70507* (2013.01); *C07K 14/7051* (2013.01); *C07K 14/70578* (2013.01); *C07K 16/2806* (2013.01); *C12N 5/0646* (2013.01); *C07K 2317/622* (2013.01); *C07K 2319/03* (2013.01); *C07K 2319/04* (2013.01); *C12N 2510/00* (2013.01)

(58) Field of Classification Search
CPC .......... C12N 5/0636; C12N 5/0646; C12N 2510/00; C07K 14/70507; C07K 14/7051; C07K 2317/622; C07K 2319/03; C07K 2319/04
See application file for complete search history.

(56) References Cited

U.S. PATENT DOCUMENTS

| 4,683,195 A | 7/1987 | Mullis et al. |
| 4,946,778 A | 8/1990 | Ladner et al. |
| 5,260,203 A | 11/1993 | Ladner et al. |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,054,297 A | 4/2000 | Carter et al. |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,407,213 B1 | 6/2002 | Carter et al. |
| 6,410,248 B1 | 6/2002 | Greisman et al. |
| 6,453,242 B1 | 9/2002 | Eisenberg et al. |
| 6,534,261 B1 | 3/2003 | Cox, III et al. |
| 6,719,971 B1 | 4/2004 | Carter et al. |
| 6,979,446 B2 * | 12/2005 | Patti et al. |
| 7,557,189 B2 * | 7/2009 | Hoffee et al. |
| 7,887,805 B2 | 2/2011 | Pedersen et al. |
| 8,119,775 B2 | 2/2012 | Moretta et al. |
| 8,399,645 B2 | 3/2013 | Campana et al. |
| 8,580,714 B2 | 11/2013 | Almagro et al. |
| 8,614,307 B2 | 12/2013 | Moretta et al. |
| 8,637,258 B2 | 1/2014 | Padkjaer et al. |

(Continued)

FOREIGN PATENT DOCUMENTS

| CA | 2937157 A1 | 1/2018 |
| CN | 107709548 A | 2/2018 |

(Continued)

OTHER PUBLICATIONS

Xiao et al. Efficient long-term gene transfer into muscle tissue of immunocompetent mice by adeno-associated virus vector. J. Virology 70:8098-8108, (Year: 1996).*

Connelly et al. Mitogenic properties of a bispecific single-chain Fv—Ig fusion generated from CD2-specific mAb to distinct epitopes. International Immunology 10:1863-1872, (Year: 1998).*

EP22180254.9 Extended European Search Report dated Jan. 16, 2023.

(Continued)

*Primary Examiner* — Quang Nguyen

(74) *Attorney, Agent, or Firm* — Hamilton, Brook, Smith & Reynolds, P.C.

(57) ABSTRACT

The present invention provides engineered immune cells comprising an anti-CD2 protein expression blocker (PEBL) and an anti-CD2 chimeric antigen receptor (CAR). In some embodiments, such engineered immune cells lack surface expression CD2. Also, provided herein are methods of using such cells in cancer therapies.

10 Claims, 8 Drawing Sheets
Specification includes a Sequence Listing.

(56) References Cited

U.S. PATENT DOCUMENTS

| | | | |
|---|---|---|---|
| 8,697,359 B1 | 4/2014 | Zhang | |
| 8,735,153 B2 | 5/2014 | Wolffe et al. | |
| 8,771,945 B1 | 7/2014 | Zhang | |
| 8,796,427 B2 | 8/2014 | Spee et al. | |
| 8,841,418 B2* | 9/2014 | Karsunky et al. | |
| 8,981,065 B2 | 3/2015 | Moretta et al. | |
| 9,422,368 B2 | 8/2016 | Spee et al. | |
| 9,683,042 B2 | 6/2017 | Lee et al. | |
| 9,855,298 B2 | 1/2018 | Bot et al. | |
| 9,902,936 B2 | 2/2018 | Moretta et al. | |
| 10,273,280 B2* | 4/2019 | Ma et al. | |
| 10,730,942 B2* | 8/2020 | Pule et al. | |
| 10,751,416 B2* | 8/2020 | Gilliet et al. | |
| 10,765,699 B2 | 9/2020 | Campana et al. | |
| 11,648,269 B2 | 5/2023 | Campana et al. | |
| 11,679,132 B2 | 6/2023 | Campana et al. | |
| 2005/0064474 A1 | 3/2005 | Urnov et al. | |
| 2006/0034834 A1 | 2/2006 | Marasco et al. | |
| 2006/0188987 A1 | 8/2006 | Guschin et al. | |
| 2007/0036773 A1 | 2/2007 | Cooper et al. | |
| 2009/0196850 A1 | 8/2009 | Romagne et al. | |
| 2012/0282256 A1 | 11/2012 | Campana et al. | |
| 2013/0266551 A1 | 10/2013 | Campana et al. | |
| 2013/0287748 A1 | 10/2013 | June et al. | |
| 2014/0030240 A1 | 1/2014 | Gregory et al. | |
| 2014/0068797 A1 | 3/2014 | Doudna et al. | |
| 2014/0120622 A1 | 5/2014 | Gregory et al. | |
| 2014/0186387 A1 | 7/2014 | Lauer et al. | |
| 2016/0120906 A1 | 5/2016 | Galetto et al. | |
| 2016/0256488 A1 | 9/2016 | Wu | |
| 2016/0272999 A1 | 9/2016 | Duchateau et al. | |
| 2016/0312182 A1 | 10/2016 | Sentman | |
| 2017/0037369 A1 | 2/2017 | Ramsborg et al. | |
| 2017/0119820 A1 | 5/2017 | Moriarity et al. | |
| 2017/0204372 A1 | 7/2017 | Mohler et al. | |
| 2018/0008638 A1 | 1/2018 | Campana et al. | |
| 2018/0086831 A1 | 3/2018 | Pule et al. | |
| 2019/0046571 A1 | 2/2019 | Campana et al. | |
| 2019/0062706 A1 | 2/2019 | Almaasbak et al. | |
| 2019/0136186 A1 | 5/2019 | Germeroth et al. | |
| 2021/0046112 A1 | 2/2021 | Campana et al. | |
| 2021/0214439 A1 | 7/2021 | Campana | |
| 2022/0347219 A1 | 11/2022 | Campana et al. | |
| 2022/0370501 A1 | 11/2022 | Campana et al. | |

FOREIGN PATENT DOCUMENTS

| | | |
|---|---|---|
| CN | 107921148 A | 4/2018 |
| EP | 0404097 A2 | 12/1990 |
| EP | 2247619 A1 | 11/2010 |
| GB | 2338237 A | 12/1999 |
| JP | H03219896 A | 9/1991 |
| JP | H09501824 A | 2/1997 |
| JP | 2008506368 A | 3/2008 |
| JP | 2008518021 A | 5/2008 |
| JP | 2009511495 A | 3/2009 |
| JP | 2010537671 A | 12/2010 |
| JP | 2011510047 A | 3/2011 |
| JP | 2014507118 A | 3/2014 |
| JP | 6895380 B2 | 6/2021 |
| WO | WO-8801649 A1 | 3/1988 |
| WO | WO-9311161 A1 | 6/1993 |
| WO | WO-9837186 A1 | 8/1998 |
| WO | WO-9853057 A1 | 11/1998 |
| WO | WO-9914353 A2 | 3/1999 |
| WO | WO-0027878 A1 | 5/2000 |
| WO | WO-0188197 A2 | 11/2001 |
| WO | WO-02077227 A2 | 10/2002 |
| WO | WO-03051926 A2 | 6/2003 |
| WO | WO-2005017163 A2 | 2/2005 |
| WO | WO-2006003179 A2 | 1/2006 |
| WO | WO-2009092805 A1 | 7/2009 |
| WO | WO-2012079000 A1 | 6/2012 |
| WO | WO-2013126712 A1 | 8/2013 |
| WO | WO-2014011984 A1 | 1/2014 |
| WO | WO-2014124143 A1 | 8/2014 |
| WO | WO-2015075468 A1 | 5/2015 |
| WO | WO-2015121454 A1 | 8/2015 |
| WO | WO-2015150771 A1 | 10/2015 |
| WO | WO-2016055551 A1 | 4/2016 |
| WO | WO-2016102965 A1 | 6/2016 |
| WO | WO-2016126213 A1 | 8/2016 |
| WO | WO-2016138491 A1 | 9/2016 |
| WO | WO 2016/183041 A2 | 11/2016 |
| WO | WO 2017/146767 A1 | 8/2017 |
| WO | WO-2017213979 A1 | 12/2017 |
| WO | WO 2018/027036 A1 | 2/2018 |
| WO | WO-2018073393 A2 | 4/2018 |
| WO | WO-2018098306 A1 | 5/2018 |
| WO | WO-2019226945 A1 | 11/2019 |
| WO | WO-2019226946 A1 | 11/2019 |

OTHER PUBLICATIONS

U.S. Appl. No. 17/862,721 Notice of Allowance dated Feb. 15, 2023.

Brown et al. Novel Treatments for Chronic Lymphocytic Leukemia and Moving Forward. American Society of Clinical Oncology Educational Book, pp. e317-e325 (2014). Retrieved at URL: https://ascopubs.org/doi/pdfdirect/10.14694/EdBook_AM.2014.34.e317.

Caruana et al. From Monoclonal Antibodies to Chimeric Antigen Receptors for the Treatment of Human Malignancies. Semin Oncol. Oct. 2014 ; 41(5): 661-666.

Certified PCT/US2016/019953 priority document U.S. Appl. No. 62/121,842, Ma, Yupo et al., inventors, filed Feb. 27, 2015.

Feng et al. Treatment of Aggressive T Cell Lymphoblastic Lymphoma/leukemia Using Anti-CD5 CAR T Cells. Stem Cell Reviews and Reports (2021) 17:652-661. Published online Jan. 6, 2021.

Fujiwara, et al. Adoptive Immunotherapy for Hematological Malignancies Using T Cells Gene-Modified to Express Tumor Antigen-Specific Receptors. Pharmaceuticals (Basel). Dec. 2014; 7(12): 1049-1068.

Glienke et al. Advantages and applications of CAR-expressing natural killer cells. Frontiers in Pharmacology, vol. 6, Article 21 (Feb. 12, 2015). 7 pages.

Guo et al. Efficiency and side effects of anti-CD38 Car T cells in an adult patient with relapsed B-ALL after failure of bi-specific CD19/CD22 CAR T cell treatment. Cell Mol Immunol 17, 430-432 (2020).

Hishima et al. CD5 Expression in Thymic Carcinoma. American Journal of Pathology, vol. 145, No. 2, pp. 268-275 (Aug. 1994).

Imboden et al. Stimulation of CD5 enhances signal transduction by the T cell antigen receptor. J Clin Invest. 1990. 85:130-134.

Jena et al., Redirecting T-cell specificity by introducing a tumor-specific chimeric antigen receptor. Blood. 116:1035-1044 (2010).

Kapp et al. Chapter 1: Post-Targeting Functions of Signal Peptides. In Protein Transport into the Endoplasmic Reticulum, Zimmerman, ed., 2009, Landes Bioscience. 13 pages. Retrieved at URL: https://www.ncbi.nlm.nih.gov/books/NBK6322/.

Lemaistre et al. Phase I Trial of H65-RTA Immunoconjugate in Patients With Cutaneous T-cell Lymphoma. Blood, vol. 78, No. 5 (Sep. 1), 1991: pp. 1173-1182.

Lewis et al. The immunophenotype of pre-TALL/LBL revisited. Experimental and Molecular Pathology 81 (2006) 162-165. Available online Aug. 14, 2006.

Li et al. Flow Cytometry in the Differential Diagnosis of Lymphocyte-Rich Thymoma From Precursor T-Cell Acute Lymphoblastic Leukemia/Lymphoblastic Lymphoma. Am J Clin Pathol 2004;121:268-274.

Litzow et al. How I treat T-cell acute lymphoblastic leukemia in adults. Blood. 2015; 126(7):833-841. Retrieved at URL: https://www.academia.edu/download/47911039/j.yexmp.2006.06.00620160809-3503-eb5sgz.pdf.

Liu et al. Critical Role of CD2 Co-stimulation in Adaptive Natural Killer Cell Responses Revealed in NKG2C-Deficient Humans. Cell Reports 15, 1088-1099 (May 3, 2016).

Liu et al. [NK cell surface receptors and their research progress—review]. Zhongguo shi yan xue ye xue za zhi. Aug. 2012;20(4):1034-1038. English abstract only. Retrieved at URL: https://pubmed.ncbi.nlm.nih.gov/22931679/. One page.

(56) References Cited

OTHER PUBLICATIONS

McNerney et al. The CD2 family of natural killer cell receptors. Curr Top Microbiol Immunol. 2006;298:91-120. Abstract only.
Morris et al. Antibody-based therapy of leukaemia. Expert Rev Mol Med. Sep. 30, 2009; 11: e29.
Pinz et al. Preclinical targeting of human T cell malignancies using CD4-specific chimeric antigen receptor (CAR)-engineered T cells. Leukemia, accepted article preview (Nov. 3, 2015). Retrieved at URL: https://www.researchgate.net/profile/Alexander-Jares/publication/283493430_Preclinical_targeting_of_human_T_cell_malignancies_using_CD4-specific_chimeric_antigen_receptor_CAR-engineered_T_cells/links/5643662808aef646e6c6a549/Preclinical-targeting-of-human-T-cell-malignancies-using-CD4-specific-chimeric-antigen-receptor-CAR-engineered-T-cells.pdf. 30 pages.
Rezvani et al. The Application of Natural Killer Cell immunotherapy for the Treatment of Cancer. Frontiers in Immunology, vol. 6, Article 578 (Nov. 17, 2015). 13 pages.
Roitt et al. Roitt's Essential Immunology. 12th Edition, Wiley-Blackwell, Chapter 4 (2012).
Sommermeyer, et al., Chimeric antigen receptor-modified T cells derived from defined CD8+ and CD4+ subsets confer superior antitumor reactivity in vivo. Leukemia 30(2):492-500 (2016).
Zhong-Fu et al. Clinical Applications of NK Cells in Tumor Immunotherapy. Chinese Journal of Biochemistry and Molecular Biology 27(12):1088-1093 (Dec. 2011). With English translation.
Almagro, Juan C., Fransson, Johan. Humanization of antibodies. Frontiers in Bioscience 13;1619-1633 (Jan. 1, 2008).
Altschul et al. Basic local alignment search tool. J Mol Biol 215(3):403-410 (1990).
Anti-CD3 epsilon [OKT-3 (muromonab)]. Absolute Antibody. Website. Copyright 2021. Retrieved Dec. 26, 2021 at URL: https://absoluteantibody.com/product/anti-cd3-epsilon-okt-3- . . . 4 pages.
Anti-CD3D monoclonal antibody, clone PLU4 (DCABH-10124). Product Information. CD Creative Diagnostics. Publication date unknown. 2 pages.
Anti-TCR [BMA031]. Absolute Antibody. Website. Copyright 2021. Retrieved Dec. 26, 2021 at URL: https://absoluteantibody.com/product/anti-tcr-bma031/ 4 pages.
Appelbaum. Haematopoietic cell transplantation as immunotherapy. Nature, vol. 411, pp. 385-389 (2001).
Arafat et al. Antineoplastic effect of anti-erbB-2 intrabody is not correlated with scFv affinity for its target. Cancer Gene Therapy, vol. 7, No. 9, 2000: pp. 1250-1256.
Arase et al. Recognition of virus infected cells by NK cells (w/ English abstract). Department of Immunochemistry, Research Institute for Microbial Diseases, Osaka University, vol. 54, No. 2, pp. 153-160 (2004).
Beerli, et al. Engineering polydactyl zinc-finger transcription factors. Nat Biotechnol. Feb. 2002;20(2):135-141. doi: 10.1038/nbt0202-135.
Boldicke et al., Blocking translocation of cell surface molecules from the ER to the cell surface by intracellular antibodies targeted to the ER, J. Cell. Mol. Med., 11(1):54-70 (2007).
Brentjens et al. CD19-targeted T cells rapidly induce molecular remissions in adults with chemotherapy-refractory acute lymphoblastic leukemia. Sci Transl Med. Mar. 20, 2013;5(177):177ra38. 9 pages.
Brentjens et al. Eradication of systemic B-cell tumors by genetically targeted human T lymphocytes co-stimulated by CD80 and interleukin-15. Nat Med. Mar. 2003;9(3):279-86.
Brentjens et al. Safety and persistence of adoptively transferred autologous CD19-targeted T cells in patients with relapsed or chemotherapy refractory B-cell leukemias. Blood. Nov. 3, 2011;118(18):4817-28. Prepublished online Aug. 17, 2011.
Campana et al. 4-1BB chimeric antigen receptors. Cancer J. Mar.-Apr. 2014;20(2):134-40.
Chang et al. A chimeric receptor with NKG2D specificity enhances natural killer cell activation and killing of tumor cells. Cancer Res 73(6):1777-86 (Mar. 15, 2013). Published online Jan. 9, 2013.

Choo, et al. Advances in zinc finger engineering. Curr Opin Struct Biol. Aug. 2000;10(4):411-416. doi: 10.1016/s0959-440x(00)00107-x.
Chothia et al.: Canonical Structures for the Hypervariable Regions of Immunoglobulins. J. Mod. Biol. 196:901-917 (1987).
Clift, Dean, et al "A Method for the Acute and Rapid Degradation of Endogenous Proteins", Elsevier Inc., Cell 172, Dec. 14, 2017, pp. 1692-1706.
Cooley et al. Donor selection for natural killer cell receptor genes leads to superior survival after unrelated transplantation for acute myelogenous leukemia. Blood (2010) 116 (14): 2411-2419.
Cooper, et al. T-cell clones can be rendered specific for CD19: toward the selective augmentation of the graft-versus-B-lineage leukemia effect. Blood. Feb. 15, 2003;101(4):1637-44. Epub Oct. 10, 2002.
Critchlow et al. DNA end-joining: from yeast to man. Trends in Biochemical Sciences, Oct. 1998, pp. 394-398.
Davila. Efficacy and toxicity management of 19-28z CAR T cell therapy in B cell acute lymphoblastic leukemia. Sci Transl Med 6(224):224ra25 (2014).
Dotti et al. Design and Development of Therapies using Chimeric Antigen Receptor-Expressing T cells. Immunol Rev. 257(1):35 pgs (2014).
Dudley et al. Adoptive cell therapy for patients with metastatic melanoma: evaluation of intensive myeloablative chemoradiation preparative regimens. J Clin Oncol 26(32):5233-5239 (2008).
Dudley et al. Adoptive Cell Transfer Therapy Following Non-Myeloablative but Lymphodepleting Chemotherapy for the Treatment of Patients With Refractory Metastatic Melanoma. J Clin Oncol. 23(10):2346-2357 (2005).
EP16746922.0 Extended European Search Report dated Sep. 21, 2018.
EP19806621.9 Extended European Search Report dated Jan. 5, 2022.
EP19808214.1 Extended European Search Report dated Jan. 7, 2022.
Eshhar et al. Specific activation and targeting of cytotoxic lymphocytes through chimeric single chains consisting of antibody-binding domains and the gamma or zeta subunits of the immunoglobulin and T-cell receptors. Proc Natl Acad Sci U S A, vol. 90, pp. 720-724 (Jan. 1993).
Gaj, et al. ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gao et al. Retention mechanisms for ER and Golgi membrane proteins. Trends in Plant Science, vol. 19, Issue 8, pp. 508-515 (Aug. 2014).
Gassner et al. Fludarabine modulates composition and function of the T cell pool in patients with chronic lymphocytic leukaemia. Cancer Immunol Immunother (2011) 60:75-85. Published online Sep. 21, 2010.
Geiger et al. Integrated src kinase and costimulatory activity enhances signal transduction through single-chain chimeric receptors in T lymphocytes. Blood 98(8):2364-2371 (2001).
Geiger et al. The TCR zeta-chain immunoreceptor tyrosine-based activation motifs are sufficient for the activation and differentiation of primary T lymphocytes. The Journal of Immunology, 1999, 162: 5931-5939.
Giebel et al. Survival advantage with KIR ligand incompatibility in hematopoietic stem cell transplantation from unrelated donors. Blood (2003) 102 (3): 814-819.
Grimshaw, B.D. et al., BGST Abstract Mar. 9, 2012, abstract P023, "Creating a 'null' T cell for use in adoptive immunotherapy", British Society for Gene and Cell Therapy 2012, hltp://www.bsqct.orq, Human Gene Therapy, 22 pages.
Grimshaw. Developing a universal T cell for use in adoptive immunotherapy (thesis), University College London (2015). Retrieved Aug. 22, 2022 at URL: http://discovery.ucl.ac.uk/1470207/1/Grimshaw%20Ben%20Thesis.pdf. 267 pages.
Grimshaw et al. Creating a Null T Cell for Adoptive Immunotherapy. Poster. Mar. 9, 2012. One page.

(56) References Cited

OTHER PUBLICATIONS

Grovender et al. Single-chain antibody fragment-based adsorbent for the extracorporeal removal of β2-microglobulin. Kidney International, vol. 65 (2004), pp. 310-322.

Grupp et al. Chimeric Antigen Receptor-Modified T Cellsfor Acute Lymphoid Leukemia. N Engl J Med 368; 16, pp. 1509-1508 (Apr. 18, 2013). With correction published N. Engl J. Med (2016) 374(10) 998.

Haynes et al. Rejection of syngeneic colon carcinoma by CTLs expressing single-chain antibody receptors codelivering CD28 costimulation. J Immunol 2002; 169:5780-5786.

Haynes et al. Single-chain antigen recognition receptors that costimulate potent rejection of established experimental tumors. Blood. Nov. 1, 2002;100(9):3155-63. Published online Jul. 5, 2002.

Hegde, M. et al., "Combinational targeting offsets antigen escape and enhances effector functions of adoptively transferred T cells in glioblastoma", Molecular Therapy, 2013, vol. 21, pp. 2087-2101.

Hegde, M. et al., Supplementary Material for "Combinational targeting offsets antigen escape and enhances effector functions of adoptively transferred T cells in glioblastoma", Molecular Therapy, 2013, vol. 21, pp. 2087-2101. Retrieved Jan. 6, 2022 from URL: https://ars.els-cdn.com/content/image/1-s2.0-S1525001616309315-mmc1.pdf. 9 pages.

Henikoff, et al. Amino acid substitution matrices from protein blocks. Proc Natl Acad Sci U S A. Nov. 15, 1992;89(22):10915-9.

Hermans et al. The VITAL assay: a versatile fluorometric technique for assessing CTL- and NKT-mediated cytotoxicity against multiple targets in vitro and in vivo. Journal of Immunological Methods 285 (2004) 25-40.

Holliger et al. "Diabodies": small bivalent and bispecific antibody fragments. Proc Natl Acad Sci USA, vol. 90, pp. 6444-6448 (Jul. 1993).

Hombach et al. Tumor-Specific T Cell Activation by Recombinant Immunoreceptors: CD32 Signaling and CD28 Costimulation Are Simultaneously Required for Efficient IL-2 Secretion and Can Be Integrated Into One Combined CD28/CD3ζ Signaling Receptor Molecule. J Immunol 2001; 167:6123-6131.

Imai et al. Chimeric receptors with 4-1BB signaling capacity provoke potent cytotoxicity against acute lymphoblastic leukemia. Leukemia (2004) 18, 676-684.

Imai et al. Genetic modification of primary natural killer cells overcomes inhibitory signals and induces specific killing of leukemic cells. Blood (2005) 106 (1): 376-383.

Imamura. M. et al., "Autonomous growth and increased cytotoxicity of natural killer cells expressing membrane-bound interleukin-15", Blood, 2014, vol. 124, pp. 1081-1088.

Imamura. M. et al., Supplementary Material for "Autonomous growth and increased cytotoxicity of natural killer cells expressing membrane-bound interleukin-15", Blood, 2014, vol. 124, pp. 1081-1088. Retrieved Jan. 6, 2021 at URL: https://ash.silverchair-cdn.com/ash/content_public/journal/blood/124/7/10.1182_blood-2014-02-556837/4/blood-2014-02-556837-1.pdf?Expires=1644340511&Signature=uyyKt0KS8WtXpVUILTgok2RyynmzBJgE2vCNIDD4xdwCv13vsg0goCLOpQLU~KVPtlTvlHtmCLeX2MhA7mcxzXy~ydDqrj6rHeZEBNohY4NOkmjpH9529c9SCChMFB1n80TH-cM-MgQfrETegs40K6vjiveJODaZP6TfW1gGK~5JUAn5LesZfPv9W28NmBfMoAOMVeX4Pz54V~9dWaBcCfXCR7vOrx1N8cpbxmlAumSziwKqxNCy79dwOL6ddz3joiyKtMiGNuY1c61lf6b~MwbLxZ3jK16EE-giQZhSxfLm2ctwuCbOMj8RIHCM4cO5a2zIKMAM6dut-dafGbQaRQ_&Key-Pair-Id=APKAIE5G5CRDK6RD3PGA. 11 pages.

Isalan, et al. A rapid, generally applicable method to engineer zinc fingers illustrated by targeting the HIV-1 promoter. Nat Biotechnol. Jul. 2001;19(7):656-660. doi: 10.1038/90264.

Joshi et al. Fusion to a highly charged proteasomal retargeting sequence increases soluble cytoplasmic expression and efficacy of diverse anti-synuclein intrabodies. mAbs, vol. 4, Issue 6, pp. 686-693 (2012). Published online: Aug. 28, 2012.

Kalos, et al., "T Cells with Chimeric Antigen Receptors Have Potent Antitumor Effects and Can Establish Memory in Patients with Advanced Leukemia", Science Translation Medicine 3.95 (2011):95ra73-95ra73.

Kamiya, et al., "A novel method to generate T-cell receptor-deficient antigen receptor T cells," Blood Advances, vol. 2, No. 5, Mar. 13, 2018, pp. 517-528.

Kamiya et al. Blocking expression of inhibitory receptor NKG2A overcomes tumor resistance to NK cells. J Clin Invest. 2019; 129(5):2094-2106.

Kamoun et al. Identification of a human T lymphocyte surface protein associated with the E-rosette receptor. J Exp Med, vol. 153, pp. 207-212 (Jan. 1981).

Kloss, C.C. et al., Supplementary Text and Figures for "Combinatorial antigen recognition with balanced signaling promotes selective tumor eradication by engineered T cells", Nature Biotechnology, 2013, vol. 31, pp. 71-75. Retrieved Jan. 6, 2021 at URL: https://static-content.springer.com/esm/art%3A10.1038%2Fnbt.2459/MediaObjects/41587_2013_BFnbt2459_MOESM2_ESM.pdf. 5 pages.

Kloss. Combinatorial antigen recognition with balanced signaling promotes selective tumor eradication by engineered T cells. Nature Technology, vol. 31, No. 1, pp. 71-75 (Jan. 2013). Published online Dec. 16, 2012.

Kochenderfer et al: B-cell depletion and remissions of malignancy along with cytokine- associated toxicity in a clinical trial of anti-CD19 chimeric-antigen-receptor-transduced T cells. Blood 119(12):2709-2720 doi:10.1182/blood-2011-10-384388 (2012). Published online Dec. 8, 2011.

Kochenderfer JN, Feldman SA, Zhao Y, Xu H, Black MA, Morgan RA, Wilson WH, Rosenberg SA. 2009. Construction and preclinical evaluation of an anti-CD19 chimeric antigen receptor. Journal of Immunotherapy 32:689-702.

Kolb et al. Graft-versus-leukemia effect of donor lymphocyte transfusions in marrow grafted patients. Blood, vol. 86. No. 5 (Sep. 1), 1995: pp. 2041-2050.

Kudo et al. T lymphocytes expressing a CD16 signaling receptor exert antibody-dependent cancer cell killing. Cancer Res 74(1):93-103 (2013).

Kyriakidis et al. Invasive Fungal Diseases in Children with Hematological Malignancies Treated with Therapies That Target Cell Surface Antigens: Monoclonal Antibodies, Immune Checkpoint Inhibitors and CAR T-Cell Therapies. J. Fungi 2021, 7, 186. Retrieved Jan. 7, 2022 at URL: https://www.mdpi.com/2309-608X/7/3/186/pdf. 30 pages.

Lanitis et al. Chimeric antigen receptor T Cells with dissociated signaling domains exhibit focused anti-tumor activity with reduced potential for toxicity in vivo. Cancer Immunol Res 1(1):43-53 (2013).

Lee, et al. Current concepts in the diagnosis and management of cytokine release syndrome. Blood. Jul. 10, 2014;124(2):188-95. doi: 10.1182/blood-2014-05-552729. Epub May 29, 2014.

Lo et al. Harnessing the tumour-derived cytokine, CSF-1, to costimulate T-cell growth and activation. Molecular Immunology 45 (2008) 1276-1287. Available online Oct. 24, 2007.

Ma et al. Yeast Mre11 and Rad1 Proteins Define a Ku-Independent Mechanism to Repair Double-Strand Breaks Lacking Overlapping End Sequences. Molecular and Cellular Biology, vol. 23, No. 23, pp. 8820-8828 (Dec. 2003).

Maciocia et al. A simple protein-based method for generation of 'off the shelf' allogeneic chimeric antigen receptor T-cells. Database Embase [Online] 1-15, Elsevier Science Publishers, Amsterdam, NL (May 1, 2018). Abstract. XP002784541. Database Accession No. EMB-623339718.

Maciocia et al. A simple protein-based method for generation of 'off the shelf' allogeneic chimeric antigen receptor T-cells. Molecular Therapy, vol. 26, No. 5, Supplement 1, pp. 296-297 (May 2018). Cell Press NLD. May 16, 2108 to May 19, 2018 Chicago, IL-297 Conf. ISSN: 1525-0024.

Maher et al. Human T-lymphocyte cytotoxicity and proliferation directed by a single chimeric TCRzeta /CD28 receptor. Nat Biotech 20(1):70-75 (2002).

(56) References Cited

OTHER PUBLICATIONS

Marschall, Andrea LJ, et al."Specific in vivo knockdown of protein function by intrabodies", Taylor & Francis Group, LLC, Nov./Dec. 2015, vol. 7, Issue 6, pp. 1010-1035.
Maude, et al., Chimeric Antigen Receptor T Cells for Sustained Remissions in Leukemia. N. Engl J. Med (2014) 371(16) 1507-1517. With correction published N. Engl J. Med 374(10):998 (2016).
Miller et al. Successful adoptive transfer and in vivo expansion of human haploidentical NK cells in patients with cancer. Blood 105:3051-3057 (2005).
Miller. Therapeutic applications: natural killer cells in the clinic. Hematology Am Soc Hematol Educ Program (2013) 2013 (1): 247-253.
Milone et al. Chimeric receptors containing CD137 signal transduction domains mediate enhanced survival of T cells and increased antileukemic efficacy in vivo. Mol. Ther. 17:1453-1464 (2009).
Muranski, et al. Increased intensity lymphodepletion and adoptive immunotherapy—how far can we go? Nat Clin Pract Oncol. Dec. 2006; 3(12): 668-681. doi: 10.1038/ncponc0666.
Needleman et al. A general method applicable to the search for similarities in the amino acid sequence of two proteins. Journal of molecular biology 48(3):443-453 (1970).
Pabo, et al. Design and selection of novel Cys2His2 zinc finger proteins. Annu Rev Biochem. 2001;70:313-340. doi: 10.1146/annurev.biochem.70.1.313.
Pardoll. The blockade of immune checkpoints in cancer immunotherapy. Nat Rev Cancer. 12(4):252-264 (2012).
PCT/SG2016/050063 International Search Report and Written Opinion dated May 9, 2016.
PCT/US2019/033836 International Search Report and Written Opinion dated Aug. 16, 2019.
PCT/US2019/033837 International Search Report and Written Opinion dated Aug. 16, 2019.
Pearson and Lipman, Improved tools for biological sequence comparison, Proc. Nat. Acad Sci USA., 85:2444-2448, (1988).
Peipp et al. A Recombinant CD7-specific Single-Chain Immunotoxin Is a Potent Inducer of Apoptosis in Acute Leukemic T Cells. Cancer Research 62, pp. 2848-2855 (May 15, 2002).
Pluckthun, "Antibodies from *Escherichia coli*," in Handbook of Experimental Pharmacology; The Pharmacology of Monoclonal Antibodies; vol. 113, Chapter 11, pp. 269-315 (1994), Rosenburg and Moore eds., Springer-Verlag, New York.
Poh. Uncovering a Culprit in CAR-T Resistance. Cancer Discov 2021;11:4. Published Online First Dec. 10, 2020. One page. Retrieved Jan. 7, 2022 at URL: https://cancerdiscovery.aacrjournals.org/content/11/1/4.2.full-text.pdf.
Porter et al., Chimeric antigen receptor-modified T cells in chronic lymphoid leukemia. N Engl J Med 365:725-733 (2011). With correction published N. Engl. J. Med (2016) 374(10) 998.
Porter et al. Induction of Graft-versus-Host Disease as Immunotherapy for Relapsed Chronic Myeloid Leukemia. N Engl J Med 1994; 330:100-106.
Reshef et al. Blockade of lymphocyte chemotaxis in visceral graft-versus-host disease. N Engl J Med 367;3 pp. 135-145 (Jul. 12, 2012).
Rossig, C. et al., "Genetic modification of T lymphocytes for adoptive immunotherapy", Molecular Therapy, 2004, vol. 10, pp. 5-18.
Rowley, J. et al., "Expression of IL-15RA or an IL-15/IL-15RA fusion on CD8+ T cells modifies adoptively transferred T-cell function in cis", European Journal of Immunology, 2009, vol. 39, pp. 491-506.
Rowley, J. et al., Supplementary Information for "Expression of IL-15RA or an IL-15/IL-15RA fusion on CD8+ T cells modifies adoptively transferred T-cell function in cis", European Journal of Immunology, 2009, vol. 39, pp. 491-506. Retrieved Jan. 6, 2022 at URL: https://onlinelibrary.wiley.com/action/downloadSupplement?doi=10.1002%2Feji.200838594&file=eji_200838594_sm_SupplInfoFig.pdf. 6 pages.
Rubnitz et al. NKAML: A Pilot Study to Determine the Safety and Feasibility of Haploidentical Natural Killer Cell Transplantation in Childhood Acute Myeloid Leukemia. J Clin Oncol. Feb. 20, 2010; 28(6): 955-959.
Rudikoff, et al. Single amino acid substitution altering antigen-binding specificity. Proc Natl Acad Sci U S A. Mar. 1982; 79(6):1979-83.
Ruggeri et al. Effectiveness of donor natural killer cell alloreactivity in mismatched hematopoietic transplants. Science 295(5562):2097-2100 (2002).
Sadelain et al. The Basic Principles of Chimeric Antigen Receptor Design. Cancer Discov. Apr. 2013 ; 3(4): 388-398.
Sanjana et al. Improved vectors and genome-wide libraries for CRISPR screening. Nat. Methods 11(8):783-784 (2014).
Sanz, L. et al., "Antibodies and gene therapy: teaching old 'magic bullets' new tricks", Trends in Immunology, 2004, vol. 25, pp. 85-91.
Sato et al. Single domain intrabodies against WASP inhibit TCR-induced immune responses in transgenic mice T cells. Sci Rep. Oct. 21, 2013;3:3003. 10 pages.
Schwartz. T cell anergy. Annu Rev Immunol. 2003;21:305-34. First published online as a Review in Advance on Dec. 5, 2002.
Score Search Results Details for U.S. Appl. No. 15/548,577 and Search Result 20190107_143513_us-15-548-577-37.rag. Search run on Jan. 7, 2019. Copy retrieved Sep. 11, 2019 at http://score.uspto.gov/ScoreAccessWeb/getItem.htm?AppId=15548577&seqId=09323b67 . . . 4 pages.
Score Search Results Details for U.S. Appl. No. 15/548,577 and Search Result 20190107_143514_us-15-548-577-36.rapbm. Search run on Jan. 7, 2019. Copy retrieved Sep. 11, 2019 at http://score.uspto.gov/ScoreAccessWeb/getItem.htm?AppId=15548577&seqId=09323b67 4 pages.
Score Search Results Detail for U.S. Appl. No. 17/862,721 and Search Results 20220829_091720_us-17-862-721-16.rag. Search run on Aug. 29, 2022. Copy retrieved Aug. 30, 2022 at score.USPTO.gov/ScoreAccessWeb/getItemDetail?appId=17862721&docId=bc544287-1664-44c7-9aff-7ec7ba8cb7ea&itemName=20220829_091720 . . . 14 pages.
Score Search Results Detail for U.S. Appl. No. 17/862,721 and Search Results 20220829_091720_us-17-862-721-16.rai. Search run on Aug. 29, 2022. Copy retrieved Aug. 30, 2022 at score.uspto.gov/ScoreAccessWeb/getItemDetail?appId=17862721&docId=131a34de-dcc5-448f-b75f-7ea24f699275&itemName=20220829_091720_ . . . 8 pages.
Score Search Results Detail for U.S. Appl. No. 17/862,721 and Search Results 20220829_091720_us-17-862-721-16.rapm. Search run on Aug. 29, 2022. Copy retrieved Aug. 30, 2022 at score.uspto.gov/ScoreAccessWeb/getItemDetail?appId=17862721&docId=e6f49583-c02c-4eee-a87c-e0ece396955c&itemName=20220829_091720 . . . 10 pages.
Score Search Results Detail for U.S. Appl. No. 17/862,721 and Search Results 20220829_091720_us-17-862-721-17.rag. Search run on Aug. 29, 2022. Copy retrieved Aug. 30, 2022 at score.USPTO.gov/ScoreAccessWeb/getItemDetail?appId=17862721&docId=cbb41ae5-1511-498f-ac7c-0b33abd2492f&itemName=20220829_091720 . . . 15 pages.
Score Search Results Detail for U.S. Appl. No. 17/862,721 and Search Results 20220829_091720_us-17-862-721-17.rai. Search run on Aug. 29, 2022. Copy retrieved Aug. 31, 2022 at score.uspto.gov/ScoreAccessWeb/getItemDetail?appId=17862721&docId=73e892a9-d59f-4aff-8df1-883c983c2966&itemName=20220829_091720_u . . . 8 pages.
Score Search Results Detail for U.S. Appl. No. 17/862,721 and Search Results 20220829_091720_us-17-862-721-17.rapm. Search run on Aug. 29, 2022. Copy retrieved Aug. 31, 2022 at score.uspto.gov/ScoreAccessWeb/getItemDetail?appId=17862721&docId=9851a8bc-7a77-4e69-985e-903a1f2622ae&itemName=20220829_09172 . . . 10 pages.
Score Search Results Detail for U.S. Appl. No. 17/862,721 and Search Results 20220829_091720_us-17-862-721-17.rpr. Search run on Aug. 29, 2022. Copy retrieved Aug. 31, 2022 at score.uspto.

(56) References Cited

OTHER PUBLICATIONS gov/ScoreAccessWeb/getItemDetail?appId=17862721&docId=e04b2be2-c5c8-4cba-b806-cd02a1efe868&itemName=20220829_091720_ . . . 7 pages.
Score Search Results Detail for U.S. Appl. No. 17/862,721 and Search Results 20220829_091720_us-17-862-721-20.rai. Search run on Aug. 29, 2022. Copy retrieved Aug. 31, 2022 at score.uspto.gov/ScoreAccessWeb/getItemDetail?appId=17862721&docId=d17ad86f-3b93-47e9-a94e-a9258afaa3e3&itemName=20220829_091720_ . . . 9 pages.
Score Search Results Detail for U.S. Appl. No. 17/862,721 and Search Results 20220829_091720_us-17-862-721-20.rapm. Search run on Aug. 29, 2022. Copy retrieved Aug. 31, 2022 at score.uspto.gov/ScoreAccessWeb/getItemDetail?appId=17862721&docId=5747899e-d2f6-4407-8197-6ae6e43ac551&itemName=20220829_09172 . . . 11 pages.
Score Search Results Detail for U.S. Appl. No. 17/862,721 and Search Results 20220829_091720_us-17-862-721-20.rpr. Search run on Aug. 29, 2022. Copy retrieved Aug. 31, 2022 at score.uspto.gov/ScoreAccessWeb/getItemDetail?appId=17862721 &docId=8db4eb9f-566a-448b-8a1b-9244e2b8f0ee&itemName=20220829_091720_ . . . 7 pages.
Score Search Results Detail for U.S. Appl. No. 17/862,721 and Search Results 20220829_091720_us-17-862-721-21.rag. Search run on Aug. 29, 2022. Copy retrieved Aug. 31, 2022 at score.uspto.gov/ScoreAccessWeb/getItemDetail?appId=17862721&docId=69e4190a-317d-4f26-9846-c30ab0601669&itemName=20220829_09172 . . . 14 pages.
Score Search Results Detail for U.S. Appl. No. 17/862,721 and Search Results 20220829_091720_us-17-862-721-21.rai. Search run on Aug. 29, 2022. Copy retrieved Aug. 31, 2022 at score.uspto.gov/ScoreAccessWeb/getItemDetail?appId=17862721&docId=a9c72e86-3699-4e4c-8110-8367d0fe6cf4&itemName=20220829_091720_ . . . 8 pages.
Score Search Results Details for U.S. Appl. No. 15/548,577 and Search Result 20190107_143513_us-15-548-577-37.rag. Search run on Jan. 7, 2019. Copy retrieved Jan. 8, 2019 at http://score.uspto.gov/ScoreAccessWeb/getItem.htm?AppId=15548577&seqId=09323b678 . . . 21 pages.
Score Search Results Details for U.S. Appl. No. 15/548,577 and Search Result 20190107_143514_us-15-548-577-36.rapbm. Search run on Jan. 7, 2019. Copy retrieved Jan. 8, 2019 at http://score.uspto.gov/ScoreAccessWeb/getItem.htm?AppId=15548577&seqId=09323b678 . . . 13 pages.
Score Search Results Details for U.S. Appl. No. 15/548,577 and Search Result 20190107_143514_us-15-548-577-37.rai. Search run on Jan. 7, 2019. Copy retrieved Jan. 8, 2019 at http://score.uspto.gov/ScoreAccessWeb/getItem.htm?AppId=15548577&seqId=09323b678 . . . 11 pages.
Score Search Results Details for U.S. Appl. No. 15/548,577 and Search Result 20190107_145543_us-15-548-577-32.rag. Search run on Jan. 7, 2019. Copy retrieved Jan. 8, 2019 at http://score.uspto.gov/ScoreAccessWeb/getItem.htm?AppId=15548577&seqId=09323b678 . . . 23 pages.
Score Search Results Details for U.S. Appl. No. 15/548,577 and Search Result 20190107_145544_us-15-548-577-32.rai. Search run on Jan. 7, 2019. Copy retrieved Jan. 8, 2019 at http://score.uspto.gov/ScoreAccessWeb/getItem.htm?AppId=15548577&seqId=09323b678 . . . 4 pages.
Score Search Results Details for U.S. Appl. No. 15/548,577 and Search Result 20190107_145544_us-15-548-577-32.rapbm. Search run on Jan. 7, 2019. Copy retrieved Jan. 8, 2019 at http://score.uspto.gov/ScoreAccessWeb/getItem.htm?AppId=15548577&seqId=09323b678 . . . 6 pages.
Score Search Results Details for U.S. Appl. No. 15/548,577 and Search Result 20190107_145544_us-15-548-577-33.rai. Search run on Jan. 7, 2019. Copy retrieved Jan. 8, 2019 at http://score.uspto.gov/ScoreAccessWeb/getItem.htm?AppId=15548577&seqId=09323b678 . . . 4 pages.
Score Search Results Details for U.S. Appl. No. 15/548,577 and Search Result 20190107_145544_us-15-548-577-33.rapbm. Search run on Jan. 7, 2019. Copy retrieved Jan. 8, 2019 at http://score.uspto.gov/ScoreAccessWeb/getItem.htm?AppId=15548577&seqId=09323b678 . . . 12 pages.
Segal, et al. Custom DNA-binding proteins come of age: polydactyl zinc-finger proteins. Curr Opin Biotechnol. Dec. 2001;12(6):632-637. doi: 10.1016/s0958-1669(01)00272-5.
Sharma et al., "Novel cancer immunotherapy agents with survival benefit: recent successes and next steps," Nat Rev Cancer, 11(11):805-812 (2011).
Slavin et al. Allogeneic cell therapy with donor peripheral blood cells and recombinant human interleukin-2 to treat leukemia relapse after allogeneic bone marrow transplantation. Blood (1996) 87 (6): 2195-2204.
Smith and Waterman, "Comparison of biosequences", Advances in Applied Mathematics, vol. 2, Issue 4, Dec. 1981, pp. 482-489.
Strebe et al. Functional knockdown of VCAM-1 at the post-translational level with ER retained antibodies. Journal of Immunological Methods 341 (2009) 30-40. Available online Nov. 25, 2008.
Till et al. CD20-specific adoptive immunotherapy for lymphoma using a chimeric antigen receptor with both CD28 and 4-1BB domains: pilot clinical trial results. Blood 119(17):3940-3950 (2012).
Todorovska et al. Design and application of diabodies, triabodies and tetrabodies for cancer targeting. Journal of Immunological Methods 248 (2001) 47-66.
Topp et al. Targeted therapy with the T-cell-engaging antibody blinatumomab of chemotherapy-refractory minimal residual disease in B-lineage acute lymphoblastic leukemia patients results in high response rate and prolonged leukemia-free survival. J Clin Oncol. Jun. 20, 2011;29(18):2493-8.
Torikai et al. A foundation for universal T-cell based immunotherapy: T cells engineered to express a CD19-specific chimeric-antigen-receptor and eliminate expression of endogenous TCR. Blood 119(24):5697-5705 (2012).
U.S. Appl. No. 15/548,577 Notice of Allowance dated May 4, 2020.
U.S. Appl. No. 15/548,577 Office Action dated Jan. 14, 2019.
U.S. Appl. No. 15/548,577 Office Action dated Jul. 20, 2018.
U.S. Appl. No. 15/548,577 Office Action dated Sep. 17, 2019.
U.S. Appl. No. 17/862,721 Office Action dated Jan. 5, 2023.
U.S. Appl. No. 17/862,721 Office Action dated Sep. 7, 2022.
Vivier, Eric et al., Innate or adaptive immunity? The example of natural killer cells, Science (New York, N.Y.) vol. 331,6013 (2011): 44-9. doi:10.1126/science.1198687.
Wheeler et al. Intrabody and intrakine strategies for molecular therapy. Molecular Therapy, vol. 8, No. 3, pp. 355-366, Sep. 2003.
Zang et al. The B7 family and cancer therapy: costimulation and coinhibition. Clin Cancer Res 13(18) pp. 5271-5279 (Sep. 15, 2007).
Zhan et al. Modification of ricin A chain, by addition of endoplasmic reticulum (KDEL) or Golgi (YQRL) retention sequences, enhances its cytotoxicity and translocation. Cancer Immunology, Immunotherapy. vol. 46, pp. 55-60 (1998).
Zhou, P. et al., "Cells transfected with a non-neutralizing antibody gene are resistant to HIV infection: targeting the endoplasmic reticulum and trans-Golgi network", The Journal of Immunology, 1998, vol. 160, pp. 1489-1496.
Png, et al., "Blockade of CD7 expression in T cells for effective chimeric antigen receptor targeting of T-cell malignancies", Blood Advances, vol. 1, No. 25, Nov. 28, 2017, pp. 2348-2360.
Arakawa et al. Cloning and Sequencing of the VH and YK Genes of an Anti-CD3 Monoclonal Antibody, and Construction of a Mouse/Human Chimeric Antibody. J Biochem, vol. 120, No. 3, pp. 657-662 (1996).
Certificate of Disclosure by Benjamin D. Grimshaw signed Dec. 15, 2021 for: Grimshaw et al. Creating a Null T Cell for Adoptive Immunotherapy. Poster. Mar. 9, 2012. One page.
Certificate of Disclosure by David Linch signed Dec. 16, 2021 for: Grimshaw et al. Creating a Null T Cell for Adoptive Immunotherapy. Poster. Mar. 9, 2012. One page.

(56) References Cited

OTHER PUBLICATIONS

Certificate of Disclosure by Martin Pule signed Dec. 15, 2021 for: Grimshaw et al. Creating a Null T Cell for Adoptive Immunotherapy. Poster. Mar. 9, 2012. One page.
Declaration by Benjamin D. Grimshaw signed Sep. 17, 2022. 2 pages.
Nilsson et al. Retention and retrieval in the endoplasmic reticulum and the Golgi apparatus. Current Opinion in Cell Biology 1994, 6:517-521.
U.S. Appl. No. 17/862,721 Notice of Allowance dated Jun. 9, 2023.

\* cited by examiner

SEQUENCE LISTING

<160> NUMBER OF SEQ ID NOS: 44

<210> SEQ ID NO 1
<211> LENGTH: 289
<212> TYPE: PRT
<213> ORGANISM: Artificial Sequence
<220> FEATURE:
<223> OTHER INFORMATION: synthetic polypeptide

<400> SEQUENCE: 1

Met Ala Leu Pro Val Thr Ala Leu Leu Leu Pro Leu Ala Leu Leu Leu
1               5                   10                  15

His Ala Ala Arg Pro Ile Val Met Thr Gln Ser Pro Ala Thr Leu Ser
            20                  25                  30

Val Thr Pro Gly Asp Arg Val Ser Leu Ser Cys Arg Ala Ser Gln Ser
        35                  40                  45

Ile Ser Asp Tyr Leu His Trp Tyr Gln Gln Lys Ser His Glu Ser Pro
50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Ser Asp Phe Thr Leu Ser Ile Asn
                85                  90                  95

Ser Val Glu Pro Glu Asp Val Gly Val Tyr Tyr Cys Gln Asn Gly His
            100                 105                 110

Ser Phe Pro Leu Thr Phe Gly Ala Gly Thr Lys Leu Glu Leu Arg Arg
        115                 120                 125

Gly Gly Gly Gly Ser Gly Gly Gly Ser Gly Gly Gly Gly Ser Gln
130                 135                 140

Val Gln Leu Gln Gln Pro Gly Thr Glu Leu Val Arg Pro Gly Ser Ser
145                 150                 155                 160

Val Lys Leu Ser Cys Lys Ala Ser Gly Tyr Thr Phe Thr Ser Tyr Trp
                165                 170                 175

Val Asn Trp Val Lys Gln Arg Pro Asp Gln Gly Leu Glu Trp Ile Gly
            180                 185                 190

Arg Ile Asp Pro Tyr Asp Ser Glu Thr His Tyr Asn Gln Lys Phe Thr
        195                 200                 205

Asp Lys Ala Ile Ser Thr Ile Asp Thr Ser Ser Asn Thr Ala Tyr Met
    210                 215                 220

Gln Leu Ser Thr Leu Thr Ser Asp Ala Ser Ala Val Tyr Tyr Cys Ser
225                 230                 235                 240

Arg Ser Pro Arg Asp Ser Ser Thr Asn Leu Ala Asp Trp Gly Gln Gly
                245                 250                 255

Thr Leu Val Thr Val Ser Ser Gly Gly Gly Ser Gly Gly Gly Gly
            260                 265                 270

Ser Gly Gly Gly Gly Ser Gly Gly Gly Gly Ser Ala Glu Lys Asp Glu
        275                 280                 285

Leu

<210> SEQ ID NO 2
<211> LENGTH: 348
<212> TYPE: PRT
<213> ORGANISM: Artificial Sequence
<220> FEATURE:
<223> OTHER INFORMATION: synthetic polypeptide

<400> SEQUENCE: 2

Met Ala Leu Pro Val Thr Ala Leu Leu Leu Pro Leu Ala Leu Leu Leu

His Ala Ala Arg Pro Ile Val Met Thr Gln Ser Pro Ala Thr Leu Ser
            20                  25                  30

Val Thr Pro Gly Asp Arg Val Ser Leu Ser Cys Arg Ala Ser Gln Ser
            35                  40                  45

Ile Ser Asp Tyr Leu His Trp Tyr Gln Gln Lys Ser His Glu Ser Pro
            50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Ser Asp Phe Thr Leu Ser Ile Asn
                85                  90                  95

Ser Val Glu Pro Glu Asp Val Gly Val Tyr Tyr Cys Gln Asn Gly His
                100                 105                 110

Ser Phe Pro Leu Thr Phe Gly Ala Gly Thr Lys Leu Glu Leu Arg Arg
                115                 120                 125

Gly Gly Gly Gly Ser Gly Gly Gly Ser Gly Gly Gly Ser Gln
                130                 135                 140

Val Gln Leu Gln Gln Pro Gly Thr Glu Leu Val Arg Pro Gly Ser Ser
145                 150                 155                 160

Val Lys Leu Ser Cys Lys Ala Ser Gly Tyr Thr Phe Thr Ser Tyr Trp
                165                 170                 175

Val Asn Trp Val Lys Gln Arg Pro Asp Gln Gly Leu Glu Trp Ile Gly
                180                 185                 190

Arg Ile Asp Pro Tyr Asp Ser Glu Thr His Tyr Asn Gln Lys Phe Thr
                195                 200                 205

Asp Lys Ala Ile Ser Thr Ile Asp Thr Ser Ser Asn Thr Ala Tyr Met
                210                 215                 220

Gln Leu Ser Thr Leu Thr Ser Asp Ala Ser Ala Val Tyr Tyr Cys Ser
225                 230                 235                 240

Arg Ser Pro Arg Asp Ser Ser Thr Asn Leu Ala Asp Trp Gly Gln Gly
                245                 250                 255

Thr Leu Val Thr Val Ser Ser Lys Pro Thr Thr Thr Pro Ala Pro Arg
                260                 265                 270

Pro Pro Thr Pro Ala Pro Thr Ile Ala Ser Gln Pro Leu Ser Leu Arg
                275                 280                 285

Pro Glu Ala Cys Arg Pro Ala Ala Gly Gly Ala Val His Thr Arg Gly
                290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Lys Tyr Lys
                325                 330                 335

Ser Arg Arg Ser Phe Ile Glu Glu Lys Lys Met Pro
                340                 345

<210> SEQ ID NO 3
<211> LENGTH: 291
<212> TYPE: PRT
<213> ORGANISM: Artificial Sequence
<220> FEATURE:
<223> OTHER INFORMATION: synthetic polypeptide

<400> SEQUENCE: 3

Met Ala Leu Pro Val Thr Ala Leu Leu Leu Pro Leu Ala Leu Leu Leu
1               5                   10                  15

His Ala Ala Arg Pro Asn Ile Met Met Thr Gln Ser Pro Ser Ser Leu

```
                20                  25                  30
Ala Val Ser Ala Gly Glu Lys Val Thr Met Thr Cys Lys Ser Ser Gln
            35                  40                  45
Ser Val Leu Tyr Ser Ser Asn Gln Lys Asn Tyr Leu Ala Trp Tyr Gln
        50                  55                  60
Gln Lys Pro Gly Gln Ser Pro Lys Leu Leu Ile Tyr Trp Ala Ser Thr
65                  70                  75                  80
Arg Glu Ser Gly Val Pro Asp Arg Phe Thr Gly Ser Gly Ser Gly Thr
                85                  90                  95
Asp Phe Thr Leu Thr Ile Ser Ser Val Gln Pro Glu Asp Leu Ala Val
            100                 105                 110
Tyr Tyr Cys His Gln Tyr Leu Ser Ser His Thr Phe Gly Gly Gly Thr
        115                 120                 125
Lys Leu Glu Ile Lys Arg Gly Gly Gly Ser Gly Gly Gly Gly Gly Ser
    130                 135                 140
Gly Gly Gly Ser Gln Leu Gln Gln Pro Gly Ala Glu Leu Val Arg
145                 150                 155                 160
Pro Gly Ser Ser Val Lys Leu Ser Cys Lys Ala Ser Gly Tyr Thr Phe
                165                 170                 175
Thr Arg Tyr Trp Ile His Trp Val Lys Gln Arg Pro Ile Gln Gly Leu
            180                 185                 190
Glu Trp Ile Gly Asn Ile Asp Pro Ser Asp Ser Glu Thr His Tyr Asn
        195                 200                 205
Gln Lys Phe Lys Asp Lys Ala Thr Leu Thr Val Asp Lys Ser Ser Gly
    210                 215                 220
Thr Ala Tyr Met Gln Leu Ser Ser Leu Thr Ser Glu Asp Ser Ala Val
225                 230                 235                 240
Tyr Tyr Cys Ala Thr Glu Asp Leu Tyr Tyr Ala Met Glu Tyr Trp Gly
                245                 250                 255
Gln Gly Thr Ser Val Thr Val Ser Ser Gly Gly Gly Ser Gly Gly
            260                 265                 270
Gly Gly Ser Gly Gly Gly Gly Ser Gly Gly Gly Gly Ser Ala Glu Lys
        275                 280                 285
Asp Glu Leu
    290

<210> SEQ ID NO 4
<211> LENGTH: 350
<212> TYPE: PRT
<213> ORGANISM: Artificial Sequence
<220> FEATURE:
<223> OTHER INFORMATION: synthetic polypeptide

<400> SEQUENCE: 4

Met Ala Leu Pro Val Thr Ala Leu Leu Leu Pro Leu Ala Leu Leu Leu
1               5                   10                  15
His Ala Ala Arg Pro Asn Ile Met Met Thr Gln Ser Pro Ser Ser Leu
            20                  25                  30
Ala Val Ser Ala Gly Glu Lys Val Thr Met Thr Cys Lys Ser Ser Gln
        35                  40                  45
Ser Val Leu Tyr Ser Ser Asn Gln Lys Asn Tyr Leu Ala Trp Tyr Gln
    50                  55                  60
Gln Lys Pro Gly Gln Ser Pro Lys Leu Leu Ile Tyr Trp Ala Ser Thr
65                  70                  75                  80
Arg Glu Ser Gly Val Pro Asp Arg Phe Thr Gly Ser Gly Ser Gly Thr
```

```
            85                  90                  95
Asp Phe Thr Leu Thr Ile Ser Ser Val Gln Pro Glu Asp Leu Ala Val
            100                 105                 110

Tyr Tyr Cys His Gln Tyr Leu Ser Ser His Thr Phe Gly Gly Gly Thr
            115                 120                 125

Lys Leu Glu Ile Lys Arg Gly Gly Gly Ser Gly Gly Gly Gly Ser
            130                 135                 140

Gly Gly Gly Gly Ser Gln Leu Gln Gln Pro Gly Ala Glu Leu Val Arg
145                 150                 155                 160

Pro Gly Ser Ser Val Lys Leu Ser Cys Lys Ala Ser Gly Tyr Thr Phe
                    165                 170                 175

Thr Arg Tyr Trp Ile His Trp Val Lys Gln Arg Pro Ile Gln Gly Leu
                    180                 185                 190

Glu Trp Ile Gly Asn Ile Asp Pro Ser Asp Ser Glu Thr His Tyr Asn
                195                 200                 205

Gln Lys Phe Lys Asp Lys Ala Thr Leu Thr Val Asp Lys Ser Ser Gly
            210                 215                 220

Thr Ala Tyr Met Gln Leu Ser Ser Leu Thr Ser Glu Asp Ser Ala Val
225                 230                 235                 240

Tyr Tyr Cys Ala Thr Glu Asp Leu Tyr Tyr Ala Met Glu Tyr Trp Gly
                    245                 250                 255

Gln Gly Thr Ser Val Thr Val Ser Ser Lys Pro Thr Thr Pro Ala
                    260                 265                 270

Pro Arg Pro Pro Thr Pro Ala Pro Thr Ile Ala Ser Gln Pro Leu Ser
                275                 280                 285

Leu Arg Pro Glu Ala Cys Arg Pro Ala Ala Gly Gly Ala Val His Thr
            290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Lys
                    325                 330                 335

Tyr Lys Ser Arg Arg Ser Phe Ile Glu Glu Lys Lys Met Pro
                340                 345                 350

<210> SEQ ID NO 5
<211> LENGTH: 488
<212> TYPE: PRT
<213> ORGANISM: Artificial Sequence
<220> FEATURE:
<223> OTHER INFORMATION: synthetic polypeptide

<400> SEQUENCE: 5

Met Ala Leu Pro Val Thr Ala Leu Leu Leu Pro Leu Ala Leu Leu Leu
1               5                   10                  15

His Ala Ala Arg Pro Asn Ile Met Met Thr Gln Ser Pro Ser Ser Leu
            20                  25                  30

Ala Val Ser Ala Gly Glu Lys Val Thr Met Thr Cys Lys Ser Ser Gln
        35                  40                  45

Ser Val Leu Tyr Ser Ser Asn Gln Lys Asn Tyr Leu Ala Trp Tyr Gln
    50                  55                  60

Gln Lys Pro Gly Gln Ser Pro Lys Leu Leu Ile Tyr Trp Ala Ser Thr
65                  70                  75                  80

Arg Glu Ser Gly Val Pro Asp Arg Phe Thr Gly Ser Gly Ser Gly Thr
                85                  90                  95

Asp Phe Thr Leu Thr Ile Ser Ser Val Gln Pro Glu Asp Leu Ala Val
```

```
            100                 105                 110
Tyr Tyr Cys His Gln Tyr Leu Ser Ser His Thr Phe Gly Gly Gly Thr
            115                 120                 125

Lys Leu Glu Ile Lys Arg Gly Gly Gly Ser Gly Gly Gly Gly Ser
            130                 135             140

Gly Gly Gly Gly Ser Gln Leu Gln Gln Pro Gly Ala Glu Leu Val Arg
145                 150                 155                 160

Pro Gly Ser Ser Val Lys Leu Ser Cys Lys Ala Ser Gly Tyr Thr Phe
                165                 170                 175

Thr Arg Tyr Trp Ile His Trp Val Lys Gln Arg Pro Ile Gln Gly Leu
            180                 185                 190

Glu Trp Ile Gly Asn Ile Asp Pro Ser Asp Ser Glu Thr His Tyr Asn
            195                 200                 205

Gln Lys Phe Lys Asp Lys Ala Thr Leu Thr Val Asp Lys Ser Ser Gly
            210                 215                 220

Thr Ala Tyr Met Gln Leu Ser Ser Leu Thr Ser Glu Asp Ser Ala Val
225                 230                 235                 240

Tyr Tyr Cys Ala Thr Glu Asp Leu Tyr Tyr Ala Met Glu Tyr Trp Gly
                245                 250                 255

Gln Gly Thr Ser Val Thr Val Ser Ser Thr Thr Pro Ala Pro Arg
            260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
            290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
            370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
            450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485
```

<210> SEQ ID NO 6
<211> LENGTH: 892
<212> TYPE: DNA
<213> ORGANISM: Artificial Sequence
<220> FEATURE:
<223> OTHER INFORMATION: synthetic polynucleotide

<400> SEQUENCE: 6

| | | |
|---|---|---|
| gaattcggct tccaccatgg ctctgcccgt gaccgccctg ctgctgcctc tggctctgct | 60 |
| gctgcacgct gcccgcccaa tcgtgatgac ccagagccca gccaccctgt ccgtgacacc | 120 |
| tggcgaccgg gtgtctctga gctgcagagc ctcccagtct atcagcgatt acctgcactg | 180 |
| gtatcagcag aagtcccacg agtctccccg gctgctgatc aagtacgcta gccagtctat | 240 |
| cagcggcatc cctagccggt tctccggatc tggaagcgga tccgacttta ccctgagcat | 300 |
| caactccgtg gagccagagg atgtgggcgt gtactattgc cagaatggcc actccttccc | 360 |
| cctgaccttt ggcgccggca caaagctgga gctgcggaga ggcggcggcg gctctggagg | 420 |
| aggaggaagc ggaggaggag gctcccaggt gcagctgcag cagccaggaa cagagctggt | 480 |
| gcggcccggc agctccgtga agctgtcctg taaggcctct ggctacacct tcacaagcta | 540 |
| ttgggtgaac tgggtgaagc agaggcctga ccagggcctg gagtggatcg aaggatcga | 600 |
| cccatacgat tctgagacac actataacca aagtttaca acaaggcca tcagcaccat | 660 |
| cgatacatct agcaataccg cctatatgca gctgtccacc ctgacatctg atgccagcgc | 720 |
| cgtgtactat tgttctagga gccctcgcga ctcctctaca aatctggcag attggggaca | 780 |
| gggcaccctg gtgacagtga gctccggtgg tggcggcagt ggtggcggtg gctcaggcgg | 840 |
| tggtggctcc ggtggcggtg gctctgcaga aaagatgag ttgtaactcg ag | 892 |

<210> SEQ ID NO 7
<211> LENGTH: 1069
<212> TYPE: DNA
<213> ORGANISM: Artificial Sequence
<220> FEATURE:
<223> OTHER INFORMATION: synthetic polynucleotide

<400> SEQUENCE: 7

| | | |
|---|---|---|
| gaattcggct tccaccatgg ctctgcccgt gaccgccctg ctgctgcctc tggctctgct | 60 |
| gctgcacgct gcccgcccaa tcgtgatgac ccagagccca gccaccctgt ccgtgacacc | 120 |
| tggcgaccgg gtgtctctga gctgcagagc ctcccagtct atcagcgatt acctgcactg | 180 |
| gtatcagcag aagtcccacg agtctccccg gctgctgatc aagtacgcta gccagtctat | 240 |
| cagcggcatc cctagccggt tctccggatc tggaagcgga tccgacttta ccctgagcat | 300 |
| caactccgtg gagccagagg atgtgggcgt gtactattgc cagaatggcc actccttccc | 360 |
| cctgaccttt ggcgccggca caaagctgga gctgcggaga ggcggcggcg gctctggagg | 420 |
| aggaggaagc ggaggaggag gctcccaggt gcagctgcag cagccaggaa cagagctggt | 480 |
| gcggcccggc agctccgtga agctgtcctg taaggcctct ggctacacct tcacaagcta | 540 |
| ttgggtgaac tgggtgaagc agaggcctga ccagggcctg gagtggatcg aaggatcga | 600 |
| cccatacgat tctgagacac actataacca aagtttaca acaaggcca tcagcaccat | 660 |
| cgatacatct agcaataccg cctatatgca gctgtccacc ctgacatctg atgccagcgc | 720 |
| cgtgtactat tgttctagga gccctcgcga ctcctctaca aatctggcag attggggaca | 780 |
| gggcaccctg gtgacagtga gctccaagcc aaccacaacc cctgcaccaa ggccacctac | 840 |
| accagcacct accatcgcaa gccagccact gtccctgagg ccagaggcat gtaggcctgc | 900 |
| agcaggaggc gccgtgcaca cacgcggcct ggactttgcc tgcgatatct acatctgggc | 960 |
| accactggca ggaacctgtg gcgtgctgct gctgagcctg gtgattaccc tgtataagta | 1020 | caagtccaga cgctcattca ttgaggaaaa gaaaatgcct taactcgag         1069

<210> SEQ ID NO 8
<211> LENGTH: 898
<212> TYPE: DNA
<213> ORGANISM: Artificial Sequence
<220> FEATURE:
<223> OTHER INFORMATION: synthetic polynucleotide

<400> SEQUENCE: 8
gaattcggct tccaccatgg ctctgcccgt gaccgccctg ctgctgcctc tggctctgct         60
gctgcacgct gcccgcccaa acatcatgat gacccagtcc cccagctccc tggccgtgtc        120
tgccggagag aaggtgacca tgacatgcaa gtctagccag tccgtgctgt actcctctaa        180
ccagaagaat tacctggcct ggtatcagca gaagcccggc cagagcccta agctgctgat        240
ctattgggca agcacccggg agtccggagt gccagacaga ttcaccggaa gcggatccgg        300
aacagacttc accctgacaa tcagctccgt gcagcctgag gacctggccg tgtactattg        360
ccaccagtac ctgtctagcc acccttcgg cggcggcaca aagctggaga tcaagagggg        420
aggaggagga tccggaggag gaggctctgg cggcggcggc agccagctgc agcagccagg        480
agcagagctg gtgaggcccg gctcctctgt gaagctgtct tgtaaggcca gcggctacac        540
cttcacaagg tattggatcc actgggtgaa gcagcgccct atccagggcc tggagtggat        600
cggcaacatc gacccatctg atagcgagac acactacaat cagaagttta aggacaaggc        660
caccctgaca gtggataaga gctccggcac cgcctatatg cagctgtcta gcctgacatc        720
cgaggactct gccgtgtact attgtgccac agaggatctg tactatgcca tggagtactg        780
gggccagggc acctccgtga cagtgtcctc tggtggtggc ggcagtggtg cggtggctc        840
aggcggtggt ggctccggtg cggtggctc tgcagaaaaa gatgagttgt aactcgag        898

<210> SEQ ID NO 9
<211> LENGTH: 1075
<212> TYPE: DNA
<213> ORGANISM: Artificial Sequence
<220> FEATURE:
<223> OTHER INFORMATION: synthetic polynucleotide

<400> SEQUENCE: 9
gaattcggct tccaccatgg ctctgcccgt gaccgccctg ctgctgcctc tggctctgct         60
gctgcacgct gcccgcccaa acatcatgat gacccagtcc cccagctccc tggccgtgtc        120
tgccggagag aaggtgacca tgacatgcaa gtctagccag tccgtgctgt actcctctaa        180
ccagaagaat tacctggcct ggtatcagca gaagcccggc cagagcccta agctgctgat        240
ctattgggca agcacccggg agtccggagt gccagacaga ttcaccggaa gcggatccgg        300
aacagacttc accctgacaa tcagctccgt gcagcctgag gacctggccg tgtactattg        360
ccaccagtac ctgtctagcc acccttcgg cggcggcaca aagctggaga tcaagagggg        420
aggaggagga tccggaggag gaggctctgg cggcggcggc agccagctgc agcagccagg        480
agcagagctg gtgaggcccg gctcctctgt gaagctgtct tgtaaggcca gcggctacac        540
cttcacaagg tattggatcc actgggtgaa gcagcgccct atccagggcc tggagtggat        600
cggcaacatc gacccatctg atagcgagac acactacaat cagaagttta aggacaaggc        660
caccctgaca gtggataaga gctccggcac cgcctatatg cagctgtcta gcctgacatc        720
cgaggactct gccgtgtact attgtgccac agaggatctg tactatgcca tggagtactg        780
gggccagggc acctccgtga cagtgtcctc taagccaacc acaaccctg caccaaggcc        840

| acctacacca gcacctacca tcgcaagcca gccactgtcc ctgaggccag aggcatgtag | 900 |
| gcctgcagca ggaggcgccg tgcacacacg cggcctggac tttgcctgcg atatctacat | 960 |
| ctgggcacca ctggcaggaa cctgtggcgt gctgctgctg agcctggtga ttaccctgta | 1020 |
| taagtacaag tccagacgct cattcattga ggaaaagaaa atgccttaac tcgag | 1075 |

<210> SEQ ID NO 10
<211> LENGTH: 1549
<212> TYPE: DNA
<213> ORGANISM: Artificial Sequence
<220> FEATURE:
<223> OTHER INFORMATION: synthetic polynucleotide

<400> SEQUENCE: 10

| gaattcggct tccaccatgg ctctgcccgt gaccgccctg ctgctgcctc tggctctgct | 60 |
| gctgcacgct gcccgcccaa acatcatgat gacccagtcc cccagctccc tggccgtgtc | 120 |
| tgccggagag aaggtgacca tgacatgcaa gtctagccag tccgtgctgt actcctctaa | 180 |
| ccagaagaat tacctggcct ggtatcagca gaagcccggc cagagcccta agctgctgat | 240 |
| ctattgggca agcacccggg agtccggagt gccagacaga ttcaccggaa gcggatccgg | 300 |
| aacagacttc accctgacaa tcagctccgt gcagcctgag gacctggccg tgtactattg | 360 |
| ccaccagtac ctgtctagcc acccttcgg cggcggcaca aagctggaga tcaagagggg | 420 |
| aggaggagga tccggaggag gaggctctgg cggcggcggc agccagctgc agcagccagg | 480 |
| agcagagctg gtgaggcccg gctcctctgt gaagctgtct tgtaaggcca gcggctacac | 540 |
| cttcacaagg tattggatcc actgggtgaa gcagcgccct atccagggcc tggagtggat | 600 |
| cggcaacatc gacccatctg atagcgagac acactacaat cagaagttta aggacaaggc | 660 |
| cacccctgaca gtggataaga gctccggcac cgcctatatg cagctgtcta gcctgacatc | 720 |
| cgaggactct gccgtgtact attgtgccac agaggatctg tactatgcca tggagtactg | 780 |
| gggccagggc acctccgtga cagtgtcctc taccactaca cctgcaccaa ggcctcccac | 840 |
| acccgctccc actatcgctt ccagccacct gtccctgagg cccgaggcct gcaggccagc | 900 |
| agctggcgga gccgtgcata ctaggggct ggacttcgct tgcgacatct acatctgggc | 960 |
| cccactggca gggacatgcg gagtcctgct gctgtccctg gtcatcacac tgtactgcaa | 1020 |
| gcggggggcgc aaaaaactgc tgtatatctt taagcagcct ttcatgagac cagtgcagac | 1080 |
| aacccaggag gaagatgggt gctcatgccg gtttcccgag gaggaggaag gcggctgcga | 1140 |
| gctgagggtg aagttttccc gctcagcaga tgctcctgcc taccagcagg gccagaacca | 1200 |
| gctgtataat gagctgaacc tgggcagacg cgaagagtat gatgtgctgg acaaaaggcg | 1260 |
| gggaagagac cccgaaatgg gagggaagcc aaggcggaaa aaccccagg agggcctgta | 1320 |
| caatgagctg cagaaggaca aaatggcaga ggcttacagt gagattggga tgaagggaga | 1380 |
| gagacggagg ggaaaagggc acgatggcct gtaccagggg ctgagcacag caaccaaaga | 1440 |
| tacttatgac gcactgcaca tgcaggcact gccacccaga tgacagccag ggatttcac | 1500 |
| cactcaaagg ccagacctgc agacgcccag attatgagac acactcgag | 1549 |

<210> SEQ ID NO 11
<211> LENGTH: 21
<212> TYPE: PRT
<213> ORGANISM: Artificial Sequence
<220> FEATURE:
<223> OTHER INFORMATION: synthetic polypeptide

```
<400> SEQUENCE: 11

Met Ala Leu Pro Val Thr Ala Leu Leu Leu Pro Leu Ala Leu Leu Leu
1               5                   10                  15

His Ala Ala Arg Pro
            20

<210> SEQ ID NO 12
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 12

Gly Gly Gly Gly Ser Gly Gly Gly Gly Ser Gly Gly Gly Gly Ser
1               5                   10                  15

<210> SEQ ID NO 13
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 13

Gly Gly Gly Gly Ser Gly Gly Gly Gly Ser Gly Gly Gly Gly Ser Gly
1               5                   10                  15

Gly Gly Gly Ser Ala Glu Lys Asp Glu Leu
            20                  25

<210> SEQ ID NO 14
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 14

Leu Tyr Lys Tyr Lys Ser Arg Arg Ser Phe Ile Glu Glu Lys Lys Met
1               5                   10                  15

Pro

<210> SEQ ID NO 15
<211> LENGTH: 67
<212> TYPE: PRT
<213> ORGANISM: Artificial Sequence
<220> FEATURE:
<223> OTHER INFORMATION: synthetic polypeptide

<400> SEQUENCE: 15

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Ile
    50                  55                  60

Thr Leu Tyr
65

<210> SEQ ID NO 16
```

<211> LENGTH: 42
<212> TYPE: PRT
<213> ORGANISM: Artificial Sequence
<220> FEATURE:
<223> OTHER INFORMATION: synthetic polypeptide

<400> SEQUENCE: 16

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 17
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 17

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 18
<211> LENGTH: 120
<212> TYPE: PRT
<213> ORGANISM: Artificial Sequence
<220> FEATURE:
<223> OTHER INFORMATION: synthetic polypeptide

<400> SEQUENCE: 18

Gln Val Gln Leu Gln Gln Pro Gly Thr Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val Asn Trp Val Lys Gln Arg Pro Asp Gln Gly Leu Glu Trp Ile
        35                  40                  45

Gly Arg Ile Asp Pro Tyr Asp Ser Glu Thr His Tyr Asn Gln Lys Phe
    50                  55                  60

Thr Asp Lys Ala Ile Ser Thr Ile Asp Thr Ser Ser Asn Thr Ala Tyr
65                  70                  75                  80

Met Gln Leu Ser Thr Leu Thr Ser Asp Ala Ser Ala Val Tyr Tyr Cys
                85                  90                  95

Ser Arg Ser Pro Arg Asp Ser Ser Thr Asn Leu Ala Asp Trp Gly Gln
            100                 105                 110

```
Gly Thr Leu Val Thr Val Ser Ser
        115             120
```

<210> SEQ ID NO 19
<211> LENGTH: 107
<212> TYPE: PRT
<213> ORGANISM: Artificial Sequence
<220> FEATURE:
<223> OTHER INFORMATION: synthetic polypeptide

<400> SEQUENCE: 19

```
Ile Val Met Thr Gln Ser Pro Ala Thr Leu Ser Val Thr Pro Gly Asp
1               5                   10                  15

Arg Val Ser Leu Ser Cys Arg Ala Ser Gln Ser Ile Ser Asp Tyr Leu
            20                  25                  30

His Trp Tyr Gln Gln Lys Ser His Glu Ser Pro Arg Leu Leu Ile Lys
        35                  40                  45

Tyr Ala Ser Gln Ser Ile Ser Gly Ile Pro Ser Arg Phe Ser Gly Ser
    50                  55                  60

Gly Ser Gly Ser Asp Phe Thr Leu Ser Ile Asn Ser Val Glu Pro Glu
65                  70                  75                  80

Asp Val Gly Val Tyr Tyr Cys Gln Asn Gly His Ser Phe Pro Leu Thr
                85                  90                  95

Phe Gly Ala Gly Thr Lys Leu Glu Leu Arg Arg
            100                 105
```

<210> SEQ ID NO 20
<211> LENGTH: 116
<212> TYPE: PRT
<213> ORGANISM: Artificial Sequence
<220> FEATURE:
<223> OTHER INFORMATION: synthetic polypeptide

<400> SEQUENCE: 20

```
Gln Leu Gln Gln Pro Gly Ala Glu Leu Val Arg Pro Gly Ser Ser Val
1               5                   10                  15

Lys Leu Ser Cys Lys Ala Ser Gly Tyr Thr Phe Thr Arg Tyr Trp Ile
            20                  25                  30

His Trp Val Lys Gln Arg Pro Ile Gln Gly Leu Glu Trp Ile Gly Asn
        35                  40                  45

Ile Asp Pro Ser Asp Ser Glu Thr His Tyr Asn Gln Lys Phe Lys Asp
    50                  55                  60

Lys Ala Thr Leu Thr Val Asp Lys Ser Ser Gly Thr Ala Tyr Met Gln
65                  70                  75                  80

Leu Ser Ser Leu Thr Ser Glu Asp Ser Ala Val Tyr Tyr Cys Ala Thr
                85                  90                  95

Glu Asp Leu Tyr Tyr Ala Met Glu Tyr Trp Gly Gln Gly Thr Ser Val
            100                 105                 110

Thr Val Ser Ser
        115
```

<210> SEQ ID NO 21
<211> LENGTH: 113
<212> TYPE: PRT
<213> ORGANISM: Artificial Sequence
<220> FEATURE:
<223> OTHER INFORMATION: synthetic polypeptide

<400> SEQUENCE: 21

```
Asn Ile Met Met Thr Gln Ser Pro Ser Ser Leu Ala Val Ser Ala Gly
```

```
                1               5                  10                 15
              Glu Lys Val Thr Met Thr Cys Lys Ser Ser Gln Ser Val Leu Tyr Ser
                              20                  25                 30

Ser Asn Gln Lys Asn Tyr Leu Ala Trp Tyr Gln Gln Lys Pro Gly Gln
                          35                  40                  45

Ser Pro Lys Leu Leu Ile Tyr Trp Ala Ser Thr Arg Glu Ser Gly Val
                      50                  55                  60

Pro Asp Arg Phe Thr Gly Ser Gly Ser Gly Thr Asp Phe Thr Leu Thr
              65                  70                  75                  80

Ile Ser Ser Val Gln Pro Glu Asp Leu Ala Val Tyr Tyr Cys His Gln
                                  85                  90                  95

Tyr Leu Ser Ser His Thr Phe Gly Gly Gly Thr Lys Leu Glu Ile Lys
                              100                 105                110

Arg

<210> SEQ ID NO 22
<211> LENGTH: 242
<212> TYPE: PRT
<213> ORGANISM: Artificial Sequence
<220> FEATURE:
<223> OTHER INFORMATION: synthetic polypeptide

<400> SEQUENCE: 22

Ile Val Met Thr Gln Ser Pro Ala Thr Leu Ser Val Thr Pro Gly Asp
1               5                   10                  15

Arg Val Ser Leu Ser Cys Arg Ala Ser Gln Ser Ile Ser Asp Tyr Leu
            20                  25                  30

His Trp Tyr Gln Gln Lys Ser His Glu Ser Pro Arg Leu Leu Ile Lys
        35                  40                  45

Tyr Ala Ser Gln Ser Ile Ser Gly Ile Pro Ser Arg Phe Ser Gly Ser
    50                  55                  60

Gly Ser Gly Ser Asp Phe Thr Leu Ser Ile Asn Ser Val Glu Pro Glu
65                  70                  75                  80

Asp Val Gly Val Tyr Tyr Cys Gln Asn Gly His Ser Phe Pro Leu Thr
                85                  90                  95

Phe Gly Ala Gly Thr Lys Leu Glu Leu Arg Arg Gly Gly Gly Gly Ser
            100                 105                 110

Gly Gly Gly Gly Ser Gly Gly Gly Ser Gln Val Gln Leu Gln Gln
        115                 120                 125

Pro Gly Thr Glu Leu Val Arg Pro Gly Ser Ser Val Lys Leu Ser Cys
    130                 135                 140

Lys Ala Ser Gly Tyr Thr Phe Thr Ser Tyr Trp Val Asn Trp Val Lys
145                 150                 155                 160

Gln Arg Pro Asp Gln Gly Leu Glu Trp Ile Gly Arg Ile Asp Pro Tyr
                165                 170                 175

Asp Ser Glu Thr His Tyr Asn Gln Lys Phe Thr Asp Lys Ala Ile Ser
            180                 185                 190

Thr Ile Asp Thr Ser Ser Asn Thr Ala Tyr Met Gln Leu Ser Thr Leu
        195                 200                 205

Thr Ser Asp Ala Ser Ala Val Tyr Tyr Cys Ser Arg Ser Pro Arg Asp
    210                 215                 220

Ser Ser Thr Asn Leu Ala Asp Trp Gly Gln Gly Thr Leu Val Thr Val
225                 230                 235                 240

Ser Ser
```

```
<210> SEQ ID NO 23
<211> LENGTH: 244
<212> TYPE: PRT
<213> ORGANISM: Artificial Sequence
<220> FEATURE:
<223> OTHER INFORMATION: synthetic polypeptide

<400> SEQUENCE: 23

Asn Ile Met Met Thr Gln Ser Pro Ser Leu Ala Val Ser Ala Gly
1               5                   10                  15

Glu Lys Val Thr Met Thr Cys Lys Ser Ser Gln Ser Val Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Val Tyr Tyr Cys His Gln
                85                  90                  95

Tyr Leu Ser Ser His Thr Phe Gly Gly Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Leu Gln Gln Pro Gly Ala Glu Leu Val Arg Pro Gly Ser Ser Val
        130                 135                 140

Lys Leu Ser Cys Lys Ala Ser Gly Tyr Thr Phe Thr Arg Tyr Trp Ile
145                 150                 155                 160

His Trp Val Lys Gln Arg Pro Ile Gln Gly Leu Glu Trp Ile Gly Asn
                165                 170                 175

Ile Asp Pro Ser Asp Ser Glu Thr His Tyr Asn Gln Lys Phe Lys Asp
            180                 185                 190

Lys Ala Thr Leu Thr Val Asp Lys Ser Ser Gly Thr Ala Tyr Met Gln
        195                 200                 205

Leu Ser Ser Leu Thr Ser Glu Asp Ser Ala Val Tyr Tyr Cys Ala Thr
        210                 215                 220

Glu Asp Leu Tyr Tyr Ala Met Glu Tyr Trp Gly Gln Gly Thr Ser Val
225                 230                 235                 240

Thr Val Ser Ser

<210> SEQ ID NO 24
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 24

Lys Asp Glu Leu
1

<210> SEQ ID NO 25
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 25
```

Lys Lys Asp Glu
1

<210> SEQ ID NO 26
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 26

Lys Lys Xaa Xaa
1

<210> SEQ ID NO 27
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 27

Lys Lys Met Pro
1

<210> SEQ ID NO 28
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 28

Tyr Gln Arg Leu
1

<210> SEQ ID NO 29
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 29

Ala Glu Lys Asp Glu Leu
1               5

<210> SEQ ID NO 30
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 30

Gly Gly Gly Gly Ser Gly Gly Gly Ser Gly Gly Gly Gly Ser Gly
1               5                   10                  15

Gly Gly Gly Ser Ala Glu Lys Asp Glu Leu
            20                  25

<210> SEQ ID NO 31
<211> LENGTH: 17

```
<212> TYPE: PRT
<213> ORGANISM: Artificial Sequence
<220> FEATURE:
<223> OTHER INFORMATION: synthetic polypeptide

<400> SEQUENCE: 31

Leu Tyr Lys Tyr Lys Ser Arg Arg Ser Phe Ile Glu Glu Lys Lys Met
1               5                   10                  15
Pro

<210> SEQ ID NO 32
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(4)
<223> OTHER INFORMATION: wherein n is 1-10

<400> SEQUENCE: 32

Gly Gly Gly Ser
1

<210> SEQ ID NO 33
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(4)
<223> OTHER INFORMATION: wherein n is 1-10

<400> SEQUENCE: 33

Gly Gly Ser Gly
1

<210> SEQ ID NO 34
<211> LENGTH: 5
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(5)
<223> OTHER INFORMATION: wherein n is 1-10

<400> SEQUENCE: 34

Gly Gly Ser Gly Gly
1               5

<210> SEQ ID NO 35
<211> LENGTH: 5
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(5)
<223> OTHER INFORMATION: wherein n is 1-10

<400> SEQUENCE: 35

Gly Gly Gly Gly Ser
1               5
```

<210> SEQ ID NO 36
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 36

Gly Gly Gly Gly Ser
1               5

<210> SEQ ID NO 37
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 37

Gly Gly Gly Gly Ser
1               5

<210> SEQ ID NO 38
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 38

Gly Gly Gly Gly Ser Gly Gly Gly Gly Ser
1               5                   10

<210> SEQ ID NO 39
<211> LENGTH: 20
<212> TYPE: PRT
<213> ORGANISM: Artificial Sequence
<220> FEATURE:
<223> OTHER INFORMATION: synthetic polypeptide

<400> SEQUENCE: 39

Gly Gly Gly Gly Ser Gly Gly Gly Gly Ser Gly Gly Gly Gly Ser Gly
1               5                   10                  15

Gly Gly Gly Ser
            20

<210> SEQ ID NO 40
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 40

Tyr Gly Arg Leu
1

<210> SEQ ID NO 41
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 41

-continued

Tyr Gln Arg Leu
1

<210> SEQ ID NO 42
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 42

Tyr Lys Gly Leu
1

<210> SEQ ID NO 43
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 43

Tyr Xaa Xaa Leu
1

<210> SEQ ID NO 44
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 44

Lys Lys Thr Asn
1

BLOCKADE OF CD2 SURFACE EXPRESSION AND EXPRESSION OF CHIMERIC ANTIGEN RECEPTORS FOR IMMUNOTHERAPY OF T-CELL MALIGNANCIES

CROSS-REFERENCE TO RELATED APPLICATIONS

This application is a United States National Stage Application filed under 35 U.S.C. § 371 of International Patent Application No. PCT/US2019/33836 filed May 23, 2019 and published as WO 2019/226945 A1, which claims priority to U.S. Provisional Application No. 62/675,511 filed May 23, 2018, the entire contents of which are incorporated herein by reference in its entirety.

REFERENCE TO A SEQUENCE LISTING

The instant application contains a Sequence Listing which has been submitted electronically in ASCII format and is hereby incorporated by reference in its entirety. Said ASCII copy, created on Apr. 8, 2024, is named "4459_1158_002_Sequence Listing.txt" and is 40,174 bytes in size.

FIELD OF THE INVENTION

The invention described herein relates generally to a clinically effective population of chimeric antigen receptor T cells (CAR-T cells) comprising a protein expression blocking fusion protein that intracellularly binds CD2, and additionally to the use of such CAR-T cells to treat T cell malignancies. The invention also relates to clinically effective populations of other immune cells comprising a protein expression blocking fusion protein that intracellularly binds CD2.

BACKGROUND OF THE INVENTION

Genetically-engineered immune cells are a powerful new treatment for cancer and autoimmune diseases. Results of recent clinical trials with T lymphocytes expressing chimeric antigen receptors (CARs) have provided compelling demonstration of the power of this approach. Chimeric antigen receptors (CARs) can redirect immune cells to specifically recognize and kill tumor cells. CARs are artificial multi-molecular proteins constituted by a single-chain variable region (scFv) of an antibody linked to a signaling molecule via a transmembrane domain. When the scFv ligates its cognate antigen, signal transduction is triggered, resulting in tumor cell killing by CAR-expressing cytotoxic T lymphocytes (Eshhar et al. PNAS USA. 90(2): 720-724, 1993; Geiger et al. J Immunol. 162(10):5931-5939, 1999; Brentjens et al. Nat Med. 9(3):279-286, 2003; Cooper et al. Blood 101(4):1637-1644, 2003; Imai C, et al. Leukemia. 18:676-684, 2004). Clinical trials with CAR-expressing autologous T lymphocytes have shown positive responses in patients with B-cell refractory leukemia and lymphoma (see, e.g., Till et al. Blood 119(17): 3940-3950, 2012; Maude et al. N Engl J Med. 371(16):1507-1517, 2014).

It has been shown that CAR-T cells specific for the surface molecule CD19 induced morphologic and molecular remissions in patients with treatment-refractory CD19-positive malignancies, such as acute lymphoblastic leukemia (ALL), chronic lymphocytic leukemia, and non-Hodgkin lymphoma. Other malignancies can be attacked by T cells redirected against different antigens. Hence, the possible applications for genetically-engineered cellular therapy in oncology are wide-ranging.

The initial clinical experience with CAR-T cell infusions has also identified potential limitations, which could seriously diminish therapeutic effect and hamper development. A major issue is the variable fitness of immune cells collected from patients with cancer, resulting in an unpredictable capacity to expand in vivo, and exert anti-tumor effects. This variability complicates the identification of the most effective cell dosages, might lead to the infusion of short-lived and ineffective cell products, and could ultimately prevent the development of a consistent "living drug". The use of T lymphocytes from healthy donors should improve effectiveness and consistency, but carries the risk of graft-versus-host disease (GvHD), a serious, and potentially fatal, consequence of donor lymphocyte infusion. In such allogeneic setting, additional modifications to the infused T cells are required to suppress their capacity to recognize tissue antigens expressed by indispensable cells.

In sum, there is a significant unmet need for new therapeutic options for patients with cancer and autoimmune diseases.

SUMMARY OF THE INVENTION

Provided herein is a simple and effective method for the blockade of surface receptor expression in immune cells. Specific constructs, named Protein Expression Blockers (PEBLs), prevent transport of targeted proteins to the cell membrane. PEBL constructs can be readily combined with other gene modifications and be incorporated into existing large-scale cGMP-grade protocols for ex vivo cell processing to optimize the function of immune cells.

In one aspect, provided herein is an engineered immune cell comprising:
  (i) a CD2 blocking polypeptide comprising a single chain variable fragment (scFv) that binds CD2 linked to the N-terminus of a cellular localizing domain, wherein the cellular localizing domain comprises an amino acid sequence selected from the group consisting of an endoplasmic reticulum (ER) retention sequence, a Golgi retention sequence, and a proteosome localizing sequence, and wherein said CD2 blocking polypeptide remains intracellularly within said engineered cell and binds endogenous CD2 within the engineered cell; and
  (ii) a chimeric antigen receptor (CAR) comprising a CD2 targeting domain, a transmembrane domain, and a signaling domain, In some embodiments, the scFv comprises a variable heavy chain (VH) sequence having at least 90% sequence identity to SEQ ID NO:18 and a variable light chain (VL) sequence having at least 90% sequence identity to SEQ ID NO: 19.

In some embodiments, the scFv comprises a variable heavy chain (VH) sequence having at least 90% sequence identity to SEQ ID NO:20 and a variable light chain (VL) sequence having at least 90% sequence identity to SEQ ID NO:21.

In some embodiments, the ER retention sequence comprises an amino acid sequence selected from the group consisting of KDEL (SEQ ID NO: 24), KKXX (SEQ ID NO: 26), KKMP (SEQ ID NO: 27), and KKTN (SEQ ID NO: 44), wherein X can be any amino acid; or the Golgi retention sequence is selected from the group consisting of YGRL (SEQ ID NO: 40), YQRL (SEQ ID NO: 41), YKGL (SEQ ID NO: 42), and YXXL (SEQ ID NO: 43), wherein X can be any amino acid.

In some embodiments, the CD2 blocking polypeptide further comprises a transmembrane domain linked between the scFv and either the ER retention sequence domain comprising KKMP or KKTN or the Golgi retention sequence domain comprising YGRL, YQRL, YKGL, wherein the transmembrane domain is a transmembrane domain selected from any one of the group consisting of CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, and FGFR2B.

In some embodiments, the transmembrane domain comprises a hinge-transmembrane domain of CD8α.

In some embodiments, the CD2 blocking polypeptide comprises an amino acid sequence having at least 90% sequence identity to any one selected from the group consisting of SEQ ID NOS: 1-4.

In some embodiments, the CAR is an anti-CD2-4-1BB-CD3ζ CAR. In some embodiments, the anti-CD2-4-1BB-CD3ζ CAR comprises an amino acid sequence having at least 90% sequence identity to SEQ ID NO:5.

In some embodiments, the engineered immune cell induces cytotoxicity of CD2+ cells. In some embodiments, CD2 surface expression by the engineered cell is blocked or significantly reduced by the CD2 blocking polypeptide. In some embodiments, the blockage of said CD2 surface expression by the engineered cell persists for at least 6 months. In some embodiments, the blockage of the CD2 surface expression by the engineered cell persists for at least 12 months. In some embodiments, the engineered immune cell proliferates at a substantially equivalent rate as a comparable immune cell.

In some embodiments, the engineered immune cell is an allogeneic cell. In some embodiments, the engineered immune cell is an autologous cell.

In some embodiments, the engineered immune cell is an engineered T cell. In some embodiments, the engineered immune cell is an engineered NK cell.

In another aspect, the invention provides a method of treating cancer in a subject in need thereof comprising administering a therapeutic amount of a composition comprising the engineered immune cell outlined herein to the subject, thereby treating cancer in a subject in need thereof.

In some embodiments, the composition further comprises a pharmaceutically acceptable carrier.

In some embodiments, the cancer is a T-cell malignancy or a CD2 associated cancer. In some embodiments, the T-cell malignancy or said CD2 associated cancer is selected from the group consisting of T cell leukemia T cell lymphoma, T-cell acute lymphoblastic leukemia (T-ALL), early T-cell progenitor acute lymphoblastic leukemia (ETP-ALL), T-cell prolymphocytic leukemia, T-cell large granular lymphocytic leukemia, enteropathy-associated T-cell lymphoma, hepatosplenic T-cell lymphoma, subcutaneous panniculitis-like T-cell lymphoma, cutaneous T-cell lymphomas (CTCL), any subtype of CTCL, mycosis fungoides, Sézary syndrome, primary cutaneous gamma-delta T-cell lymphoma, a malignancy with the T lineage subsets of Non-Hodgkin's lymphoma (NHL), peripheral T-cell lymphoma (PTCL) not otherwise specified (PTCL-NOS) and angioimmunoblastic T-cell lymphoma, and anaplastic large cell lymphoma.

In some embodiments, the administration step is by intravenous infusion, intra-arterial infusion, intraperitoneal infusion, direct injection into tumor and/or perfusion of tumor bed after surgery, implantation at a tumor site in an artificial scaffold, or intrathecal administration.

Also provided herein is a polynucleotide encoding any of the CD2 blocking polypeptides described. Also provided herein is a polynucleotide encoding any of the CARs described.

In some embodiments, an expression vector comprises any one of the polynucleotides encoding a CD2 blocking polypeptide. In some embodiments, an expression vector comprises any one of the polynucleotides encoding a CAR. In some embodiments, the expression vector comprising any one of the polynucleotides encoding a CD2 blocking polypeptide and any one of the polynucleotides encoding a CAR described herein.

Also provided herein is a host cell comprising the expression vector comprises any one of the polynucleotides encoding a CD2 blocking polypeptide and the expression vector comprises any one of the polynucleotides encoding a CAR.

Provided herein is a host cell comprising the expression vector containing any one of the polynucleotides encoding a CD2 blocking polypeptide and any one of the polynucleotides encoding a CAR described herein.

In some aspects, the invention provides a method for producing an engineered immune cell of any one of the embodiments. The method comprises: introducing the exemplary polynucleotides into an immune cell.

In other aspects, the invention provides a method for producing an engineered immune cell of any one of the embodiments. The method comprises: introducing one or more of the exemplary expression vectors into an immune cell.

Additional descriptions of the invention can be found in U.S. Provisional Application No. 62/675,525 filed May 24, 2018, the contents are incorporated herein in its entirety including the sequences, figures, and figures legends.

Detailed descriptions of anti-CD2 monoclonal antibodies 9.6 and 9-1 can be found, e.g., in Kamoun et al. J Exp Med, 1981, 153:207-212 and in Bernard et al., in *Leukocyte Typing II*, 1986, eds. Reinherz, E. L., Haynes, B. F., Nadler, L. M., & Bernstein, I. D. (Springer, New York), pp. 53-66, respectively.

Figure 3:
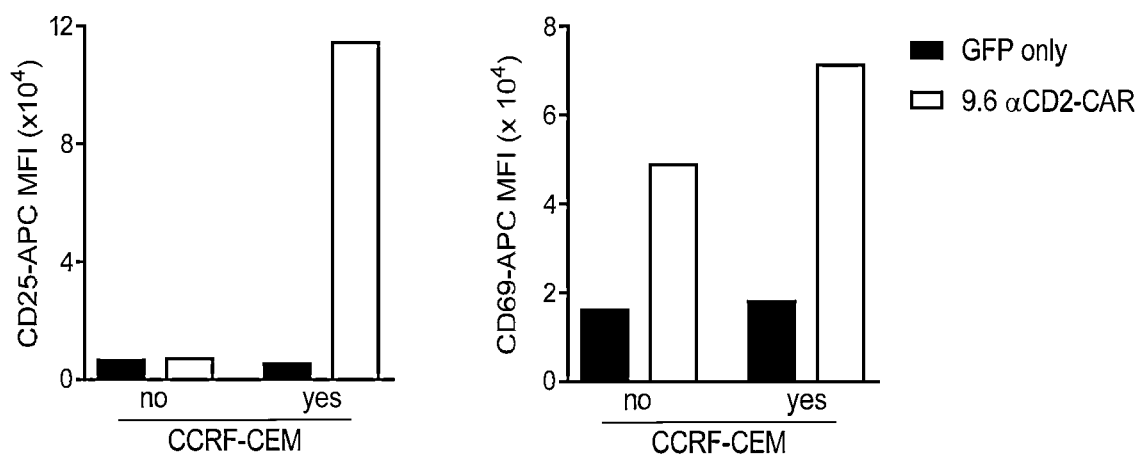

FIG. 3 shows that expression of an anti-CD2 CAR induced expression of activation markers in the presence of CD2+ target cells. The bar graphs show an increased number of CD25+ cells and CD69+ cells of the CCRF-CEM cell line when in the presence of cells expressing the 9.6 anti-CD2 CAR.

Figure 4:
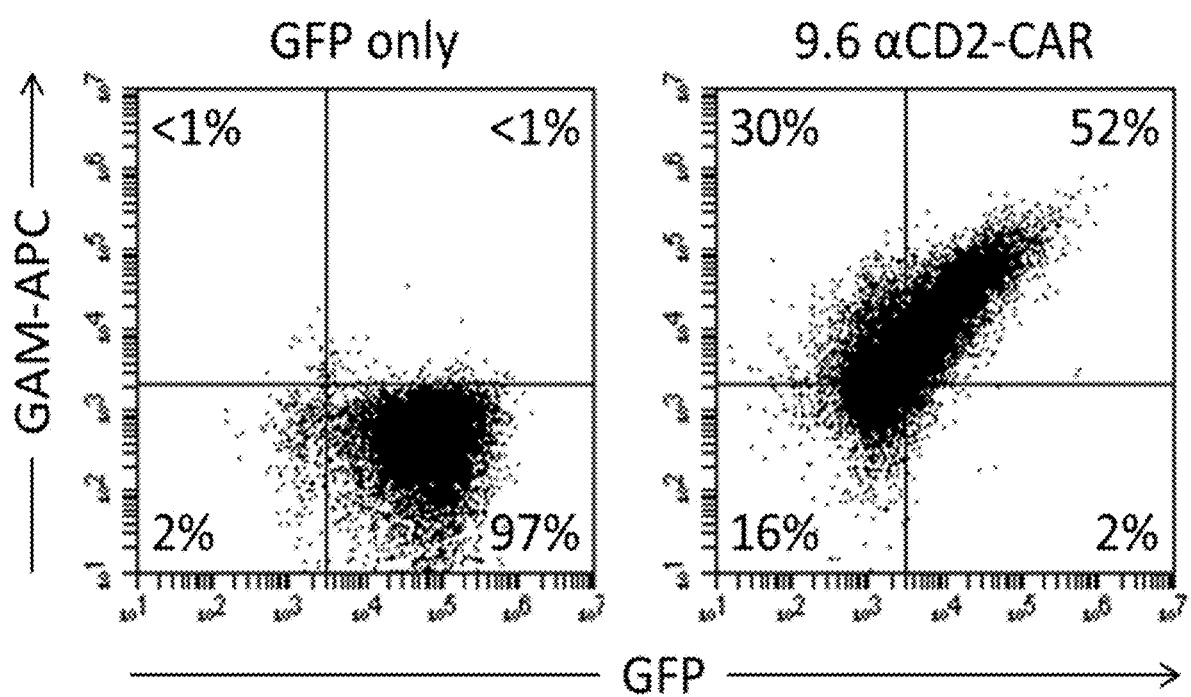

FIG. 4 shows expression of an 9.6 anti-CD2 CAR construct on T cells. T cells were transduced with vectors containing the CAR construct and GFP or GFP only ("Mock"). Flow cytometric dot plots illustrate anti-CD2 CAR expression. An anti-goat anti-mouse antibody APC (GAM-APC) was used.

Figure 5:
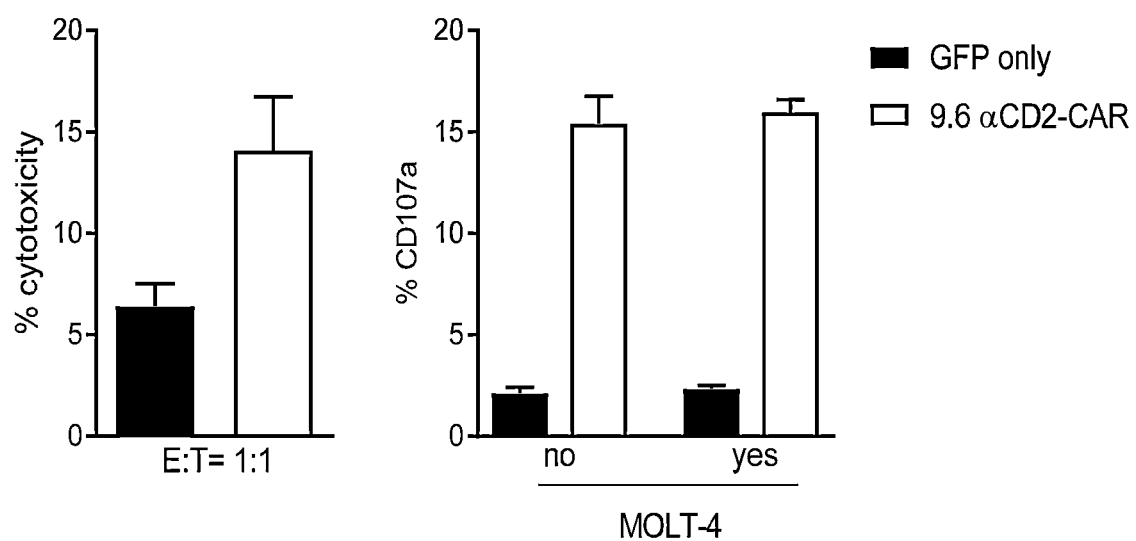

FIG. 5 shows cytoxicity activity of 9.6 anti-CD2 CAR expressing T cells against target cells (CD2+ target cells). Cytotoxicity of CAR- or mock-transduced T cells electroporated either with anti-CD2 scFv-41BB-CD3ζ CAR mRNA or GFP only mRNA was shown in a coculture experiment. CAR T cells and target were plated at a 1:1 effector-to-target ratio (E:T). After several days of co-culture, the number of viable target cells was determined. The bar graph shows that 9.6 anti-CD2 CAR T cells exerted cytotoxicity on the CD2+ target cells. CD107a represents a marker for CD8+ T cell degranulation following stimulation and NK cell functional activity. The bar graph shows that a higher percentage of CD107a+ cells when expressing the 9.6 anti-CD2 CAR compared to GFP only.

Figure 6:
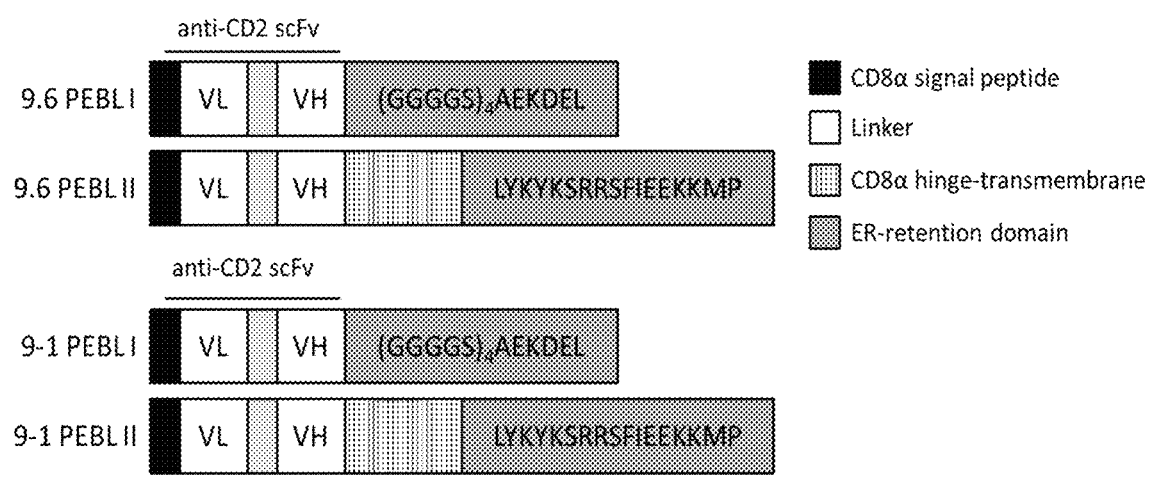

FIG. 6 provides exemplary embodiments of anti-CD2 protein expression blocker (PEBL) constructs described herein. The 9.6 PEBL I construct includes a CD8α signal peptide, a 9.6 anti-CD2 scFv comprising the VL domain connected to the VH domain via a linker, and an ER retention domain. The 9.6 PEBL II construct includes a CD8α signal peptide, a 9.6 anti-CD2 scFv comprising the VL domain connected to the VH domain via a linker, a CD8α hinge-transmembrane domain, and an ER retention domain. The 9-1 PEBL I construct includes a CD8α signal peptide, a 9-1 anti-CD2 scFv comprising the VL domain connected to the VH domain via a linker, and an ER retention domain. The 9-1 PEBL II construct includes a CD8α signal peptide, a 9-1 anti-CD2 scFv comprising the VL domain connected to the VH domain via a linker, a CD8α hinge-transmembrane domain, and an ER retention domain. FIG. 6 discloses SEQ ID NOs: 13, 14, 13, and 14, in order of appearance from top to bottom.

Detailed descriptions of 9.6 anti-CD2 monoclonal antibody and 9-1 anti-CD2 monoclonal antibody can be found, e.g., in Kamoun et al. J Exp Med, 1981, 153:207-212 and in Bernard et al., in *Leukocyte Typing II,* 1986, eds. Reinherz, E. L., Haynes, B. F., Nadler, L. M., & Bernstein, I. D. (Springer, New York), pp. 53-66, respectively. The 9.6 scFv recognizes and binds CD2 on both resting and activated T cells. It also inhibits (blocks) binding of CD58 to CD2. The 9-1 scFv recognizes and binds CD2 on activated T cells. It does not block CD58 binding to CD2.

Figure 7:
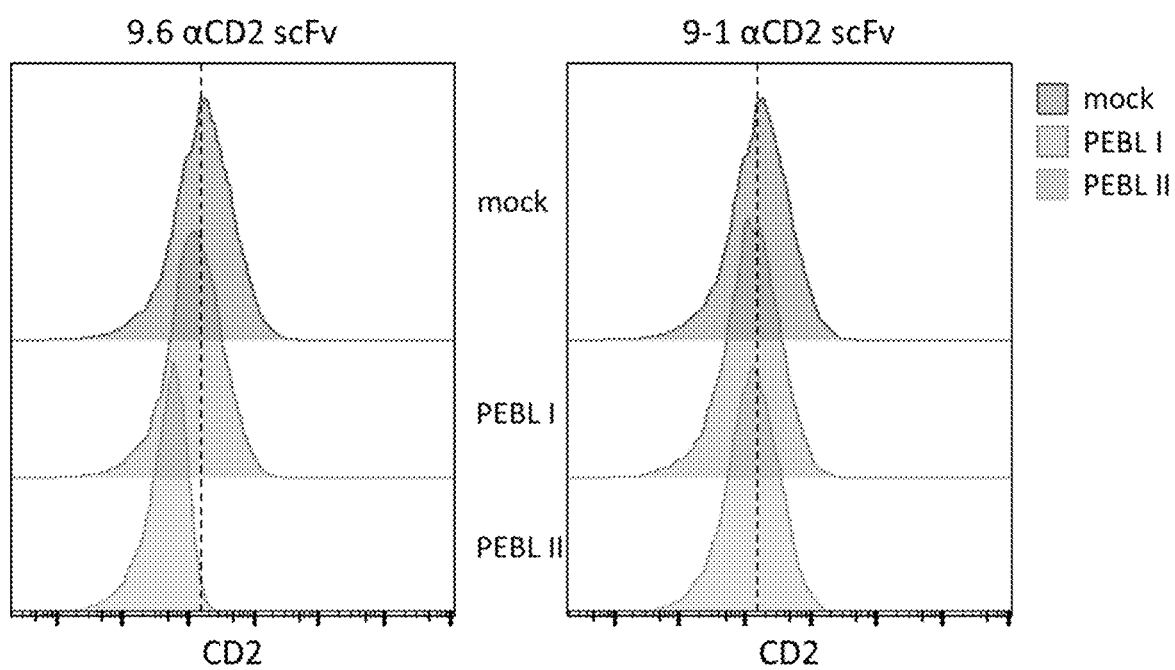

FIG. 7 shows flow cytometry histograms of surface and intracellular expression of CD2 in Jurkat cells transduced with a 9.6 anti-CD2 PEBL I, a 9.6 anti-CD2 PEBL II, a 9-1 anti-CD2 PEBL I, a 9-1 anti-CD2 PEBL II, or GFP alone ("Mock"). Expression of the 9.6 anti-CD2 PEBL II construct in Jurkat cells downregulated expression of CD2.

Figure 8:
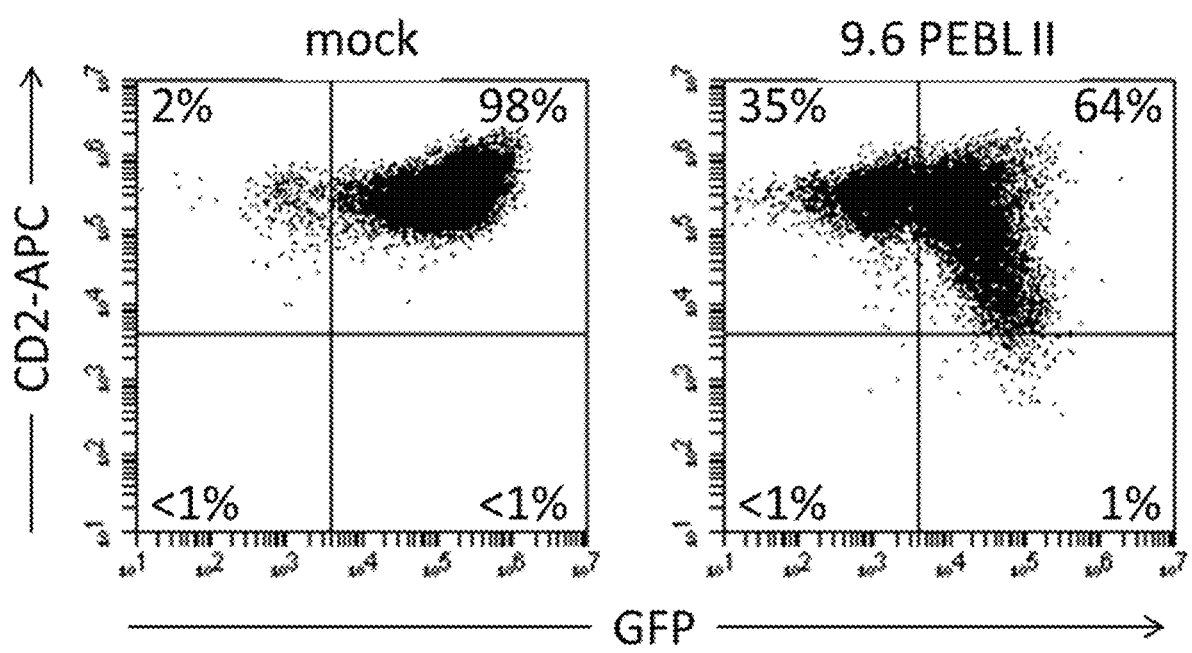

FIG. 8 shows flow cytometry dot plots of surface expression of CD2 in T cells electroporated with 9.6 anti-CD2 PEBL II construct. The data shows downregulation (partial downregulation) of CD2 expression by electroporated T cells.

DETAILED DESCRIPTION OF THE INVENTION

A description of example embodiments of the invention follows.

I. Introduction

The present invention provides a method that allows rapid and efficient downregulation of surface molecules in T cells, including CAR-T cells. In one embodiment of the present invention, provided is an anti-CD2 PEBL (also referred to as a CD2 PEBL) wherein transduction of the anti-CD2 PEBL caused intracellular retention of CD2. PEBL constructs outlined herein may have minimal or no extracellular leakage and are highly effective at blocking CD2 expression and signaling. PEBL expression and CD2 blockage are durable and does not affect expression of other surface molecules. PEBL-expressing immune cells, e.g., T cells can survive and proliferate as well as comparable immune cells, e.g., T cells. Importantly, PEBL-expressing T cells respond normally to CAR signaling and can effectively kill CAR-targeted cells, e.g., cancer cells in vitro. PEBL blockade of CD2 expression and signaling is a simple and effective tool to support infusion of allogeneic T cells, such as CAR-T cells.

II. Definitions

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

In order that the present disclosure can be more readily understood, certain terms are first defined. As used in this application, except as otherwise expressly provided herein, each of the following terms shall have the meaning set forth below. Additional definitions are set forth throughout the application.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

It is understood that wherever aspects are described herein with the language "comprising," otherwise analogous aspects described in terms of "consisting of" and/or "consisting essentially of" are also provided.

As used herein, an "engineered immune cell" refers to an immune cell that has been genetically modified as compared to a naturally-occurring immune cell.

As used herein, the term "nucleic acid" refers to a polymer comprising multiple nucleotide monomers (e.g., ribonucleotide monomers or deoxyribonucleotide monomers). "Nucleic acid" includes, for example, genomic DNA, cDNA, RNA, and DNA-RNA hybrid molecules. Nucleic acid molecules can be naturally occurring, recombinant, or synthetic. In addition, nucleic acid molecules can be single-stranded, double-stranded or triple-stranded. In some embodiments, nucleic acid molecules can be modified. In the case of a double-stranded polymer, "nucleic acid" can refer to either or both strands of the molecule.

The term "nucleotide sequence," in reference to a nucleic acid, refers to a contiguous series of nucleotides that are joined by covalent linkages, such as phosphorus linkages (e.g., phosphodiester, alkyl and aryl-phosphonate, phosphorothioate, phosphotriester bonds), and/or non-phosphorus linkages (e.g., peptide and/or sulfamate bonds). In certain embodiments, the nucleotide sequence encoding, e.g., a target-binding molecule linked to a localizing domain is a heterologous sequence (e.g., a gene that is of a different species or cell type origin).

The terms "nucleotide" and "nucleotide monomer" refer to naturally occurring ribonucleotide or deoxyribonucleotide monomers, as well as non-naturally occurring derivatives and analogs thereof. Accordingly, nucleotides can include, for example, nucleotides comprising naturally occurring bases (e.g., adenosine, thymidine, guanosine, cytidine, uridine, inosine, deoxyadenosine, deoxythymidine, deoxyguanosine, or deoxycytidine) and nucleotides comprising modified bases known in the art.

As will be appreciated by those of skill in the art, in some aspects, the nucleic acid further comprises a plasmid sequence. The plasmid sequence can include, for example, one or more sequences selected from the group consisting of a promoter sequence, a selection marker sequence, and a locus-targeting sequence.

As used herein, the gene encoding a target-binding molecule linked to a localizing domain is sometimes referred to as "gene encoding a PEBL," "polynucleotide encoding a PEBL," "nucleic acid encoding a PEBL," and the like.

In certain embodiments, the target-binding molecule is an antibody or antigen-binding fragment thereof. As used herein, "antibody" means an intact antibody or antigen-binding fragment of an antibody, including an intact antibody or antigen-binding fragment that has been modified or engineered, or that is a human antibody. Examples of antibodies that have been modified or engineered are chimeric antibodies, humanized antibodies, multiparatopic antibodies (e.g., biparatopic antibodies), and multispecific antibodies (e.g., bispecific antibodies). Examples of antigen-binding fragments include Fab, Fab', F(ab')$_2$, Fv, single chain antibodies (e.g., scFv), minibodies and diabodies.

A "diabody" is a small antibody fragment with two antigen-binding sites. The fragments comprise a heavy chain variable region ($V_H$) connected to a light chain variable region ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described in, e.g., patent documents EP 404,097; WO 93/11161; and Holliger et al, (1993) Proc. Natl. Acad. Sci. USA 90: 6444-6448.

In certain embodiments, the antibody is a triabody or a tetrabody. Methods of designing and producing triabodies and tetrabodies are known in the art. See, e.g., Todorovska et al, J. Immunol. Methods 248(1-2):47-66, 2001.

A "domain antibody fragment" is an immunologically functional immunoglobulin fragment containing only the variable region of a heavy chain or the variable region of a light chain. In some instances, two or more VH regions are covalently joined with a peptide linker to create a bivalent domain antibody fragment. The two VH regions of a bivalent domain antibody fragment may target the same or different antigens.

In some embodiments, the antibody is modified or engineered. Examples of modified or engineered antibodies include chimeric antibodies, multiparatopic antibodies (e.g., biparatopic antibodies), and multispecific antibodies (e.g., bispecific antibodies).

As used herein, "multiparatopic antibody" means an antibody that comprises at least two single domain antibodies, in which at least one single domain antibody is directed against a first antigenic determinant on an antigen and at least one other single domain antibody is directed against a second antigenic determinant on the same antigen. Thus, for example, a "biparatopic" antibody comprises at least one single domain antibody directed against a first antigenic determinant on an antigen and at least one further single domain antibody directed against a second antigenic determinant on the same antigen.

As used herein, "multispecific antibody" means an antibody that comprises at least two single domain antibodies, in which at least one single domain antibody is directed against a first antigen and at least one other single domain antibody is directed against a second antigen (different from the first antigen). Thus, for example, a "bispecific" antibody is one that comprises at least one single domain antibody directed against a first antigen and at least one further single domain antibody directed against a second antigen, e.g., different from the first antigen.

In some embodiments, the antibodies disclosed herein are monoclonal antibodies, e.g., murine monoclonal antibodies. Methods of producing monoclonal antibodies are known in the art. See, for example, Pluckthun (1994) The Pharmacology of Monoclonal Antibodies, Vol. 113, Rosenburg and Moore eds. Springer-Verlag, New York, pp. 269-315.

A "Fab fragment" comprises one light chain and the CHI and variable regions of one heavy chain. The heavy chain of a Fab molecule cannot form a disulfide bond with another heavy chain molecule.

An "Fc" region contains two heavy chain fragments comprising the CH2 and CH3 domains of an antibody. The two heavy chain fragments are held together by two or more disulfide bonds and by hydrophobic interactions of the CH3 domains.

A "Fab' fragment" contains one light chain and a portion of one heavy chain that contains the VH domain and the CHI domain and also the region between the CHI and CH2 domains, such that an interchain disulfide bond can be formed between the two heavy chains of two Fab' fragments to form a F(ab')2 molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

In a particular embodiment, the target-binding molecule is single-chain Fv antibody ("scFv antibody"). scFv refers to antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. For a review of scFv, see Pluckthun (1994) The Pharmacology Of Monoclonal Antibodies, vol. 113, Rosenburg and Moore eds. Springer-Verlag, New York, pp. 269-315. See also, PCT Publication No. WO 88/01649 and U.S. Pat. Nos. 4,946,778 and 5,260,203.

The term "sequence identity" means that two nucleotide or amino acid sequences, when optimally aligned, such as by the programs GAP or BESTFIT using default gap weights, share at least, e.g., 70% sequence identity, or at least 80% sequence identity, or at least 85% sequence identity, or at least 90% sequence identity, or at least 90% sequence identity or more. For sequence comparison, typically one sequence acts as a reference sequence (e.g., parent sequence), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et ah, Current Protocols in Molecular Biology). One example of algorithm that is suitable for determining percent sequence identity and sequence similarity is the BLAST algorithm, which is described in Altschul et al, J. Mol. Biol. 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89: 10915 (1989)).

As used herein, "operatively linked" in the context of a PEBL gene refers to a gene encoding a target-binding molecule directly in frame (e.g., without a linker) adjacent to one or more genes encoding one or more localizing domains. Alternatively, the gene encoding a target-binding molecule may be connected to one or more gene encoding one or more localizing domains through a linker sequence, as described herein.

As used herein, "linked" in the context of a protein refers to the joining of a first domain, e.g., a target-binding molecule to a second domain, e.g., a localizing domain. The linker can be an amino acid sequence. Various suitable linkers known in the art can be used to tether the target-binding molecule to a localizing domain. For example, non-naturally occurring peptides, such as a polypeptide consisting of hydrophilic residues of varying length, or a $(GGGGS)_n$ (SEQ ID NO:35) polypeptide, in which n is an integer of, e.g., 3-12, inclusive, can be used according to the present invention.

As used herein, the terms "treat," "treating," or "treatment," refer to counteracting a medical condition (e.g., a condition related to a T cell malignancy) to the extent that the medical condition is improved according to a clinically-acceptable standard.

As used herein, "subject" refers to a mammal (e.g., human, non-human primate, cow, sheep, goat, horse, dog, cat, rabbit, guinea pig, rat, mouse). In certain embodiments, the subject is a human. A "subject in need thereof" refers to a subject (e.g., patient) who has, or is at risk for developing, a disease or condition that can be treated (e.g., improved, ameliorated, prevented) by inducing T cells to exert specific cytotoxicity against malignant T cells.

As defined herein, a "therapeutic amount" refers to an amount that, when administered to a subject, is sufficient to achieve a desired therapeutic effect (treats a condition related to a T cell malignancy) in the subject under the conditions of administration. An effective amount of the agent to be administered can be determined by a clinician of ordinary skill using the guidance provided herein and other methods known in the art, and is dependent on several factors including, for example, the particular agent chosen, the subject's age, sensitivity, tolerance to drugs and overall well-being.

As used herein, "enhanced therapeutic efficacy" refers to one or more of reduced graft-versus-host disease (GvHD) in a host, reduced or elimination of rejection by a host, extended survival in a host, reduced inhibition by the tumor in a host, reduced self-killing in a host, reduced inflammatory cascade in a host, or sustained CAR-mediated signal transduction in a host.

III. Protein Expression Blockers (PEBLs)

The methods described herein enable rapid removal or inactivation of specific target proteins such as CD2 in immune cells. The method relies, in part, on a polypeptide construct containing a target-binding molecule that binds a target (e.g., protein) to be removed or neutralized. The target-binding molecule is linked to a domain (e.g., a localizing domain or intracellular retention domain) that directs the polypeptide to specific cellular compartments, such as the Golgi, endoplasmic reticulum, proteasome, or cellular membrane, depending on the application. For simplicity, a target-binding molecule linked to a localizing domain is sometimes referred to herein as "Protein Expression Blocker" or "PEBL". In some embodiments, the PEBL also include a signal peptide domain. In yet other embodiments, the PEBL contains a transmembrane domain or the cellular localizing domain includes a transmembrane domain.

Exemplary embodiments of PEBLs are shown in FIG. 6 and exemplary amino acid and nucleic acid sequences are provided in Table 1.

TABLE 1

Sequence of PEBLs, CARs and components thereof.

| Name | SEQ ID NO: | Sequence |
|---|---|---|
| 9-1 PEBL I | SEQ ID NO:1 | MALPVTALLLPLALLLHAARPIVMTQSPATLSVTPGDRVSLSCRASQSIS<br>DYLHWYQQKSHESPRLLIKYASQSISGIPSRFSGSGSGSDFTLSINSVEP<br>EDVGVYYCQNGHSFPLTFGAGTKLELRRGGGGSGGGGSGGGGSQVQLQQP<br>GTELVRPGSSVKLSCKASGYTFTSYWVNWVKQRPDQGLEWIGRIDPYDSE<br>THYNQKFTDKAISTIDTSSNTAYMQLSTLTSDASAVYYCSRSPRDSSTNL<br>ADWGQGTLVTVSSGGGGSGGGGSGGGGSGGGGSAEKDEL |
| 9-1 PEBL II | SEQ ID NO:2 | MALPVTALLLPLALLLHAARPIVMTQSPATLSVTPGDRVSLSCRASQSIS<br>DYLHWYQQKSHESPRLLIKYASQSISGIPSRFSGSGSGSDFTLSINSVEP<br>EDVGVYYCQNGHSFPLTFGAGTKLELRRGGGGGGGGSGGGGSQVQLQQP<br>GTELVRPGSSVKLSCKASGYTFTSYWVNWVKQRPDQGLEWIGRIDPYDSE<br>THYNQKFTDKAISTIDTSSNTAYMQLSTLTSDASAVYYCSRSPRDSSTNL<br>ADWGQGTLVTVSSKPTTTPAPRPPTPAPTIASQPLSLRPEACRPAAGGAV<br>HTRGLDFACDIYIWAPLAGTCGVLLLSLVITLYKYKSRRSFIEEKKMP |
| 9.6 PEBL I | SEQ ID NO:3 | MALPVTALLLPLALLLHAARPNIMMTQSPSSLAVSAGEKVTMTCKSSQSV<br>LYSSNQKNYLAWYQQKPGQSPKLLIYWASTRESGVPDRFTGSGSGTDFTL<br>TISSVQPEDLAVYYCHQYLSSHTFGGGTKLEIKRGGGGSGGGGSGGGGSQ<br>LQQPGAELVRPGSSVKLSCKASGYTFTRYWIHWVKQRPIQGLEWIGNIDP<br>SDSETHYNQKFKDKATLTVDKSSGTAYMQLSSLTSEDSAVYYCATEDLYY<br>AMEYWGQGTSVTVSSGGGGSGGGGSGGGGSGGGGSAEKDEL |
| 9.6 PEBL II | SEQ ID NO:4 | MALPVTALLLPLALLLHAARPNIMMTQSPSSLAVSAGEKVTMTCKSSQSV<br>LYSSNQKNYLAWYQQKPGQSPKLLIYWASTRESGVPDRFTGSGSGTDFTL<br>TISSVQPEDLAVYYCHQYLSSHTFGGGTKLEIKRGGGGSGGGGSGGGGSQ<br>LQQPGAELVRPGSSVKLSCKASGYTFTRYWIHWVKQRPIQGLEWIGNIDP<br>SDSETHYNQKFKDKATLTVDKSSGTAYMQLSSLTSEDSAVYYCATEDLYY<br>AMEYWGQGTSVTVSSKPTTTPAPRPPTPAPTIASQPLSLRPEACRPAAGG<br>AVHTRGLDFACDIYIWAPLAGTCGVLLLSLVITLYKYKSRRSFIEEKKMP |
| 9.6 anti-CD2 CAR | SEQ ID NO:5 | MALPVTALLLPLALLLHAARPNIMMTQSPSSLAVSAGEKVTMTCKSSQSV<br>LYSSNQKNYLAWYQQKPGQSPKLLIYWASTRESGVPDRFTGSGSGTDFTL<br>TISSVQPEDLAVYYCHQYLSSHTFGGGTKLEIKRGGGGSGGGGSGGGGSQ<br>LQQPGAELVRPGSSVKLSCKASGYTFTRYWIHWVKQRPIQGLEWIGNIDP<br>SDSETHYNQKFKDKATLTVDKSSGTAYMQLSSLTSEDSAVYYCATEDLYY<br>AMEYWGQGTSVTVSSTTTPAPRPPTPAPTIASQPLSLRPEACRPAAGGAV<br>HTRGLDFACDIYIWAPLAGTCGVLLLSLVITLYCKRGRKKLLYIFKQPFM<br>RPVQTTQEEDGCSCRFPEEEEGGCELRVKFSRSADAPAYQQGQNQLYNEL<br>NLGRREEYDVLDKRRGRDPEMGGKPRRKNPQEGLYNELQKDKMAEAYSEI<br>GMKGERRRGKGHDGLYQGLSTATKDTYDALHMQALPPR |
| 9-1 PEBL I | SEQ ID NO:6 | GAATTCGGCTTCCACCATGGCTCTGCCCGTGACCGCCCTGCTGCTGCCTC<br>TGGCTCTGCTGCTGCACGCTGCCCGCCCAATCGTGATGACCCAGAGCCCA<br>GCCACCCTGTCCGTGACACCTGGCGACCGGGTGTCTCTGAGCTGCAGAGC<br>CTCCCAGTCTATCAGCGATTACCTGCACTGGTATCAGCAGAAGTCCCACG<br>AGTCTCCCCGGCTGCTGATCAAGTACGCTAGCCAGTCTATCAGCGGCATC<br>CCTAGCCGGTTCTCCGGATCTGGAAGCGGATCCGACTTTACCCTGAGCAT<br>CAACTCCGTGGAGCCAGAGGATGTGGGCGTGTACTATTGCCAGAATGGCC<br>ACTCCTTCCCCCTGACCTTTGGCGCCGGCACAAAGCTGGAGCTGCGGAGA<br>GGCGGCGGCGGCTCTGGAGGAGGAGGAAGCGGAGGAGGAGGCTCCCAGGT<br>GCAGCTGCAGCAGCCAGGAACAGAGCTGGTGCGGCCCGGCAGCTCCGTGA<br>AGCTGTCCTGTAAGGCCTCTGGCTACACCTTCACAAGCTATTGGGTGAAC<br>TGGGTGAAGCAGAGGCCTGACCAGGGCCTGGAGTGGATCGGAAGGATCGA<br>CCCATACGATTCTGAGACACACTATAACCAGAAGTTTACAGACAAGGCCA<br>TCAGCACCATCGATACATCTAGCAATACCGCCTATATGCAGCTGTCCACC<br>CTGACATCTGATGCCAGCGCCGTGTACTATTGTTCTAGGAGCCCTCGCGA<br>CTCCTCTACAAATCTGGCAGATTGGGGACAGGGCACCCTGGTGACAGTGA<br>GCTCCGGTGGTGGCGGCAGTGGTGGCGGTGGCTCAGGCGGTGGTGGCTCC<br>GGTGGCGGTGGCTCTGCAGAAAAAGATGAGTTGTAACTCGAG |
| 9-1 PEBL II | SEQ ID NO:7 | GAATTCGGCTTCCACCATGGCTCTGCCCGTGACCGCCCTGCTGCTGCCTC<br>TGGCTCTGCTGCTGCACGCTGCCCGCCCAATCGTGATGACCCAGAGCCCA<br>GCCACCCTGTCCGTGACACCTGGCGACCGGGTGTCTCTGAGCTGCAGAGC<br>CTCCCAGTCTATCAGCGATTACCTGCACTGGTATCAGCAGAAGTCCCACG<br>AGTCTCCCCGGCTGCTGATCAAGTACGCTAGCCAGTCTATCAGCGGCATC<br>CCTAGCCGGTTCTCCGGATCTGGAAGCGGATCCGACTTTACCCTGAGCAT<br>CAACTCCGTGGAGCCAGAGGATGTGGGCGTGTACTATTGCCAGAATGGCC<br>ACTCCTTCCCCCTGACCTTTGGCGCCGGCACAAAGCTGGAGCTGCGGAGA<br>GGCGGCGGCGGCTCTGGAGGAGGAGGAAGCGGAGGAGGAGGCTCCCAGGT<br>GCAGCTGCAGCAGCCAGGAACAGAGCTGGTGCGGCCCGGCAGCTCCGTGA<br>AGCTGTCCTGTAAGGCCTCTGGCTACACCTTCACAAGCTATTGGGTGAAC<br>TGGGTGAAGCAGAGGCCTGACCAGGGCCTGGAGTGGATCGGAAGGATCGA<br>CCCATACGATTCTGAGACACACTATAACCAGAAGTTTACAGACAAGGCCA<br>TCAGCACCATCGATACATCTAGCAATACCGCCTATATGCAGCTGTCCACC<br>CTGACATCTGATGCCAGCGCCGTGTACTATTGTTCTAGGAGCCCTCGCGA<br>CTCCTCTACAAATCTGGCAGATTGGGGACAGGGCACCCTGGTGACAGTGA<br>GCTCCAAGCCAACCACAACCCCTGCACCAAGGCCACCTACACCAGCACCT |

TABLE 1-continued

Sequence of PEBLs, CARs and components thereof.

| Name | SEQ ID NO: | Sequence |
|---|---|---|
| | | ACCATCGCAAGCCAGCCACTGTCCCTGAGGCCAGAGGCATGTAGGCCTGC<br>AGCAGGAGGCGCCGTGCACACACGCGGCCTGGACTTTGCCTGCGATATCT<br>ACATCTGGGCACCACTGGCAGGAACCTGTGGCGTGCTGCTGCTGAGCCTG<br>GTGATTACCCTGTATAAGTACAAGTCCAGACGCTCATTCATTGAGGAAAA<br>GAAAATGCCTTAACTCGAG |
| 9.6 PEBL I | SEQ ID NO: 8 | GAATTCGGCTTCCACCATGGCTCTGCCCGTGACCGCCCTGCTGCTGCCTC<br>TGGCTCTGCTGCTGCACGCTGCCCGCCCAAACATCATGATGACCCAGTCC<br>CCCAGCTCCCTGGCCGTGTCTGCCGGAGAGAAGGTGACCATGACATGCAA<br>GTCTAGCCAGTCCGTGCTGTACTCCTCTAACCAGAAGAATTACCTGGCCT<br>GGTATCAGCAGAAGCCCGGCCAGAGCCCTAAGCTGCTGATCTATTGGGCA<br>AGCACCCGGGAGTCCGGAGTGCCAGACAGATTCACCGGAAGCGGATCCGG<br>AACAGACTTCACCCTGACAATCAGCTCCGTGCAGCCTGAGGACCTGGCCG<br>TGTACTATTGCCACCAGTACCTGTCTAGCCACACCTTCGGCGGCGGCACA<br>AAGCTGGAGATCAAGAGGGGAGGAGGAGGATCCGGAGGAGGAGGCTCTGG<br>CGGCGGCGGCAGCCAGCTGCAGCAGCCAGGAGCAGAGCTGGTGAGGCCCG<br>GCTCCTCTGTGAAGCTGTCTTGTAAGGCCAGCGGCTACACCTTCACAAGG<br>TATTGGATCCACTGGGTGAAGCAGCGCCCTATCCAGGGCCTGGAGTGGAT<br>CGGCAACATCGACCCATCTGATAGCGAGACACACTACAATCAGAAGTTTA<br>AGGACAAGGCCACCCTGACAGTGGATAAGAGCTCCGGCACCGCCTATATG<br>CAGCTGTCTAGCCTGACATCCGAGGACTCTGCCGTGTACTATTGTGCCAC<br>AGAGGATCTGTACTATGCCATGGAGTACTGGGGCCAGGGCACCTCCGTGA<br>CAGTGTCCTCTGGTGGTGGCGGCAGTGGTGGCGGTGGCTCAGGCGGTGGT<br>GGCTCCGGTGGCGGTGGCTCTGCAGAAAAAGATGAGTTGTAACTCGAG |
| 9.6 PEBL II | SEQ ID NO: 9 | GAATTCGGCTTCCACCATGGCTCTGCCCGTGACCGCCCTGCTGCTGCCTC<br>TGGCTCTGCTGCTGCACGCTGCCCGCCCAAACATCATGATGACCCAGTCC<br>CCCAGCTCCCTGGCCGTGTCTGCCGGAGAGAAGGTGACCATGACATGCAA<br>GTCTAGCCAGTCCGTGCTGTACTCCTCTAACCAGAAGAATTACCTGGCCT<br>GGTATCAGCAGAAGCCCGGCCAGAGCCCTAAGCTGCTGATCTATTGGGCA<br>AGCACCCGGGAGTCCGGAGTGCCAGACAGATTCACCGGAAGCGGATCCGG<br>AACAGACTTCACCCTGACAATCAGCTCCGTGCAGCCTGAGGACCTGGCCG |
| 9.6 anti-CD2 CAR | SEQ ID NO: 10 | TGTACTATTGCCACCAGTACCTGTCTAGCCACACCTTCGGCGGCGGCACA<br>AAGCTGGAGATCAAGAGGGGAGGAGGAGGATCCGGAGGAGGAGGCTCTGG<br>CGGCGGCGGCAGCCAGCTGCAGCAGCCAGGAGCAGAGCTGGTGAGGCCCG<br>GCTCCTCTGTGAAGCTGTCTTGTAAGGCCAGCGGCTACACCTTCACAAGG<br>TATTGGATCCACTGGGTGAAGCAGCGCCCTATCCAGGGCCTGGAGTGGAT<br>CGGCAACATCGACCCATCTGATAGCGAGACACACTACAATCAGAAGTTTA<br>AGGACAAGGCCACCCTGACAGTGGATAAGAGCTCCGGCACCGCCTATATG<br>CAGCTGTCTAGCCTGACATCCGAGGACTCTGCCGTGTACTATTGTGCCAC<br>AGAGGATCTGTACTATGCCATGGAGTACTGGGGCCAGGGCACCTCCGTGA<br>CAGTGTCCTCTAAGCCAACCACAACCCCTGCACCAAGGCCACCTACACCA<br>GCACCTACCATCGCAAGCCAGCCACTGTCCCTGAGGCCAGAGGCATGTAG<br>GCCTGCAGCAGGAGGCGCCGTGCACACACGCGGCCTGGACTTTGCCTGCG<br>ATATCTACATCTGGGCACCACTGGCAGGAACCTGTGGCGTGCTGCTGCTG<br>AGCCTGGTGATTACCCTGTATAAGTACAAGTCCAGACGCTCATTCATTGA<br>GGAAAAGAAAATGCCTTAACTCGAG<br>GAATTCGGCTTCCACCATGGCTCTGCCCGTGACCGCCCTGCTGCTGCCTC<br>TGGCTCTGCTGCTGCACGCTGCCCGCCCAAACATCATGATGACCCAGTCC<br>CCCAGCTCCCTGGCCGTGTCTGCCGGAGAGAAGGTGACCATGACATGCAA<br>GTCTAGCCAGTCCGTGCTGTACTCCTCTAACCAGAAGAATTACCTGGCCT<br>GGTATCAGCAGAAGCCCGGCCAGAGCCCTAAGCTGCTGATCTATTGGGCA<br>AGCACCCGGGAGTCCGGAGTGCCAGACAGATTCACCGGAAGCGGATCCGG<br>AACAGACTTCACCCTGACAATCAGCTCCGTGCAGCCTGAGGACCTGGCCG<br>TGTACTATTGCCACCAGTACCTGTCTAGCCACACCTTCGGCGGCGGCACA<br>AAGCTGGAGATCAAGAGGGGAGGAGGAGGATCCGGAGGAGGAGGCTCTGG<br>CGGCGGCGGCAGCCAGCTGCAGCAGCCAGGAGCAGAGCTGGTGAGGCCCG<br>GCTCCTCTGTGAAGCTGTCTTGTAAGGCCAGCGGCTACACCTTCACAAGG<br>TATTGGATCCACTGGGTGAAGCAGCGCCCTATCCAGGGCCTGGAGTGGAT<br>CGGCAACATCGACCCATCTGATAGCGAGACACACTACAATCAGAAGTTTA<br>AGGACAAGGCCACCCTGACAGTGGATAAGAGCTCCGGCACCGCCTATATG<br>CAGCTGTCTAGCCTGACATCCGAGGACTCTGCCGTGTACTATTGTGCCAC<br>AGAGGATCTGTACTATGCCATGGAGTACTGGGGCCAGGGCACCTCCGTGA<br>CAGTGTCCTCTACCACTACACCTGCACCAAGGCCTCCCACACCCGCTCCC<br>ACTATCGCTTCCCAGCCACTGTCCCTGAGGCCCGAGGCCTGCAGGCCAGC<br>AGCTGGCGGAGCCGTGCATACTAGGGGGCTGGACTTCGCTTGCGACATCT<br>ACATCTGGGCCCCACTGGCAGGGACATGCGGAGTCCTGCTGCTGTCCCTG<br>GTCATCACACTGTACTGCAAGCGGGGGCGCAAAAAACTGCTGTATATCTT<br>TAAGCAGCCTTTCATGAGACCAGTGCAGACAACCCAGGAGGAAGATGGGT<br>GCTCATGCCGGTTTCCCGAGGAGGAGGAAGGCGGCTGCGAGCTGAGGGTG<br>AAGTTTTCCCGCTCAGCAGATGCTCCTGCCTACCAGCAGGGCCAGAACCA<br>GCTGTATAATGAGCTGAACCTGGGCAGACGCGAAGAGTATGATGTGCTGG<br>ACAAAAGGCGGGGAAGAGACCCCGAAATGGGAGGGAAGCCAAGGCGGAAA<br>AACCCCCAGGAGGGCCTGTACAATGAGCTGCAGAAGGACAAAATGGCAGA |

TABLE 1-continued

Sequence of PEBLs, CARs and components thereof.

| Name | SEQ ID NO: | Sequence |
|---|---|---|
| | | GGCTTACAGTGAGATTGGGATGAAGGGAGAGAGACGGAGGGGAAAAGGGC
ACGATGGCCTGTACCAGGGGCTGAGCACAGCAACCAAAGATACTTATGAC
GCACTGCACATGCAGGCACTGCCACCCAGATGACAGCCAGGGGATTTCAC
CACTCAAAGGCCAGACCTGCAGACGCCCAGATTATGAGACACACTCGAG |
| CD8 signal peptide | SEQ ID NO: 11 | MALPVTALLLPLALLLHAARP |
| VL-VH linker | SEQ ID NO: 12 | GGGGSGGGGSGGGGS |
| ER-retention domain | SEQ ID NO: 13 | GGGGSGGGGSGGGGSGGGGSAEKDEL |
| ER-retention domain | SEQ ID NO: 14 | LYKYKSRRSFIEEKKMP |
| CD8α hinge and transmembrane domain | SEQ ID NO: 15 | TTTPAPRPPTPAPTIASQPLSLRPEACRPAAGGAVHTRGLDFACDIYIWA
PLAGTCGVLLLSLITLY |
| 4-1BB intracellular signaling domain | SEQ ID NO: 16 | KRGRKKLLYIFKQPFMRPVQTTQEEDGCSCRFPEEEEGGCEL |
| CD3ζ intracellular signaling domain | SEQ ID NO: 17 | RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR |
| Anti-CD2 VH (9-1) | SEQ ID NO: 18 | QVQLQQPGTELVRPGSSVKLSCKASGYTFTSYWVNWVKQRPDQGLEWIGR
IDPYDSETHYNQKFTDKAISTIDTSSNTAYMQLSTLTSDASAVYYCSRSP
RDSSTNLADWGQGTLVTVSS |
| Anti-CD2 VL (9-1) | SEQ ID NO: 19 | IVMTQSPATLSVTPGDRVSLSCRASQSISDYLHWYQQKSHESPRLLIKYA
SQSISGIPSRFSGSGSGSDFTLSINSVEPEDVGVYYCQNGHSFPLTFGAG
TKLELRR |
| Anti-CD2 VH (9.6) | SEQ ID NO: 20 | QLQQPGAELVRPGSSVKLSCKASGYTFTRYWIHWVKQRPIQGLEWIGNID
PSDSETHYNQKFKDKATLTVDKSSGTAYMQLSSLTSEDSAVYYCATEDLY
YAMEYWGQGTSVTVSS |
| Anti-CD2 VL (9.6) | SEQ ID NO: 21 | NIMMTQSPSSLAVSAGEKVTMTCKSSQSVLYSSNQKNYLAWYQQKPGQSP
KLLIYWASTRESGVPDRFTGSGSGTDFTLTISSVQPEDLAVYYCHQYLSS
HTFGGGTKLEIKR |
| Anti-CD2 scFv (9-1) | SEQ ID NO: 22 | IVMTQSPATLSVTPGDRVSLSCRASQSISDYLHWYQQKSHESPRLLIKYA
SQSISGIPSRFSGSGSGSDFTLSINSVEPEDVGVYYCQNGHSFPLTFGAG
TKLELRRGGGGSGGGGSGGGGSQVQLQQPGTELVRPGSSVKLSCKASGYT
FTSYWVNWVKQRPDQGLEWIGRIDPYDSETHYNQKFTDKAISTIDTSSNT
AYMQLSTLTSDASAVYYCSRSPRDSSTNLADWGQGTLVTVSS |
| Anti-CD2 scFv (9) | SEQ ID NO: 23 | NIMMTQSPSSLAVSAGEKVTMTCKSSQSVLYSSNQKNYLAWYQQKPGQSP
KLLIYWASTRESGVPDRFTGSGSGTDFTLTISSVQPEDLAVYYCHQYLSS
HTFGGGTKLEIKRGGGGSGGGGSGGGGSQLQQPGAELVRPGSSVKLSCKA
SGYTFTRYWIHWVKQRPIQGLEWIGNIDPSDSETHYNQKFKDKATLTVDK
SSGTAYMQLSSLTSEDSAVYYCATEDLYYAMEYWGQGTSVTVSS |

It has been shown that secretion of cytokines by activated immune cells triggers cytokine release syndrome and macrophage activation syndrome, presenting serious adverse effects of immune cell therapy (Lee et al., Blood, 2014,124 (2): 188-195).

In some embodiments, the target-binding molecule of the PEBL is a molecule that specifically binds to a CD protein, e.g., human CD2. In some cases, the target-binding molecule is an anti-CD2 antibody or an antigen-binding fragment that binds CD2.

All such suitable binding molecules capable of activating or inactivating an immune response upon binding to a ligand (e.g., peptide or antigen) expressed on a T cell are collectively referred to as a "target-binding molecule." As would be appreciated by those of skill in the art, a target-binding molecule need not contain an antibody or antigen-binding fragment (e.g., scFv); rather the portion of the target-binding molecule that binds to a target molecule can be derived from, e.g., a receptor in a receptor-ligand pair, or a ligand in a receptor-ligand pair.

The target binding molecule of the PEBL described herein can be derived from an antibody that binds CD2. In some embodiments, the antibody that binds CD2 is the anti-CD2 monoclonal antibody 9.6 or a variant thereof. In some embodiments, the antibody that binds CD2 is a humanized variant of the anti-CD2 monoclonal antibody 9.6. In other embodiments, the antibody that binds CD2 is the anti-CD2 monoclonal antibody 9-1. In some embodiments, the antibody that binds CD2 is a humanized variant of the anti-CD2 monoclonal antibody 9-1.

Detailed descriptions of 9.6 and 9-1 can be found, e.g., in Kamoun et al. J Exp Med, 1981, 153:207-212 and in Bernard et al., in *Leukocyte Typing II,* 1986, eds. Reinherz, E. L., Haynes, B. F., Nadler, L. M., & Bernstein, I. D. (Springer, New York), pp. 53-66, respectively.

A humanized antibody refers to an immunoglobulin amino acid sequence variant or fragment thereof which is capable of binding to a target antigen (e.g., human CD2) and which comprises a framework (FR) region having substantially the amino acid sequence of a human immunoglobulin and a CDR having substantially the amino acid sequence of a non-human immunoglobulin. As such, a humanized antibody 9-1 can bind to CD2 and which comprises a FR region having substantially the amino acid sequence of a human immunoglobulin and a CDR having substantially the amino acid sequence of a murine antibody 9-1. Likewise, a humanized antibody 9.6 can bind to CD2 and which comprises a FR region having substantially the amino acid sequence of a human immunoglobulin and a CDR having substantially the amino acid sequence of a murine antibody 9.6.

In general, the humanized antibody comprise substantially all of at least one, and typically two, variable domains (Fab, Fab', F(ab')2, Fabc, Fv) in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain.

The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. The humanized antibody can comprise sequences from more than one class or isotype, and selecting particular constant domains to optimize desired effector functions is within the ordinary skill in the art.

The FR and CDR regions of the humanized antibody need not correspond precisely to the parental sequences, e.g., the import CDR or the consensus FR may be mutagenized by substitution, insertion or deletion of at least one residue so that the CDR or FR residue at that site does not correspond to either the consensus or the import antibody. Such mutations, however, will not be extensive. Usually, at least 75% of the humanized antibody residues will correspond to those of the parental FR and CDR sequences, more often 90%, and most preferably greater than 95%.

In general, humanized antibodies are produced by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen.

Residues that influence antigen binding (e.g., CD2 binding) are defined to be residues that are substantially responsible for the antigen affinity or antigen specificity of a candidate immunoglobulin, in a positive or a negative sense. In some cases, selection and combination of FR residues from the consensus and import sequence is performed to obtain the desired immunoglobulin characteristics. Such desired characteristics include increases in affinity and greater specificity for the target antigen, although it is conceivable that in some circumstances the opposite effects might be desired. In general, the CDR residues are directly and most substantially involved in influencing antigen binding (although not all CDR residues are so involved and therefore need not be substituted into the consensus sequence). However, FR residues also have a significant effect and can exert their influence in at least three ways: They may noncovalently directly bind to antigen, they may interact with CDR residues and they may affect the interface between the heavy and light chains.

Typically, it is necessary to impute the position of antigen from the spatial location of neighboring CDRs and the dimensions and structure of the target antigen. In general, only those humanized antibody residues that are capable of forming salt bridges, hydrogen bonds, or hydrophobic interactions are likely to be involved in non-covalent antigen binding, however residues which have atoms which are separated from antigen spatially by 3.2 Angstroms or less may also non-covalently interact with antigen. Such residues typically are the relatively larger amino acids having the side chains with the greatest bulk, such as tyrosine, arginine, and lysine. Antigen-binding FR residues also typically will have side chains that are oriented into an envelope surrounding the solvent oriented face of a CDR which extends about 7 Angstroms into the solvent from the CDR domain and about 7 Angstroms on either side of the CDR domain, again as visualized by three dimensional modeling.

A residue that interacts with a CDR generally is a residue that either affects the conformation of the CDR polypeptide backbone or forms a noncovalent bond with a CDR residue side chain. Conformation-affecting residues ordinarily are those that change the spatial position of any CDR backbone atom by more than about 0.2 Angstroms. Backbone atoms of CDR sequences are displaced for example by residues that interrupt or modify organized structures such as beta sheets, helices or loops. Residues that can exert a profound effect on the conformation of neighboring sequences include proline and glycine, both of which are capable of introducing bends into the backbone. Other residues that can displace backbone atoms are those that are capable of participating in salt bridges and hydrogen bonds.

A residue that interacts with a CDR side chain is one that is reasonably expected to form a noncovalent bond with a CDR side chain, generally either a salt bridge or hydrogen bond. Such residues are identified by three dimensional positioning of their side chains. A salt or ion bridge could be expected to form between two side chains positioned within about 2.5-3.2 Angstroms of one another that bear opposite charges, for example a lysinyl and a glutamyl pairing. A hydrogen bond could be expected to form between the side chains of residue pairs such as seryl or threonyl with aspartyl or glutamyl (or other hydrogen accepting residues). Such pairings are well known in the protein chemistry art and will be apparent to one skilled in the art upon three dimensional modeling of the candidate antibody.

Since it is not entirely possible to predict in advance what the exact impact of a given substitution will be it may be necessary to make the substitution and assay the candidate antibody for the desired characteristic. These steps, however, are per se routine and well within the ordinary skill of the art.

CDR and FR residues are determined according to a standard sequence definition (Kabat et al., Sequences of Proteins of Immunological Interest, National Institutes of Health, Bethesda Md. (1987), and a structural definition (as in Chothia and Lesk, J. Mol Biol. 196:901-917 (1987). Where these two methods result in slightly different identifications of a CDR, the structural definition is preferred, but the residues identified by the sequence definition method are considered important FR residues for determination of which framework residues to import into a consensus sequence.

Generally, the first step in humanizing an import antibody (e.g., 9-1 antibody or 9.6 antibody) is deriving a consensus amino acid sequence into which to incorporate the import sequences. Next a model is generated for these sequences using the methods described above. In certain embodiments, the consensus human sequences are derived from the most abundant subclasses in the sequence compilation of Kabat et al. (Kabat, E. A. et al., Sequences of Proteins of Immunological Interest (National Institutes of Health, Bethesda, Md., 1987)). While these steps may be taken in different order, typically a structure for the candidate humanized antibody is created by transferring the at least one CDR from the non-human, import sequence into the consensus human structure, after the entire corresponding human CDR has been removed. The humanized antibody may contain human replacements of the non-human import residues at positions within CDRs as defined by sequence variability (Kabat, E. A. et al., Sequences of Proteins of Immunological Interest (National Institutes of Health, Bethesda, Md., 1987)) or as defined by structural variability (Chothia, C. & Lesk, A. M., J. Mol. Biol. 196:901-917 (1987)). Differences between the non-human import and the human consensus framework residues are individually investigated to determine their possible influence on CDR conformation and/or binding to antigen. Investigation of such possible influences is desirably performed through modeling, by examination of the characteristics of the amino acids at particular locations, or determined experimentally through evaluating the effects of substitution or mutagenesis of particular amino acids.

In some embodiments, a humanized antibody is made comprising amino acid sequence of an import, non-human antibody and a human antibody, utilizing the steps of: (a) obtaining the amino acid sequences of at least a portion of an import antibody variable domain and of a consensus human variable domain; (b) identifying Complementarity Determining Region (CDR) amino acid sequences in the import and the human variable domain sequences; (c) substituting an import CDR amino acid sequence for the corresponding human CDR amino acid sequence; (d) aligning the amino acid sequences of a Framework Region (FR) of the import antibody and the corresponding FR of the consensus antibody; (e) identifying import antibody FR residues in the aligned FR sequences that are non-homologous to the corresponding consensus antibody residues; (f) determining if the non-homologous import amino acid residue is reasonably expected to have at least one of the following effects: (1.) non-covalently binds antigen directly, (2.) interacts with a CDR; or (3.) participates in the VL-VH interface; and (g) for any non-homologous import antibody amino acid residue which is reasonably expected to have at least one of these effects, substituting that residue for the corresponding amino acid residue in the consensus antibody FR sequence.

Optionally, one determines if any non-homologous residues identified in step (e) are exposed on the surface of the domain or buried within it, and if the residue is exposed but has none of the effects identified in step (f), one may retain the consensus residue.

Additional descriptions of methods for generating humanized antibodies are found, for example, in U.S. Pat. Nos. 6,054,297; 6,407,213; and 6,719,971, the contents are incorporated herein by reference in their entireties.

In some embodiments, the target binding molecule of the PEBL comprises an anti-CD2 single chain variable fragment comprising a VH domain having at least 90% (e.g., 90%, 91%, 92%, 93%, 94%, 95%, 96%, 97%, 98%, 99%, or 100%) sequence identity to SEQ ID NO:18 and a VL domain having at least 90% (e.g., 90%, 91%, 92%, 93%, 94%, 95%, 96%, 97%, 98%, 99%, or 100%) sequence identity to SEQ ID NO:19. In some instances, a linker connects the VH domain and the VL domain of the scFv. The VH-VL linker can be a $(GGGGS)_n$ (SEQ ID NO:35) linker where n can range from 1 to 6, e.g., 1, 2, 3, 4, 5, or 6. In other instances, the VH-VL linker can be any GS linker or other flexible linker known to one skilled in the art. In some instances, the VH domain comprises at least one (e.g., 1, 2, 3, 4, 5, 6, 7, 8, 9, 10, or more) amino acid substitution in the sequence set forth in SEQ ID NO:18. In some cases, the VL domain comprises at least one (e.g., 1, 2, 3, 4, 5, 6, 7, 8, 9, 10, or more) amino acid substitution in the sequence set forth in SEQ ID NO:19.

In some embodiments, the target binding molecule of the PEBL comprises an anti-CD2 single chain variable fragment comprising a VH domain having at least 90% (e.g., 90%, 91%, 92%, 93%, 94%, 95%, 96%, 97%, 98%, 99%, or 100%) sequence identity to SEQ ID NO:20 and a VL domain having at least 90% (e.g., 90%, 91%, 92%, 93%, 94%, 95%, 96%, 97%, 98%, 99%, or 100%) sequence identity to SEQ ID NO:21. In some instances, a linker connects the VH domain and the VL domain of the scFv. The VH-VL linker can be a (GGGGS)$_n$ (SEQ ID NO:35) linker, where n can range from 1 to 6, e.g., 1, 2, 3, 4, 5, or 6. In other instances, the VH-VL linker can be any GS linker or other flexible linker known to one skilled in the art.

In some cases, anti-CD2 scFv comprises one or more amino acid substitutions that are compatible for binding to CD2 in human immune cells. In some embodiments, the VH domain comprises at least one (e.g., 1, 2, 3, 4, 5, 6, 7, 8, 9, 10, or more) amino acid substitution in the sequence set forth in SEQ ID NO: 18 and the VL domain comprises at least one (e.g., 1, 2, 3, 4, 5, 6, 7, 8, 9, 10, or more) amino acid substitution in the sequence set forth in SEQ ID NO:19 such that the CD2 expression is blocked, reduced, or decreased in a human immune cell. In other embodiments, the VH domain comprises at least one (e.g., 1, 2, 3, 4, 5, 6, 7, 8, 9, 10, or more) amino acid substitution in the sequence set forth in SEQ ID NO:20 and the VL domain comprises at least one (e.g., 1, 2, 3, 4, 5, 6, 7, 8, 9, 10, or more) amino acid substitution in the sequence set forth in SEQ ID NO:21 such that the CD2 expression is blocked, reduced or decreased in a human immune cell.

In various embodiments, the target binding molecule of the PEBL described herein comprises an anti-CD2 scFv comprising at least 90% (e.g., 90%, 91%, 92%, 93%, 94%, 95%, 96%, 97%, 98%, 99%, or 100%) sequence identity to SEQ ID NO:22. In various other embodiments, the target binding molecule comprises an anti-CD2 scFv comprising at least 90% (e.g., 90%, 91%, 92%, 93%, 94%, 95%, 96%, 97%, 98%, 99%, or 100%) sequence identity to SEQ ID NO:23. In some embodiments, the anti-CD2 scFv is a variant of SEQ ID NO:22 and has the same binding activity as the anti-CD2 scFv of SEQ ID NO:22. In other embodiments, the anti-CD2 scFv is a variant of SEQ ID NO:23 and has the same binding activity as the anti-CD2 scFv of SEQ ID NO:23.

In some embodiments, the scFv of the PEBL comprises a variable heavy chain sequence having at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to a variable heavy chain sequence of an anti-CD2 antibody. In some embodiments, the scFv of the present invention comprises a variable light chain sequence having at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to a variable light chain sequence of an anti-CD2 antibody. For instance, the anti-CD2 antibody can be any such recognized by one skilled in the art. In some embodiments, the anti-CD2 antibody or anti-CD2 scFv of the invention is a humanized variant thereof.

In some embodiments, the anti-CD2 scFv of the PEBL binds intracellular CD2 in resting T cells and activated T cells. In other embodiments, the anti-CD2 scFv binds intracellular CD2 in activated T cells. In certain embodiments, the anti-CD2 scFv binds intracellular CD2 in activated T cells, and not resting T cells. In certain embodiments, the anti-CD2 scFv binds intracellular CD2 in an immune cell.

In some embodiments, the anti-CD2 scFv of the PEBL inhibits, blocks, or prevents CD2 binding of CD58. In other embodiments, the anti-CD2 scFv does not inhibit, block, or prevent CD2 binding of CD58.

The cellular localizing domain comprises a retention signaling domain. In some embodiments, the cellular localizing domain comprises a retention signaling domain and a transmembrane domain. In some instances, the cellular localizing domain comprises an endoplasmic reticulum (ER) retention sequence, a Golgi retention sequence, or a proteasome localizing sequence. The cellular localizing domain can include an amino acid sequence that prevents or hinders a protein from being secreted by a cell. The cellular localizing domain can include an amino acid sequence that retains a protein in an intracellular compartment. In some cases, the cellular localizing domain can include an amino acid sequence that retains an anchor a protein in a cellular membrane such as a membrane of the ER or Golgi. For instance, the retention signaling domain can contain a KDEL sequence (SEQ ID NO:24), KKD/E sequence (SEQ ID NO:25), KKXX sequence (SEQ ID NO:26), KKMP sequence (SEQ ID NO:27), or YQRL sequence (SEQ ID NO:28), wherein X represents any amino acid sequence. In some embodiments, if the retention signaling domain comprises KKXX or KKMP, the cellular localizing domain further comprises a CD8a hinge and transmembrane domain, such as but not limited to the sequence of SEQ ID NO: 15. In some cases, the CD8a hinge and transmembrane domain is linked to the N-terminus of the ER retention domain of SEQ ID NO: 14.

In some embodiments, the cellular localizing domain comprises a KDEL sequence (SEQ ID NO:24). In certain embodiments, the cellular localizing domain comprises the sequence of AEKDEL (SEQ ID NO:29). In various embodiments, the cellular localizing domain comprises the sequence of GGGGSGGGGGGGGSGGGGSAEKDEL (SEQ ID NO:30). In particular embodiments, the cellular localizing domain comprises a KKMP sequence (SEQ ID NO:27). In some embodiments, the cellular localizing domain comprises the sequence of LYKYKSRRSFIEEKKMP (SEQ ID NO:31) and a KKMP sequence (SEQ ID NO:27).

In certain embodiments, the cellular localizing domain includes at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to SEQ ID NO:30, as long as it possesses the desired function. In some embodiments, the cellular localizing domain includes at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to SEQ ID NO:31, as long as it possesses the desired function.

In some embodiments, the ER retention sequence comprises an amino acid sequence selected from the group consisting of KDEL, KKXX, KKMP, and KKTN, wherein X can be any amino acid. In some embodiments, the Golgi retention sequence is selected from the group consisting of YGRL (SEQ ID NO:40), YQRL (SEQ ID NO:41), YKGL (SEQ ID NO:42), and YXXL (SEQ ID NO:43), wherein X can be any amino acid.

In some embodiments, proteasome localization is achieved by linking the scFv sequence to a tripartite motif containing 21 (TRIM21) targeting domain sequence and coexpressing the sequence encoding the human TRIM21 E3 ubiquitin ligase protein. TRIM21 binds with high affinity to the Fc domains of antibodies and can recruit the ubiquitin-proteasome complex to degrade molecules (e.g., proteins and peptides) bound to the antibodies. The TRIM21 targeting domain sequence encodes amino acid sequences selected from the group of human immunoglobulin G (IgG) constant regions (Fc) genes such as IgG1, IgG2, or IgG4 and is used to form a fusion protein comprising scFv and Fc domains. In this embodiment, the exogenously expressed TRIM21 protein binds the scFv-Fc fusion protein bound to the target protein (e.g., CD2) and directs the complex to the proteasome for degradation.

Details of the amino acid sequence of the human TRIM21 E3 ligase protein can be found, for example, in NCBI Protein database under NCBI Ref. Seq. No. NP_003132.2. Details of the nucleic acid sequence encoding the human TRIM21 E3 ligase protein can be found, for example, in NCBI Protein database under NCBI Ref. Seq. No. NM_003141.3.

The transmembrane domain can comprise a transmembrane domain or a combination of a hinge and transmembrane domain derived from CD8α, CD8β, 4-1BB, CD28, CD34, CD4, FcεRIγ, CD16, OX40, CD3ζ, CD3ε, CD3γ, CD3δ, TCRα, CD32, CD64, ICOS, VEGFR2, FAS, or FGFR2B. In certain embodiments, the transmembrane domain is derived from CD8α. In certain embodiments, the transmembrane domain is derived from CD8α. The hinge and transmembrane domain derived from CD8α are linked to an ER or Golgi retention signaling domain.

In some embodiments, the transmembrane domain or the hinge and transmembrane domain includes at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to SEQ ID NO:15, as long as it possesses the desired function.

In some embodiments, the transmembrane domain is linked to the retention signaling domain by way of a linker. In some embodiments, the VL domain and VH domain of the scFv are connected by way of a linker. The linker between transmembrane domain and the retention signaling domain is the same sequence of the linker of the scFv. In some instances, the linker between transmembrane domain and the retention signaling domain has a different sequence than the linker of the scFv. Non-limiting examples of a linker include (GS)$_n$, (GGS)$_n$, (GGGS)$_n$ (SEQ ID NO:32), (GGSG)$_n$ (SEQ ID NO:33), (GGSGG)$_n$ (SEQ ID NO:34), or (GGGGS)$_n$ (SEQ ID NO:35), wherein n is 1, 2, 3, 4, 5, 6, 7, 8, 9, or 10. In some embodiment, the linker is (GGGGS)$_3$ (SEQ ID NO:36) or (GGGGS)$_4$ (SEQ ID NO:37). Variation in the linker length may retain or enhance activity, giving rise to superior efficacy in activity studies.

In particular embodiments, the linker comprises, e.g., GGGGSGGGS (SEQ ID NO:38). In some embodiments, the linker comprises, e.g., GGGGGGGGSGGGGSGGGGS (SEQ ID NO:39). In various embodiments, peptide linkers having lengths of about 5 to about 100 amino acids, inclusive, can be used in the present invention. In certain embodiments, peptide linkers having lengths of about 20 to about 40 amino acids, inclusive, can be used in the present invention.

In some embodiments, peptide linkers having lengths of at least 5 amino acids, at least 10 amino acids, at least 15 amino acids, at least 20 amino acids, at least 25 amino acids, at least 30 amino acids, at least 35 amino acids, or at least 40 amino acids can be used in the present invention. As would be appreciated by those of skill in the art, such linker sequences as well as variants of such linker sequences are known in the art. Methods of designing constructs that incorporate linker sequences as well as methods of assessing functionality are readily available to those of skill in the art.

In particular embodiments, the signal peptide of the PEBL is derived from a CD8α signaling peptide. In some embodiments, the signal peptide comprises at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to SEQ ID NO:11. The signal peptide can be located N-terminal to the target-binding molecule.

As those skilled in the art would appreciate, in certain embodiments, any of the sequences of the various components disclosed herein (e.g., signal peptide, scFv, intracellular signaling domain, transmembrane domain, linker, localizing domain, and combinations thereof) can have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the specific corresponding sequences disclosed herein.

Exemplary embodiments of PEBLs described herein are provided in Table 1.

In some embodiments, the nucleic acid sequence encoding an anti-CD2 PEBL comprises one or more nucleic acid sequences set forth in Table 1. In certain embodiments, the anti-CD2 PEBL comprises the nucleotide sequence having at least 90% sequence identity (e.g., 90%, 91%, 92%, 93%, 94%, 95%, 96%, 97%, 98%, 99%, or more sequence identity) to SEQ ID NO:6, or a codon optimized variant thereof. In certain embodiments, the anti-CD2 PEBL comprises the nucleotide sequence having at least 90% sequence identity (e.g., 90%, 91%, 92%, 93%, 94%, 95%, 96%, 97%, 98%, 99%, or more sequence identity) to SEQ ID NO:7, or a codon optimized variant thereof. In some embodiments, the anti-CD2 PEBL comprises the nucleotide sequence having at least 90% sequence identity (e.g., 90%, 91%, 92%, 93%, 94%, 95%, 96%, 97%, 98%, 99%, or more sequence identity) to SEQ ID NO:8, or a codon optimized variant thereof. In other embodiments, the anti-CD2 PEBL comprises the nucleotide sequence having at least 90% sequence identity (e.g., 90%, 91%, 92%, 93%, 94%, 95%, 96%, 97%, 98%, 99%, or more sequence identity) to SEQ ID NO:9, or a codon optimized variant thereof. For instance, the nucleic acid sequence encoding the anti-CD2 PEBL can be modified to obtain to desired expression or activity in human cells, e.g., human immune cells.

Methods of producing antibodies and antibody fragments thereof against any target protein are well-known and routine in the art. Moreover, as exemplified herein, commercially available antibodies to various targets, e.g., CD2 can be used to generate a PEBL molecule, as exemplified herein. Antibodies known in the art, as well as fragments of antibodies (e.g., scFv) derived therefrom, can be used in the present invention, as exemplified herein.

As would be appreciated by those of skill in the art, the chimeric antigen receptor and/or the PEBL molecule can be designed to bind to the targets disclosed herein, as well as variants of the targets disclosed herein. By way of example, a chimeric antigen receptor and/or the PEBL molecule can be designed to bind to a CD2, or a naturally-occurring variant molecule thereof. Such naturally-occurring variants can have the same function as the wild-type form of the molecule. In other embodiments, the variant can have a function that is altered relative to the wild-type form of the molecule (e.g., confers a diseased state).

As would be appreciated by those of skill in the art, the various components of the PEBL molecule constructs can be substituted in different combinations (e.g., to contain a different linker, different localizing sequence, different scFv, etc.), so long as the combination produces a functional PEBL. Methods of assessing functionality for a particular construct are within the ambit of those of skill in the art, as disclosed herein.

IV. Chimeric Antigen Receptors (CARs)

Chimeric Antigen Receptors (CARs) are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. The signaling domains for first generation CARs have been derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX40 (CD134), and 4-1BB (CD137) have been added alone (second generation) or in combination (third generation) to enhance survival and increase proliferation of CAR modified T cells.

In addition to single-chain CARs, in some embodiments, the CARs described herein are multi-chain CARs. Multi-chain CARs or multi-specific CARs comprise several (e.g., two or more) extracellular antigen-(ligand)-binding domains, to simultaneously bind different targets, thereby augmenting immune cell activation and function. In some instances, the extracellular antigen-binding domains are placed in tandem on the same transmembrane polypeptide, and optionally can be separated by a linker. In other instances, the different extracellular antigen-binding domains can be placed on different transmembrane polypeptides composing the multi-chain CAR. Similar to a single-chain CAR, the signal transducing domain of a multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability.

A signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs (ITAMs). Non-limiting examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. A signal transduction domain can also include a co-stimulatory signal molecule. Additional description of bispecific or multispecific CARs are described in WO2014/011988, the contents are incorporated by reference in their entirety.

Accordingly, in one embodiment, the present invention relates to an engineered immune cell that comprises a nucleic acid comprising a nucleotide sequence encoding a chimeric antigen receptor (e.g., CAR), and a nucleic acid comprising a nucleotide sequence encoding a target-binding molecule linked to a localizing domain (e.g., PEBL) that binds CD2. In some embodiments, the present invention relates to an engineered immune cell (such as a CAR-T cell) comprises a chimeric antigen receptor (e.g., CAR) that binds CD2 and a target-binding molecule linked to a localizing domain (e.g., PEBL) that binds CD2. The CD2 CAR of the CAR-T cell binds CD2 on the cell surface of another cell, and the CD2 PEBL the CAR-T cell binds CD2 located in the intracellular compartment of the CAR-T cell. As such, the CD2 PEBL prevents fratricide of CAR-T cells by other CD2 binding CARs.

In certain aspects of the present invention, the chimeric antigen receptor (CAR) binds to a CD2 that is expressed on the surface of a target cell. In other embodiments, the CAR also binds to CD3, CD4, CD5, CD7, CD8, CD25, CD28, CD30, CD38, CD45, CD45RA, CD45RO, CD52, CD56, CD57, CD99, CD127, or CD137.

The CD2 binding domain of the CAR can be an anti-CD2 antibody or an antigen-binding fragment that binds CD2. In some embodiments, the antibody that binds CD2 is the anti-CD2 monoclonal antibody 9.6. In other embodiments, the antibody that binds CD2 is the anti-CD2 monoclonal antibody 9-1. In some embodiments, the antibody that binds CD2 is the anti-CD2 monoclonal antibody 9.6 or a variant thereof. In some embodiments, the antibody that binds CD2 is a humanized variant of the anti-CD2 monoclonal antibody 9.6. In other embodiments, the antibody that binds CD2 is the anti-CD2 monoclonal antibody 9-1. In some embodiments, the antibody that binds CD2 is a humanized variant of the anti-CD2 monoclonal antibody 9-1.

In some embodiments, the CD2 binding domain of the CAR is an anti-CD2 scFv. In some embodiments, the scFv comprises a variable heavy chain sequence having at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to a variable heavy chain sequence of an anti-CD2 antibody. In some embodiments, the scFv of the present invention comprises a variable light chain sequence having at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to a variable light chain sequence of an anti-CD2 antibody. For instance, the anti-CD2 antibody can be any such recognized by one skilled in the art.

In some embodiments, the anti-CD2 single chain variable fragment can contain a VH domain having at least 90% (e.g., 90%, 91%, 92%, 93%, 94%, 95%, 96%, 97%, 98%, 99%, or 100%) sequence identity to SEQ ID NO:18 and a VL domain having at least 90% (e.g., 90%, 91%, 92%, 93%, 94%, 95%, 96%, 97%, 98%, 99%, or 100%) sequence identity to SEQ ID NO:19. In some instances, a linker connects the VH domain and the VL domain of the scFv. The VH-VL linker can be a (GGGGS)$_n$ (SEQ ID NO:35) linker where n can range from 1 to 6, e.g., 1, 2, 3, 4, 5, or 6. In other instances, the VH-VL linker can be any GS linker or other flexible linker known to one skilled in the art.

In some instances, the VH domain comprises at least one (e.g., 1, 2, 3, 4, 5, 6, 7, 8, 9, 10, or more) amino acid substitution in the sequence set forth in SEQ ID NO:18. In some cases, the VL domain comprises at least one (e.g., 1, 2, 3, 4, 5, 6, 7, 8, 9, 10, or more) amino acid substitution in the sequence set forth in SEQ ID NO:19.

In some embodiments, the anti-CD2 scFv contains a VH domain having at least 90% (e.g., 90%, 91%, 92%, 93%, 94%, 95%, 96%, 97%, 98%, 99%, or 100%) sequence identity to SEQ ID NO:20 and a VL domain having at least 90% (e.g., 90%, 91%, 92%, 93%, 94%, 95%, 96%, 97%, 98%, 99%, or 100%) sequence identity to SEQ ID NO:21. In some instances, a linker connects the VH domain and the VL domain of the scFv. The VH-VL linker can be a (GGGGS)$_n$ (SEQ ID NO:35) linker where n can range from 1 to 6, e.g., 1, 2, 3, 4, 5, or 6.

In some cases, anti-CD2 scFv comprises one or more amino acid substitutions that are compatible for binding to CD2 in human immune cells. In some embodiments, the VH domain comprises at least one (e.g., 1, 2, 3, 4, 5, 6, 7, 8, 9, 10, or more) amino acid substitution in the sequence set forth in SEQ ID NO: 18 and the VL domain comprises at least one (e.g., 1, 2, 3, 4, 5, 6, 7, 8, 9, 10, or more) amino acid substitution in the sequence set forth in SEQ ID NO: 19 such that the CD2 expression is blocked, reduced or decreased in a human immune cell. In other embodiments, the VH domain comprises at least one (e.g., 1, 2, 3, 4, 5, 6, 7, 8, 9, 10, or more) amino acid substitution in the sequence set forth in SEQ ID NO:20 and the VL domain comprises at least one (e.g., 1, 2, 3, 4, 5, 6, 7, 8, 9, 10, or more) amino acid substitution in the sequence set forth in SEQ ID NO:21 such that the CD2 expression is blocked, reduced or decreased in a human immune cell.

In various embodiments, the anti-CD2 scFv comprises at least 90% (e.g., 90%, 91%, 92%, 93%, 94%, 95%, 96%, 97%, 98%, 99%, or 100%) sequence identity to SEQ ID NO:22. In various other embodiments, the anti-CD2 scFv comprises at least 90% (e.g., 90%, 91%, 92%, 93%, 94%, 95%, 96%, 97%, 98%, 99%, or 100%) sequence identity to SEQ ID NO:23. In some embodiments, the anti-CD2 scFv is a variant of SEQ ID NO:22 and has the same binding activity as the anti-CD2 scFv of SEQ ID NO:22. In other embodiments, the anti-CD2 scFv is a variant of SEQ ID NO:23 and has the same binding activity as the anti-CD2 scFv of SEQ ID NO:23.

The CD2 binding domain of the PEBL can bind the same epitope of CD2 as the anti-CD2 binding domain of the CAR. In other cases, the anti-CD2 binding domain of the PEBL can bind a different epitope of CD2 than the CD2 binding domain of the CAR. The amino acid sequences of the CD2 binding domain of the PEBL and the CD2 binding domain of the CAR can be substantially identical. Or, the amino acid sequences of the CD2 binding domain of the PEBL and the CD2 binding domain of the CAR can be different. In some embodiments, the sequence of the CD2 binding domain of the PEBL has at least 90% (e.g., 90%, 91%, 92%, 93%, 94%, 95%, 96%, 97%, 98%, 99%, or 100%) sequence identity to the CD2 binding domain of the CAR.

Figure 1:
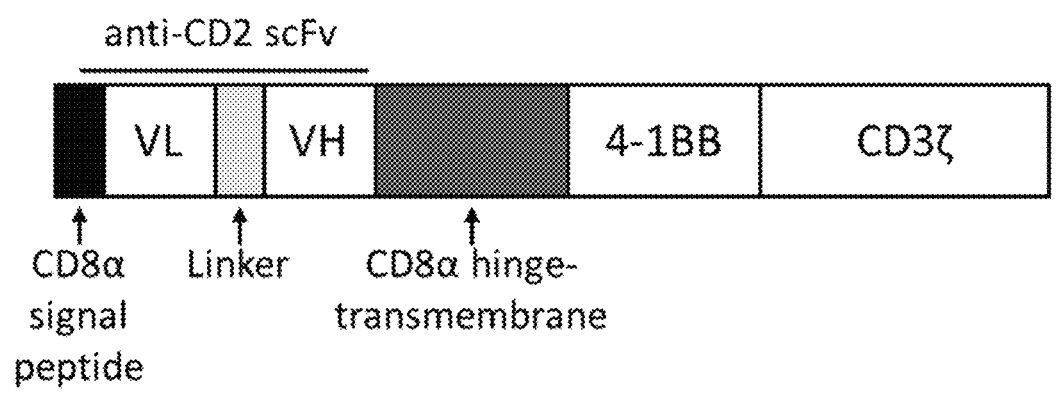
FIG. 1 depicts a schematic of an exemplary anti-CD2 chimeric antigen receptor (CAR) construct described herein.

Exemplary embodiments of CARs are shown in FIG. 1 and exemplary amino acid and nucleic acid sequences are provided in Table 1.

In some embodiments, the nucleic acid sequence encoding an anti-CD2 CAR comprises one or more nucleic acid sequences set forth in Table 1. In certain embodiments, the anti-CD2 CAR comprises the nucleotide sequence having at least 90% sequence identity (e.g., 90%, 91%, 92%, 93%, 94%, 95%, 96%, 97%, 98%, 99%, or more sequence identity) to SEQ ID NO:10, or a codon optimized variant thereof. For instance, the nucleic acid sequence encoding the anti-CD2 CAR can be modified to obtain to desired expression or activity in human cells, e.g., human immune cells.

As those skilled in the art would appreciate, in certain embodiments, any of the sequences of the various components disclosed herein (e.g., signal peptide, scFv, intracellular signaling domain(s), transmembrane domain, linker, and combinations thereof) can have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the specific corresponding sequences disclosed herein.

In some embodiments, the 4-1BB intracellular signaling domain can have at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to SEQ ID NO: 16, as long as it possesses the desired function.

In certain embodiments, the 4-1BB intracellular signaling domain can be replaced by another intracellular signaling domain from a co-stimulatory molecule such as CD28, OX40, ICOS, CD27, GITR, HVEM, TIM1, LFA1, or CD2. In some embodiments, the intracellular signaling domain of the CAR can have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the intracellular signaling domain of CD28, OX40, ICOS, CD27, GITR, HVEM, TIM1, LFA1, or CD2. Optionally, the 4-1BB intracellular signaling domain can also include another intracellular signaling domain (or a portion thereof) from a co-stimulatory molecule such as CD28, OX40, ICOS, CD27, GITR, HVEM, TIM1, LFA1, or CD2. In some embodiments, the additional intracellular signaling domain can have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the intracellular signaling domain of CD28, OX40, ICOS, CD27, GITR, HVEM, TIM1, LFA1, or CD2.

In some embodiments, the CD3zeta (CD3ζ) intracellular signaling domain can have at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to SEQ ID NO:17, as long as it possesses the desired function.

In some instances, the intracellular signaling domain comprises an immunoreceptor tyrosine-based activation motif (ITAM) or a portion thereof, as long as it possesses the desired function. The intracellular signaling domain of the CAR can include a sequence having at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to an ITAM. In certain embodiments, the intracellular signaling domain can have at least 95% sequence identity, at least 96% sequence identity, at least 97% sequence identity, at least 98% sequence identity, at least 99% sequence identity, or 100% sequence identity to FcεRIγ, CD4, CD7, CD8, CD28, OX40 or H2-Kb, as long as it possesses the desired function.

In some embodiments, the CD8alpha (CD8α) hinge and transmembrane domain can have at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to SEQ ID NO: 11, as long as it possesses the desired function.

Hinge and transmembrane sequences suitable for use in the present invention are known in the art, and provided in, e.g., publication WO2016/126213, incorporated by reference in its entirety.

In some embodiments, the hinge and transmembrane domain of the anti-CD2 CAR can include a signaling domain (e.g., transmembrane domain) from CD8α, IgG, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, FGFR2B, or another transmembrane protein. The transmembrane domain may also be a non-naturally occurring hydrophobic protein segment.

In some embodiments, the CD8alpha (CD8α) signal peptide can have at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to SEQ ID NO:11, as long as it possesses the desired function.

V. Engineered Immune Cells

Accordingly, in one embodiment, the present invention relates to an engineered immune cell that expresses a CD2 CAR and a CD2 PEBL. In certain embodiments, the engineered immune cell is an engineered T cell, an engineered natural killer (NK) cell, an engineered NK/T cell, an engineered monocyte, an engineered macrophage, or an engineered dendritic cell. In some embodiments, the immune cell is a peripheral blood mononuclear cell (PBMC)-derived T cell.

In some embodiments, the present invention describes an engineered immune cell expressing a PEBL that binds CD2, such as those outlined herein. In some embodiments, the engineered immune cell expresses a PEBL comprising an amino acid sequence having at least 90% (e.g., 90%, 91%, 92%, 93%, 94%, 95%, 96%, 97%, 98%, 99%, or more) identity to any one selected from SEQ ID NOS:1-4. In some embodiments, the engineered cell expresses a PEBL comprising the amino acid sequence having at least 90% (e.g., 90%, 91%, 92%, 93%, 94%, 95%, 96%, 97%, 98%, 99%, or more) identity to SEQ ID NO:1. In some embodiments, the engineered cell expresses a PEBL comprising the amino acid sequence having at least 90% (e.g., 90%, 91%, 92%, 93%, 94%, 95%, 96%, 97%, 98%, 99%, or more) identity to SEQ ID NO:2. In some embodiments, the engineered cell expresses a PEBL comprising the amino acid sequence having at least 90% (e.g., 90%, 91%, 92%, 93%, 94%, 95%, 96%, 97%, 98%, 99%, or more) identity to SEQ ID NO:3. In some embodiments, the engineered cell expresses a PEBL comprising the amino acid sequence having at least 90% (e.g., 90%, 91%, 92%, 93%, 94%, 95%, 96%, 97%, 98%, 99%, or more) identity to SEQ ID NO:4. In some embodiments, the engineered cell expresses a PEBL comprising the amino acid sequence of SEQ ID NO:1. In some embodiments, the engineered cell expresses a PEBL comprising the amino acid sequence of SEQ ID NO:2. In some embodiments, the engineered cell expresses a PEBL comprising the amino acid sequence of SEQ ID NO:3. In some embodiments, the engineered cell expresses a PEBL comprising the amino acid sequence of SEQ ID NO:4. In certain embodiments, the engineered immune cell is an engineered T cell, an engineered γδ T cell, a PBMC-derived T cell, an engineered natural killer (NK) cell, an engineered NK/T cell, an engineered monocyte, an engineered macrophage, or an engineered dendritic cell.

In some embodiments, the present invention is directed to an engineered immune cell expressing a CAR that binds CD2 includes those outlined herein. In some embodiments, the engineered cell expresses a CAR comprising the amino acid sequence having at least 90% (e.g., 90%, 91%, 92%, 93%, 94%, 95%, 96%, 97%, 98%, 99%, or more) identity of SEQ ID NO:5. In certain embodiments, the engineered cell expresses a CAR comprising the amino acid sequence of SEQ ID NO:5. In certain embodiments, the engineered immune cell is an engineered T cell, an engineered γδ T cell, a PBMC-derived T cell, an engineered natural killer (NK) cell, an engineered NK/T cell, an engineered monocyte, an engineered macrophage, or an engineered dendritic cell.

In some embodiments, the present invention is directed to an engineered immune cell expressing a CAR that binds CD2 and a PEBL that binds CD2, including those outlined herein. In some embodiments, the engineered immune cell expresses a PEBL comprising an amino acid sequence having at least 90% (e.g., 90%, 91%, 92%, 93%, 94%, 95%, 96%, 97%, 98%, 99%, or more) identity to any one of SEQ ID NOS: 1-4 in addition to a CAR comprising the amino acid sequence having at least 90% (e.g., 90%, 91%, 92%, 93%, 94%, 95%, 96%, 97%, 98%, 99%, or more) identity to SEQ ID NO:5. In certain embodiments, the engineered immune cell expresses a PEBL comprising an amino acid sequence selected from the group consisting of any one of SEQ ID NOS: 1-4 in addition to a CAR comprising the amino acid sequence of SEQ ID NO:5.

In some instances, the engineered immune cell expresses a PEBL having at least 90% identity to the amino acid sequence of SEQ ID NO: 1 and a CAR having at least 90% identity to the amino acid sequence of SEQ ID NO:5. In some instances, the engineered immune cell expresses a PEBL having at least 90% identity to the amino acid sequence of SEQ ID NO:2 and a CAR having at least 90% identity to the amino acid sequence of SEQ ID NO:5. In some instances, the engineered immune cell expresses a PEBL having at least 90% identity to the amino acid sequence of SEQ ID NO:3 and a CAR having at least 90% identity to the amino acid sequence of SEQ ID NO:5. In some instances, the engineered immune cell expresses a PEBL having at least 90% identity to the amino acid sequence of SEQ ID NO:4 and a CAR having at least 90% identity to the amino acid sequence of SEQ ID NO:5. In some embodiments, the engineered immune cell expresses a PEBL of SEQ ID NO: 1 and a CAR of SEQ ID NO:5. In some embodiments, the engineered immune cell expresses a PEBL of SEQ ID NO: 1 and a CAR of SEQ ID NO:5. In some embodiments, the engineered immune cell expresses a PEBL of SEQ ID NO:2 and a CAR of SEQ ID NO:5. In some embodiments, the engineered immune cell expresses a PEBL of SEQ ID NO:3 and a CAR of SEQ ID NO:5. In some embodiments, the engineered immune cell expresses a PEBL of SEQ ID NO:4 and a CAR of SEQ ID NO:5. In certain embodiments, the engineered immune cell is an engineered T cell, an engineered γδ T cell, a PBMC-derived T cell, an engineered natural killer (NK) cell, an engineered NK/T cell, an engineered monocyte, an engineered macrophage, or an engineered dendritic cell.

PEBLs outlined herein prevent transport of target proteins to a cellular membrane. For instance, PEBLs directed to CD2 described above are retained intracellularly, such as in the ER. PEBLs directed to CD2 can co-localize intracellularly with CD2. Thus, CD2 expression on the cell surface is suppressed. In some embodiments, such PEBLs abrogate surface expression of CD2. In some instances, the PEBLs do not cause immunophenotypic changes in the engineered immune cell. Also, the PEBLs do not affect or decrease proliferation of the engineered immune cell. In some embodiments, the PEBLs are co-expressed with a CAR, such as an anti-CD2-4-1BB-CD3ζ CAR. In some instances, the expression or presence of the CD2 binding PEBL in an immune cell expressing a CD2 CAR prevents fratricide of such a cell by other CD2 CAR-T cells.

In certain embodiments, provided is an engineered immune cell comprising: a nucleic acid comprising a nucleotide sequence encoding a target-binding molecule linked to a localizing domain (e.g., PEBL), wherein the target-binding molecule is an antibody that binds CD2, and the localizing domain comprises a retention signal domain comprising an amino acid sequence selected from the group consisting of an endoplasmic reticulum (ER) sequence, a Golgi retention sequence, and a proteosome localizing sequence. In some cases, the PEBL also includes a transmembrane domain sequence derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B.

In some instances, the engineered cell comprises a nucleic acid comprising a nucleotide sequence encoding a chimeric antigen receptor (CAR). In certain cases, the CAR comprises intracellular signaling domains of 4-1BB and CD3ζ, and an antibody that binds CD2. In certain embodiments, the antibody that binds CD2 in the context of the target-binding molecule comprises: a VH sequence and a VL sequence set forth in Table 1.

In some embodiments, the engineered immune cell is an engineered T cell, an engineered natural killer (NK) cell, an engineered NK/T cell, an engineered monocyte, an engineered macrophage, or an engineered dendritic cell. In some cases, the engineered immune cell is an allogeneic cell. In other cases, the engineered immune cell is an autologous cell.

In some embodiments, the engineered immune cell lacks CD2 surface expression for at least 6 months. In other embodiments, the engineered immune cell lacks CD2 surface expression for at least 12 months. In particular embodiments, the engineered immune cell lacks CD2 surface expression for at least 20 months. In some embodiments, the engineered immune cell lacks CD2 surface expression for at least 24 months.

In some embodiments, the engineered immune cell has significantly reduced CD2 surface expression for at least 6 months compared to an immune cell that does not generate a CD2 PEBL. In other embodiments, the engineered immune cell has reduced CD2 surface expression for at least 12 months. In particular embodiments, the engineered immune cell has reduced CD2 surface expression for at least 20 months. In some embodiments, the engineered immune cell has reduced CD2 surface expression for at least 24 months.

In certain embodiments, the engineered immune cell proliferates at a substantially equal rate compared to a comparable immune cell. In some embodiments, the engineered immune cell expressing a CAR and the anti-CD2 PEBL proliferates similar to an immune cell expressing the corresponding CAR.

In some embodiments, the engineered immune cells of the present invention have enhanced therapeutic efficacy. Such engineered immune cell can be used to treat a cancer in a subject. In certain embodiments, the cancer is a CD2 associated cancer or a T cell malignancy, e.g., T cell leukemia or T cell lymphoma, such a T-cell acute lymphoblastic leukemia (T-ALL), T-cell prolymphocytic leukemia, T-cell large granular lymphocytic leukemia, enteropathy-associated T-cell lymphoma, hepatosplenic T-cell lymphoma, subcutaneous panniculitis-like T-cell lymphoma, cutaneous T-cell lymphomas (CTCL) and subtypes thereof, mycosis fungoides, Sezary syndrome, primary cutaneous gamma-delta T-cell lymphoma, malignancies with the T lineage subsets of Non-Hodgkin's lymphoma (NHL), including but not limited to, peripheral T-cell lymphoma (PTCL) not otherwise specified (PTCL-NOS) and angioimmunoblastic T-cell lymphoma, and anaplastic large cell lymphoma. In certain embodiments, the T cell malignancy is early T-cell progenitor acute lymphoblastic leukemia (ETP-ALL).

In some embodiments, the engineered immune cells of the present invention expressing a CAR and an anti-CD2 PEBL has an enhanced or increased therapeutic effect compared to an immune cell expressing the corresponding CAR. In some embodiments, the engineered immune cells expressing a CAR and an anti-CD2 PEBL have a comparable therapeutic effect as an immune cell expressing the corresponding CAR.

In another embodiment, the present invention relates to a method for producing an engineered immune cell of the present invention, comprising introducing into an immune cell a nucleic acid comprising a nucleotide sequence encoding a chimeric antigen receptor, and a nucleic acid comprising a nucleotide sequence encoding a target-binding molecule linked to a localizing domain (e.g., a PEBL molecule), thereby producing an engineered immune cell.

In certain embodiments, the engineered immune cell is an engineered T cell, an engineered natural killer (NK) cell, an engineered NK/T cell, an engineered monocyte, an engineered macrophage, or an engineered dendritic cell. In some embodiments, the engineered T cell is any type of T cell. In certain embodiments, the engineered T cell is a gamma-delta (γδ) T cell. In certain embodiments, the engineered T cell is produced from a PBMC-derived T cell.

In certain embodiments, the nucleic acid comprising a nucleotide sequence is introduced into an immune cell ex vivo. In other embodiments, the nucleic acid comprising a nucleotide sequence is introduced into an immune cell in vivo.

The nucleic acid comprising a nucleotide sequence to be introduced can be a single bicistronic construct containing a chimeric antigen receptor described herein and a target-binding molecule (e.g., scFv) linked to a localizing domain. As described herein, a single bicistronic construct can be prepared by inserting an internal ribosomal entry site (IRES) or a 2A peptide-coding region site between the 2 cDNAs encoding the chimeric antigen receptor as described herein (e.g., CAR) and the target-binding molecule (e.g., scFv). The design of tricistronic delivery systems to delete more than one target should also be feasible. Alternatively, separate transductions (simultaneously or sequentially) of the individual constructs (e.g., CAR and PEBL) could be performed. Methods of introducing exogenous nucleic acids are exemplified herein, and are well-known in the art.

In some embodiments, the nucleotide sequence encoding a CAR and the nucleotide sequence encoding a PEBL are introduced sequentially. In other embodiments, the nucleotide sequence encoding a CAR and the nucleotide sequence encoding a PEBL are introduced simultaneously. In certain cases, the nucleotide sequence encoding a CAR and the nucleotide sequence encoding a PEBL are operatively linked, and thus can be introduced on a single expression vector or plasmid.

In some embodiments, the immune cells are cultured in the presence of one or more cytokines including, but not limited to, IL-2, IL-7, IL-15, and any combination thereof. In some cases, the immune cells are cultured in the presence of an agent capable of enhancing or inducing proliferation of T cells, CD4+ T cells and/or CD8+ T cell. In some cases, the immune cells are cultured in the presence of an agent that binds a molecule of the TCR/CD3 complex and/or an agent that binds CD28. In certain embodiments, the method of culturing the engineered immune cell includes culturing in the presence of a molecule selected from the group consisting of CD90 (Thy-1), CD95 (Apo-/Fas), CD137 (4-1BB), CD154 (CD40L), ICOS, LAT, CD27, OX40 and HVEM. In certain embodiments, the method of culturing includes culturing in the presence of an agent that binds to CD90 (Thy-1), CD95 (Apo-/Fas), CD137 (4-1BB), CD154 (CD40L), ICOS, LAT, CD27, OX40, or HVEM. Additional method for culturing the engineered immune cells described herein can be found in, e.g., US20190136186, US20190062706, and US20170037369.

In some embodiments, peripheral blood mononuclear cells (PBMCs) are obtained. In some embodiments, peripheral blood mononuclear cells (PBMCs) are harvested from a human subject. In some embodiments, peripheral blood mononuclear cells (PBMCs) are harvested from a healthy human subject. In some embodiments, peripheral blood mononuclear cells (PBMCs) are harvested from a human subject with a cancer, including any described herein. In some embodiments, positive selection of T cells is performed with either (a) CD3 microbeads, or (b) both CD4 and CD8 microbeads, in accordance with the manufacturer's recommendations. In some cases, cells are resuspended at $1\times10^7$ cells per 80 µl of MACS buffer, comprising sterile filtered PBS+0.5% BSA+2 mM EDTA, and labelled with 20 µl of microbeads per 80 µl of cell suspension. Cells are incubated at 4° C. for 15 minutes, and then washed with MACS buffer. Labelled cells are passed through a LS column (Miltenyi Biotec), and positively selected T cells bound to the LS column are eluted into a collection tube. Isolated T cells are washed, and resuspended in TexMACS medium supplemented with 3% human AB serum (Sigma) at a density of $1\times10^6$ cells per ml. In some embodiments, T cells are activated with 10 µl T Cell TransAct (Miltenyi Biotec) per $1\times10^6$ T cells, and cultured with either (a) 120 IU/ml recombinant human IL-2, or (b) 12.5 ng/ml recombinant human IL-7 and 12.5 ng/ml recombinant human IL-15.

In some embodiments, one day after selection and activation (Day 1), T cells are transduced with lentivirus comprising a polynucleotide encoding a PEBL described herein and/or a polynucleotide encoding a CAR described herein at MOI for 1-10 (e.g., MOI 1, MOI 2, MOI 3, MOI 4, MOI 5, MOI 6, MOI 7, MOI 8, MOI 9, and MOI 10) using static transduction. In some cases, the T cell cultures are monitored and maintained at a cell density of $0.5-2\times10^6$ T cells per ml of culture media. Fresh IL-2, or IL-7 and IL-15 cytokines can be added to the cultures every 3-4 days. In some embodiments, ten days post transduction (Day 11), expanded T cells are harvested. In some cases the expanded T cells are analysed using functional assays and phenotypic analysis by flow cytometry.

In various aspects, also provided is a kit for producing an engineered immune cell described herein. The present kit can be used to produce, e.g., allogeneic or autologous effector T cells.

Accordingly, provided herein is a kit comprising a nucleic acid comprising a nucleotide sequence encoding PEBL such as an anti-CD2 PEBL. In some embodiments, the kit comprising a nucleic acid comprising a nucleotide sequence encoding a PEBL such as an anti-CD2 PEBL, and a nucleic acid comprising a nucleotide sequence encoding a CAR. The kit can be designed according to any of the embodiments described herein.

In certain embodiments, the nucleotide sequence encoding the CAR and/or the nucleotide sequence encoding the PEBL further comprise sequences (e.g., plasmid or vector sequences) that allow, e.g., cloning and/or expression. For example, the nucleotide sequence can be provided as part of a plasmid for ease of cloning into other plasmids and/or expression vectors for, e.g., transfection into a cell (e.g., an immune cell). In certain embodiments, the nucleotide sequence encoding the CAR and the nucleotide sequence encoding the PEBL are provided on a single plasmid or vector. In certain embodiments, the nucleotide sequences are provided on separate plasmids or expression vectors. In some embodiments, the expression vector is selected for viral expression.

Typically, the kits are compartmentalized for ease of use and can include one or more containers with reagents. In certain embodiments, all of the kit components are packaged together. Alternatively, one or more individual components of the kit can be provided in a separate package from the other kits components. The kits can also include instructions for using the kit components.

VI. Method of Treating

In one aspect, the present invention relates to the use of an engineered immune cell that comprises a nucleic acid comprising a nucleotide sequence encoding a chimeric antigen receptor (CAR) and a nucleic acid comprising a nucleotide sequence encoding a single-chain variable fragment (scFv) linked to a localizing domain for treating cancer, comprising administering a therapeutic amount of the engineered immune cell to a subject in need thereof.

In other aspects, the present invention relates to the use of an engineered immune cell that comprises a nucleic acid comprising a nucleotide sequence encoding a chimeric antigen receptor (CAR), and a nucleic acid comprising a nucleotide sequence encoding a target-binding molecule (e.g., scFv) linked to a localizing domain for treating an autoimmune disorder, comprising administering a therapeutic amount of the engineered immune cell to a subject in need thereof.

In other aspects, the present invention also relates to the use of an engineered immune cell that comprises a nucleic acid comprising a nucleotide sequence encoding a chimeric antigen receptor (CAR), and a nucleic acid comprising a nucleotide sequence encoding a target-binding molecule against CD2 (e.g., anti-CD2 scFv) linked to a localizing domain for treating an infectious disease, comprising administering a therapeutic amount of the engineered immune cell to a subject in need thereof.

In some aspects, the engineered immune cell is administered by infusion into the subject. Methods of infusing immune cells (e.g., allogeneic or autologous immune cells) are known in the art. A sufficient number of cells are administered to the recipient in order to ameliorate the symptoms of the disease. Typically, dosages of $10^7$ to $10^{10}$ cells are infused in a single setting, e.g., dosages of $10^9$ cells. Infusions are administered either as a single $10^9$ cell dose or divided into several $10^9$ cell dosages. The frequency of infusions can be every 3 to 30 days or even longer intervals if desired or indicated. The quantity of infusions is generally at least 1 infusion per subject and preferably at least 3 infusions, as tolerated, or until the disease symptoms have been ameliorated. The cells can be infused intravenously at a rate of 50-250 ml/hr. Other suitable modes of administration include intra-arterial infusion, direct injection into tumor and/or perfusion of tumor bed after surgery, implantation at the tumor site in an artificial scaffold, intrathecal administration, and intraocular administration. Methods of adapting the present invention to such modes of delivery are readily available to one skilled in the art.

In some aspects, provided is a substantially pure population of engineered immune cells comprising any one of the engineered immune cells described herein, wherein at least 90%, e.g., at least 90%, 91%, 92%, 93%, 94%, 95, 96%, 97%, 98%, 99% or more of the engineered immune cells lack CD2 expression. In some cases, the substantially pure population comprises at least 80%, e.g., at least 80%, 81%, 82%, 83%, 84%, 85%, 86%, 87%, 88%, 89%, 90%, 91%, 92%, 93%, 94%, 95%, 96%, 97%, 98%, 99%, or more engineered immune cells lacking CD2 expression.

In other aspects, also provided is a method of treating cancer or an autoimmune disorder in a subject in need thereof, comprising administering a therapeutic amount of an engineered immune cell having any of the embodiments described herein to the subject, thereby treating cancer or an autoimmune disorder in a subject in need thereof. In some aspects, provided is a method of treating cancer or an autoimmune disorder in a subject in need thereof, comprising administering a therapeutic amount of a substantially pure population of engineered immune cells having any of the embodiments described herein to the subject, thereby treating cancer or an autoimmune disorder in a subject in need thereof.

In certain embodiments, the method comprises administering a therapeutic amount of an engineered immune cell comprising a nucleic acid having a nucleotide sequence encoding a target-binding molecule against CD2 linked to a localizing domain, as described herein. In some instances, a second nucleic acid comprises a nucleotide sequence encoding a CAR. In some embodiments, the CAR comprises intracellular signaling domains of 4-1BB and CD35, and an antibody that binds to a cytokine such as CD2.

In some embodiments, the engineered immune cell is autologous to the subject in need of treatment. In other embodiments, the engineered immune cell is allogenic to the subject in need of treatment.

In certain embodiments, the engineered immune cell is administered into the subject by intravenous infusion, intra-arterial infusion, direct injection into tumor and/or perfusion of tumor bed after surgery, implantation at a tumor site in an artificial scaffold, intrathecal administration, and intraocular administration.

In certain embodiments, the engineered immune cell is administered by infusion into the subject. Methods of infusing immune cells (e.g., allogeneic or autologous immune cells) are known in the art. A sufficient number of cells are administered to the recipient in order to ameliorate the symptoms of the disease. Typically, dosages of $10^7$ to $10^{10}$ cells are infused in a single setting, e.g., dosages of $10^9$ cells. Infusions are administered either as a single $10^9$ cell dose or divided into several $10^9$ cell dosages. The frequency of infusions can be daily, every 2 to 30 days or even longer intervals if desired or indicated. The quantity of infusions is generally at least 1 infusion per subject and preferably at least 3 infusions, as tolerated, or until the disease symptoms have been ameliorated. The cells can be infused intravenously at a rate of 50-250 ml/hr. Other suitable modes of administration include intra-arterial infusion, intraperitoneal infusion, direct injection into tumor and/or perfusion of tumor bed after surgery, implantation at the tumor site in an artificial scaffold, intrathecal administration. Methods of adapting the present invention to such modes of delivery are readily available to one skilled in the art.

In certain embodiments, the method of treating cancer according to the present invention is combined with at least one other known cancer therapy, e.g., chemotherapy. In some embodiments, the method of treating cancer according to the present invention is combined therapeutically an agent that suppresses negative checkpoint regulators such an antibody to PD-1, CTLA4, LAG3, TIM3, TIGIT, or another immune checkpoint molecule. This combination may be particularly effective when treating T cell lymphomas, due to immune suppressive environment often present within lymphomas.

In other aspects, also provided is use of an engineered immune cell having any of the embodiments described herein for treating cancer, comprising administering a therapeutic amount (therapeutic population) of the engineered immune cells to a subject in need thereof. In certain embodiments, the engineered immune cell is administered into the subject by intravenous infusion, intra-arterial infusion, intraperitoneal infusion, direct injection into tumor and/or perfusion of tumor bed after surgery, implantation at a tumor site in an artificial scaffold, intrathecal administration.

In some embodiments, the subject is treated with a non-myeloablative chemotherapy prior to an administration (e.g., an infusion) of engineered immune cells outlined herein. In some embodiments, the non-myeloablative chemotherapy is cyclophosphamide 60 mg/kg/d for 2 days (days 27 and 26 prior to infusion of the engineered immune cells) and fludarabine 25 mg/m$^2$/d for 5 days (days 27 to 23 infusion of the engineered immune cells). The subject is administered one or more lymphodepletion (e.g., immunosuppressive conditioning) agents. Non-limiting examples of a preconditioning agent include cyclophosphamide, fludarabine, and any combinations thereof. Detailed methods for conditioning a patient prior to CAR-T cell therapy are found in, for example, U.S. Pat. No. 9,855,298, the contents are incorporated by reference herein in its entireties.

Additional preconditioning methods are described in Gassner et al., Cancer Immunol. Immunother. 2011, 60, 75-85, Muranski et al., Nat. Clin. Pract. Oncol., 2006, 3, 668-681, Dudley, et al., J. Clin. Oncol. 2008, 26, 5233-5239, and Dudley et al., J. Clin. Oncol. 2005, 23, 2346-2357, all of which are incorporated by reference herein in their entireties.

In some embodiments, after receiving non-myeloablative chemotherapy and infusion of the engineered immune cells, the subject receives an intravenous administration of a cytokine, such as IL-2, IL-7, IL-15, or any combination thereof. In some embodiments, after receiving non-myeloablative chemotherapy the patient receives a population of the engineered immune cells in combination with IL-2, IL-7, IL-15, or any combination thereof. In some cases, IL-2, IL-7, IL-15, or any combination thereof are administered after the population of cells. In certain cases, IL-2, IL-7, IL-15, or any combination thereof are administered concomitantly with the population of cells. IL-2 includes IL-2 (aldeskeukin), a biosimilar thereof, or a variant thereof.

In some embodiments, the IL-2 comprises a high-dose IL-2 regimen such as but not limited to, administering intravenously starting on the day after administering a therapeutically effective population of engineered immune cells described herein, wherein the IL-2 is administered at a dose of 0.037 mg/kg or 0.044 mg/kg IU/kg (patient body mass) using 15-minute bolus intravenous infusions every eight hours until tolerance, for a maximum of 14 doses. Following 9 days of rest, the schedule may be repeated for another 14 doses, for a maximum of 28 doses in total.

In other embodiments, IL-2 is administered intravenously at a dose of about $18 \times 10^6$ IU/m$^2$ over 6 hours, followed by a dose of $18 \times 10^6$ IU/m$^2$ over 12 hours, followed by a dose of $18 \times 10^6$ IU/m$^2$ over 24 hours, and followed by a dose of $18 \times 10^6$ IU/m$^2$ over 72 hours. Such a treatment regimen can be repeated every 28 days for a maximum of four cycles. In some embodiments, the IL-2 regimen comprises 18,000,000 IU/m$^2$ on day 1, and 9,000,000 IU/m$^2$ on day 2, and 4,500,000 IU/m$^2$ on days 3 and 4. In another embodiment, the IL-2 regimen comprises administration of pegylated IL-2 every 1, 2, 4, 6, 7, 14 or 21 days at a dose of 0.10 mg/day to 50 mg/day.

In some embodiments, the engineered immune cells or the population of the engineered immune cells are administered as part of a combination treatment, such as simultaneously with or sequentially with, in any order, another therapeutic intervention, such as an antibody or engineered cell or receptor or agent, such as a cytotoxic or therapeutic agent. In some embodiments, the cells are co-administered with one or more additional therapeutic agents or in connection with another therapeutic intervention, either simultaneously or sequentially in any order. In some embodiments, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent. In some embodiments, the therapeutic agent suppresses negative checkpoint regulators, such as but not limited to an antibody to PD-1, CTLA4, LAG3, TIM3, TIGIT, or another immune checkpoint molecule.

Following administration of the engineered immune cells described herein, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285 (1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in cancer burden or load.

VII. Exemplary Embodiments of the Invention

In one aspect, the invention provides a polynucleotide encoding an anti-CD2-4-1BB-CD3ζ chimeric antigen receptor (CAR) comprising an anti-CD2 single chain variable fragment (scFv) domain, a CD8α hinge-transmembrane domain, a 4-1BB intracellular signaling domain, and a CD3ζ signaling domain.

Of the polynucleotide of any embodiment, said anti-CD2 scFv domain of the CAR comprises an amino acid sequence having at least 90% (e.g., 90%, 91%, 92%, 93%, 94%, 95%, 96%, 97%, 98%, 99%, or 100%) sequence identity of SEQ ID NO:22 or SEQ ID NO:23. Of the polynucleotide of any embodiment, said CD8α hinge-transmembrane domain of the CAR comprises an amino acid sequence having at least 90% sequence identity of SEQ ID NO:15. Of the polynucleotide of any embodiment, said 4-1BB intracellular signaling domain of the CAR comprises an amino acid sequence having at least 90% (e.g., 90%, 91%, 92%, 93%, 94%, 95%, 96%, 97%, 98%, 99%, or 100%) sequence identity of SEQ ID NO:16. Of the polynucleotide of any embodiment, said CD33 signaling domain of the CAR comprises an amino acid sequence having at least 90% (e.g., 90%, 91%, 92%, 93%, 94%, 95%, 96%, 97%, 98%, 99%, or 100%) sequence identity of SEQ ID NO:17. Of the polynucleotide of any embodiment, the CAR comprises an amino acid sequence having at least 90% (e.g., 90%, 91%, 92%, 93%, 94%, 95%, 96%, 97%, 98%, 99%, or 100%) sequence identity to SEQ ID NO:5. In some cases, the CAR has a nucleic acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to any one of SEQ ID NO: 10.

Provided herein is an isolated viral vector comprising any one of the polynucleotides encoding the CAR described herein. In some aspects of the invention, the isolated viral vector comprising any one of the polynucleotides encoding the CAR outlined herein is introduced into an immune cell.

Also provided herein is an engineered immune cell comprising the anti-CD2-4-1BB-CD3ζ chimeric antigen receptor described herein. The engineered immune cell of any embodiment is an engineered allogeneic cell. The engineered immune cell of any embodiment is an engineered autologous cell. The engineered immune cell of any embodiment is an engineered T cell. The engineered immune cell of any embodiment is an engineered gamma-delta T cell receptor bearing T cell. The engineered immune cell of any embodiment is an engineered NK cell. The engineered immune cell of any embodiment is an engineered gamma-delta T cell receptor bearing T cell.

Provided herein an isolated viral vector comprising a polynucleotide encoding a CD2 blocking polypeptide comprising a single chain variable fragment (scFv) that binds CD2 linked to the N-terminus of a cellular localizing domain, wherein cellular localizing domain comprises an amino acid sequence selected from the group consisting of an endoplasmic reticulum (ER) retention sequence, a Golgi retention sequence, and a proteosome localizing sequence, and wherein said CD2 blocking polypeptide binds endogenous CD2 within a cell.

Of the isolated viral vector of any one of the embodiments, said scFv comprises: (i) a variable heavy chain (VH) sequence having at least 90% sequence identity to SEQ ID NO:18 and a variable light chain (VL) sequence having at least 90% sequence identity to SEQ ID NO:19, or (ii) variable heavy chain (VH) sequence having at least 90% sequence identity to SEQ ID NO:20 and a variable light chain (VL) sequence having at least 90% sequence identity to SEQ ID NO:21.

Of the isolated viral vector of any one of the embodiments, said ER retention sequence comprises an amino acid sequence selected from the group consisting of KDEL, KKXX, KKMP, and KKTN, wherein X can be any amino acid; or said Golgi retention sequence is selected from the group consisting of YGRL (SEQ ID NO:40), YQRL (SEQ ID NO:41), YKGL (SEQ ID NO:42), and YXXL (SEQ ID NO:43), wherein X can be any amino acid. Of the isolated viral vector of any one of the embodiments, said CD2 blocking polypeptide further comprises a transmembrane domain linked between said scFv and said ER retention sequence domain comprising KKMP or KKTN or said Golgi retention sequence domain comprising YGRL, YQRL, YKGL, wherein said transmembrane domain is a transmembrane domain selected from any one of CD8 α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, and FGFR2B. Of the isolated viral vector of any one of the embodiments, said transmembrane domain comprises a hinge-transmembrane domain of CD8α.

Of the isolated viral vector of any one of the embodiments, said CD2 blocking polypeptide comprises an amino acid sequence having at least 90% sequence identity to any one selected from the group consisting of SEQ ID NOS: 1-4. In some embodiments, the CD2 blocking polypeptide comprises a nucleic acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to any one of SEQ ID NOs:6-9.

In some aspects of the invention, the isolated viral vector comprising a polynucleotide encoding any of CD2 blocking polypeptides outlined herein is introduced into an immune cell.

Also provided herein is an engineered immune cell comprising the CD2 blocking polypeptides described herein. The engineered immune cell of any embodiment is an engineered allogeneic cell. The engineered immune cell of any embodiment is an engineered autologous cell. The engineered immune cell of any embodiment is an engineered T cell. The engineered immune cell of any embodiment is an engineered NK cell.

In one aspect, provided herein is an engineered immune cell comprising a polypeptide comprising a target-binding molecule linked to a cellular localizing domain, wherein the target-binding molecule is an antibody that binds CD2 protein (e.g., human CD2 protein), the cellular localizing domain comprises an amino acid sequence selected from the group consisting of an endoplasmic reticulum (ER) retention sequence, a Golgi retention sequence, and a proteosome localizing sequence, and the target-binding molecule linked to the localizing domain is not secreted by the engineered cell.

In some embodiments, the antibody that binds the CD2 protein (e.g., human CD2 protein) is an anti-CD2 single chain variable fragment (scFv). In some embodiments, the scFv comprises a variable heavy chain ($V_H$) sequence having at least 90% sequence identity to SEQ ID NO:18 and a variable light chain ($V_L$) sequence having at least 90% sequence identity to SEQ ID NO:19. In some embodiments, the scFv comprises a variable heavy chain ($V_H$) sequence set forth in SEQ ID NO: 18 and a variable light chain ($V_L$) sequence set forth in SEQ ID NO:19.

In some embodiments, the scFv comprises a variable heavy chain ($V_H$) sequence having at least 90% sequence identity to SEQ ID NO:20 and a variable light chain ($V_L$) sequence having at least 90% sequence identity to SEQ ID NO:21. In certain embodiments, the scFv comprises a variable heavy chain ($V_H$) sequence set forth in SEQ ID NO:20 and a variable light chain ($V_L$) sequence set forth in SEQ ID NO:21

In some embodiments, the cellular localizing domain comprises an amino acid sequence selected from KDEL, KKXX, KKMP, or KKTN, wherein X can be any amino acid. In certain embodiments, the polypeptide further comprises a transmembrane domain linked between the target-binding molecule and the cellular localizing domain. In some case, the transmembrane domain is derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B.

In certain embodiments, the transmembrane domain comprises a hinge-transmembrane domain derived from CD8α.

In various embodiments, the polypeptide of the engineered immune cell comprises an amino acid sequence having at least 90% (e.g., 90%, 91%, 92%, 93%, 94%, 95%, 96%, 97%, 98%, 99%, or 100%) sequence identity to SEQ ID NO: 1 or SEQ ID NO:3. The polypeptide may comprise an amino acid sequence of SEQ ID NO: 1 or SEQ ID NO:3.

In certain embodiments, the polypeptide of the engineered immune cell comprises an amino acid sequence having at least 90% sequence identity to SEQ ID NO:2 or SEQ ID NO:4. The polypeptide may comprise an amino acid sequence of SEQ ID NO:2 or SEQ ID NO:4.

In some embodiments, the engineered immune cell further comprises a chimeric antigen receptor (CAR). In certain instances, the CAR is an anti-CD2-4-1BB-CD3ζ CAR. The anti-CD2-4-1BB-CD3ζ CAR may comprise an amino acid sequence having at least 90% (e.g., 90%, 91%, 92%, 93%, 94%, 95%, 96%, 97%, 98%, 99%, or 100%) sequence identity to SEQ ID NO:5. The anti-CD2-4-1BB-CD3ζ CAR can bind CD2 (e.g., human CD2). In some instances, such an anti-CD2-4-1BB-CD3ζ CAR can be referred to as a "CD2 CAR".

In some embodiments, the engineered immune cell induces cytotoxicity of CD2+ cells.

In some embodiments, endogenous CD2 expression is blocked in the engineered immune cell. The blockage of endogenous CD2 expression may persist for at least 6 months. The blockage of endogenous CD2 expression may persist for at least 12 months. In some embodiments, the engineered immune cell proliferates at a substantially equivalent rate as a comparable immune cell.

In II some embodiments, the engineered immune cell is an engineered allogeneic cell or an engineered autologous cell. In other embodiments, the engineered immune cell is an engineered T cell such as a gamma-delta T cell.

In another aspect, provided herein is a method of treating cancer or an autoimmune disease in a subject in need thereof comprising administering a therapeutic amount of a composition comprising any one of the engineered immune cell described herein to the subject, thereby treating cancer or the autoimmune disease in a subject in need thereof. In some instances, the composition further comprises a pharmaceutically acceptable carrier. The cancer may be a T cell malignancy or a CD2 associated cancer. In one embodiment, the T cell malignancy is early T cell progenitor acute lymphoblastic leukemia (ETP-ALL) or another T cell leukemia. In another embodiment the T cell malignancy is a lymphoma, including but not limited to, Cutaneous T-Cell Lymphoma (CTCL), Mycosis Fungoides, Sezary Syndrome or Peripheral T cell Lymphoma (PTCL).

In some embodiments, the administration is by intravenous infusion, intra-arterial infusion, intraperitoneal infusion, direct injection into tumor and/or perfusion of tumor bed after surgery, implantation at a tumor site in an artificial scaffold, or intrathecal administration.

In another aspect, provided herein is a polynucleotide encoding a polypeptide comprising a target-binding molecule linked to a cellular localizing domain. In some cases, the target-binding molecule is an antibody that binds CD2 protein (e.g., human CD2 protein), the cellular localizing domain comprises an amino acid sequence selected from the group consisting of an endoplasmic reticulum (ER) retention sequence, a Golgi retention sequence, and a proteosome localizing sequence, and the target-binding molecule linked to the localizing domain is not secreted by the engineered cell.

In particular embodiments, the antibody that binds the CD2 protein (e.g., human CD2 protein) is an anti-CD2 single chain variable fragment (scFv). In certain embodiments, the scFv comprises a variable heavy chain ($V_H$) sequence having at least 90% (e.g., 90%, 91%, 92%, 93%, 94%, 95%, 96%, 97%, 98%, 99%, or 100%) sequence identity to SEQ ID NO:18 and a variable light chain ($V_L$) sequence having at least 90% (e.g., 90%, 91%, 92%, 93%, 94%, 95%, 96%, 97%, 98%, 99%, or 100%) sequence identity to SEQ ID NO:19. In some embodiments, the scFv comprises a variable heavy chain ($V_H$) sequence set forth in SEQ ID NO:18 and a variable light chain ($V_L$) sequence set forth in SEQ ID NO:19.

In other embodiments, the scFv comprises a variable heavy chain ($V_H$) sequence having at least 90% sequence identity to SEQ ID NO:20 and a variable light chain ($V_L$) sequence having at least 90% sequence identity to SEQ ID NO:21. In certain embodiments, the scFv comprises a variable heavy chain ($V_H$) sequence set forth in SEQ ID NO:20 and a variable light chain ($V_L$) sequence set forth in SEQ ID NO:21.

In some embodiments, the cellular localizing domain comprises an amino acid sequence selected from KDEL, KKXX, KKMP, or KKTN, wherein X can be any amino acid. In certain embodiments, the polypeptide further comprises a transmembrane domain linked between the target-binding molecule and the cellular localizing domain. In some cases, the transmembrane domain is derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B.

In certain embodiments, the transmembrane domain comprises a hinge-transmembrane domain derived from CD8α.

In certain embodiments, the polypeptide of the engineered immune cell comprises an amino acid sequence having at least 90% (e.g., 90%, 91%, 92%, 93%, 94%, 95%, 96%, 97%, 98%, 99%, or 100%) sequence identity to SEQ ID NO: 1 or SEQ ID NO:3. The polypeptide may comprise an amino acid sequence of SEQ ID NO: 1 or SEQ ID NO:3.

In various embodiments, the polypeptide of the engineered immune cell comprises an amino acid sequence having at least 90% (e.g., 90%, 91%, 92%, 93%, 94%, 95%, 96%, 97%, 98%, 99%, or 100%) sequence identity to SEQ ID NO:2 or SEQ ID NO:4. The polypeptide may comprise an amino acid sequence of SEQ ID NO:2 or SEQ ID NO:4.

In certain embodiments, the PEBL described herein comprises a nucleic acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to any one of SEQ ID NOs:6-9.

In some embodiments, provided herein is an expression vector comprising any one of polynucleotide described herein. In some cases, the expression vector also includes a nucleic acid sequence coding for a chimeric antigen receptor (CAR). The CAR can be an anti-CD2-4-1BB-CD3ζ CAR. In some embodiments, the anti-CD2-4-1BB-CD3ζ CAR comprises an amino acid sequence having at least 90% (e.g., 90%, 91%, 92%, 93%, 94%, 95%, 96%, 97%, 98%, 99%, or 100%) sequence identity to SEQ ID NO:5.

In some embodiments, the expression vector comprises a nucleic acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to any one of SEQ ID NO:10. In some cases, the expression vector comprises the nucleic acid sequence of SEQ ID NO:10. In some embodiments, the expression vector comprises a nucleic acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to any one of SEQ ID NOs:6-9. In some cases, the expression vector comprises the nucleic acid sequence of any one of SEQ ID NOS:6-9.

In some embodiments, provided herein a host cell comprising any one of the expression vectors described herein.

In yet another aspect, provided herein is a method for producing an engineered immune cell, the method comprising: introducing into an immune cell any one of the polynucleotides or expression vectors disclosed herein. In some embodiments, the endogenous CD2 expression is blocked in the engineered immune cell. In some embodiments, the engineered immune cell is an engineered allogeneic cell or an engineered autologous cell. In other embodiments, the engineered immune cell is an engineered T cell such as a gamma-delta T cell.

In one aspect, provided herein is an isolated anti-CD2-4-1BB-CD3ζ chimeric antigen receptor (CAR) molecule comprising an anti-CD2 single chain variable fragment (scFv) domain, a CD8α hinge-transmembrane domain, a 4-1BB intracellular signaling domain, and a CD3ζ signaling domain. The anti-CD2 single chain variable fragment (scFv) domain can comprise an amino acid sequence having at least 90% (e.g., 90%, 91%, 92%, 93%, 94%, 95%, 96%, 97%, 98%, 99%, or 100%) sequence identity of SEQ ID NO:22 or SEQ ID NO:23. The CD8α hinge-transmembrane domain can include an amino acid sequence having at least 90% sequence identity of SEQ ID NO:15. The 4-1BB intracellular signaling domain may contain an amino acid sequence having at least 90% sequence identity of SEQ ID NO:16. The CD3ζ signaling domain may contain an amino acid sequence having at least 90% (e.g., 90%, 91%, 92%, 93%, 94%, 95%, 96%, 97%, 98%, 99%, or 100%) sequence identity of SEQ ID NO:17. In some embodiments, the isolated CAR molecule comprises an amino acid sequence having at least 90% (e.g., 90%, 91%, 92%, 93%, 94%, 95%, 96%, 97%, 98%, 99%, or 100%) sequence identity to SEQ ID NO:5. In another aspect, provided herein is an isolated nucleic acid molecule encoding any one of the isolated CAR molecules described herein. The anti-CD2-4-1BB-CD3ζ CAR can bind CD2 (e.g., human CD2).

In another aspect, provided herein is an engineered immune cell comprising a polypeptide comprising an anti-CD2-4-1BB-CD3ζ chimeric antigen receptor (CAR) comprising an anti-CD2 single chain variable fragment (scFv) domain, a CD8α hinge-transmembrane domain, a 4-1BB intracellular signaling domain, and a CD3ζ signaling domain. The anti-CD2-4-1BB-CD3ζ CAR can bind CD2 (e.g., human CD2).

In some embodiments, the anti-CD2 single chain variable fragment (scFv) domain comprises an amino acid sequence having at least 90% (e.g., 90%, 91%, 92%, 93%, 94%, 95%, 96%, 97%, 98%, 99%, or 100%) sequence identity of SEQ ID NO:22 or SEQ ID NO:23. In several embodiments, the CD8α hinge-transmembrane domain includes an amino acid sequence having at least 90% sequence identity of SEQ ID NO:15. In certain embodiments, the 4-1BB intracellular signaling domain contains an amino acid sequence having at least 90% (e.g., 90%, 91%, 92%, 93%, 94%, 95%, 96%, 97%, 98%, 99%, or 100%) sequence identity of SEQ ID NO:16. In particular embodiments, the CD3ζ signaling domain comprises an amino acid sequence having at least 90% (e.g., 90%, 91%, 92%, 93%, 94%, 95%, 96%, 97%, 98%, 99%, or 100%) sequence identity of SEQ ID NO:17. In some embodiments, the isolated CAR molecule comprises an amino acid sequence having at least 90% (e.g., 90%, 91%, 92%, 93%, 94%, 95%, 96%, 97%, 98%, 99%, or 100%) sequence identity to SEQ ID NO:5. In some embodiments, the isolated CAR molecule comprises the amino acid sequence of SEQ ID NO:5. In some embodiments, the isolated CAR molecule comprises the nucleic acid sequence of SEQ ID NO:10.

In some embodiments, the engineered immune cell is an engineered allogeneic cell or an engineered autologous cell. In other embodiments, the engineered immune cell is an engineered T cell such as a gamma-delta T cell.

The contents such as the specification, claims, and figures of WO 2016/126213 and PCT/US2017/063048 are incorporated herein by reference in its entirety for all purposes.

EXAMPLES

Example 1: Blockade of CD2 Expression in T Cells for Effective Chimeric Antigen Receptor Therapies This example illustrates blockade of CD2 expression with a novel method, combined with a second-generation CAR, resulting in potent anti-CD2 CAR-T cells. This practical strategy provides a new treatment option for patients with cancer.

FIG. 1 provides an exemplary anti-CD2 chimeric antigen receptor (CAR). The scFv of the anti-CD2 monoclonal antibody 9.6 was joined to the CD8α signal peptide, CD8α hinge-transmembrane domain, and the intracellular domains of 4-1BB and CD3ζ of the anti-CD19-4-1BB-CD3 CAR previously developed in the laboratory. The scFv of the anti-CD2 monoclonal antibody 9.6 or 9-1 was joined to the CD8α signal peptide, and a sequence encoding a localizing domain, and optionally, a CD8α hinge-transmembrane domain. These were subcloned into a murine stem cell virus (MSCV) vector. In some cases, the MSCV is a MSCV-internal ribosome entry site (IRES)-green fluorescent protein (GFP) retroviral vector containing a firefly luciferase gene.

Figure 2:
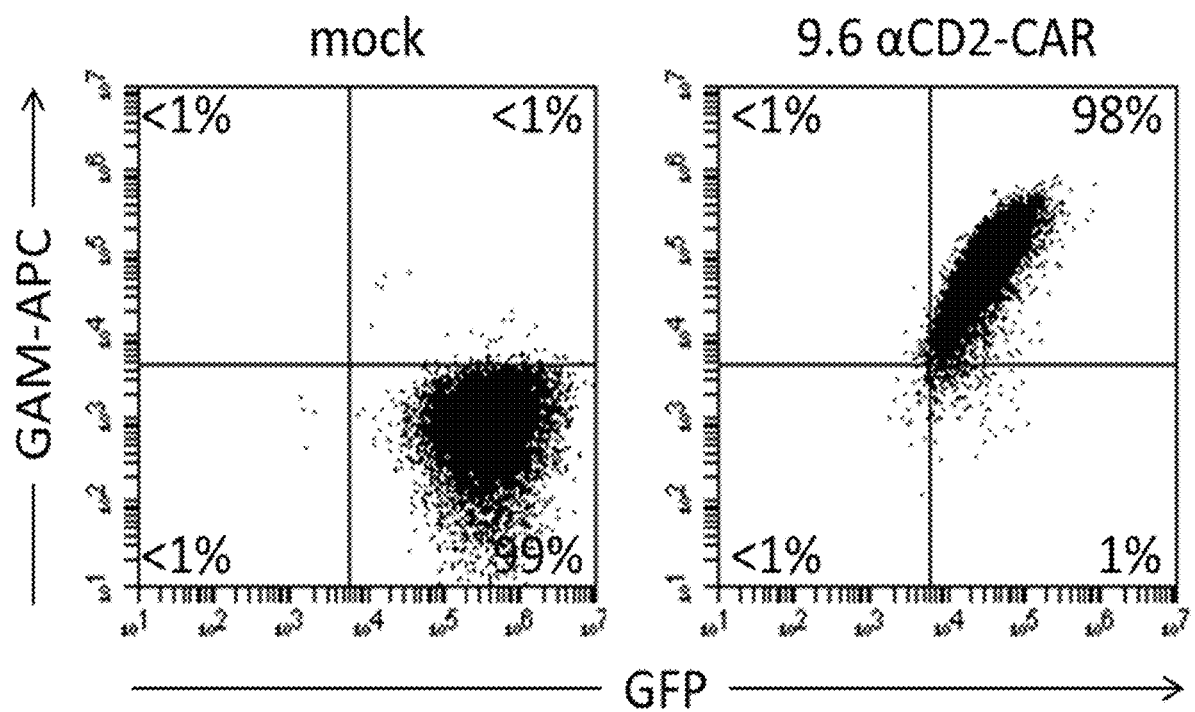
FIG. 2 illustrates expression of an anti-CD2 CAR in Jurkat cells. The anti-CD2 CAR comprise an anti-CD2 scFv based on the anti-CD2 monoclonal antibody 9.6. Detailed descriptions of 9.6 can be found, e.g., in Kamoun et al. J Exp Med, 1981, 153:207-212. Cells were transduced with vectors containing the CAR construct and GFP or GFP only ("Mock"). Flow cytometric dot plots illustrate anti-CD2 CAR expression. Anti-goat anti-mouse antibody APC (GAM-APC) was used.

The 9.6 anti-CD2 CAR retroviral vector construct was transduced into Jurkat cells (a leukemia cell line). Preparation of retroviral supernatant and transduction were performed according to standard protocols known to those skilled in the art. The expression results are shown in FIG. 2.

CCRF-CEM cells with the CD2 gene were also transduced with the 9.6 anti-CD2 CAR retroviral vector construct. The resulting cells were maintained in RPMI-1640 media supplemented with 10% FBS and 1% Pen-Strep. The activity of the 9.6 anti-CD2 was assessed. FIG. 3 shows that the anti-CD2 CAR induced expression of CD2 and CD69 (activation markers) in the presence of CD2 target cells.

To determine the effect of the anti-CD2 CAR in peripheral blood T lymphocytes, the anti-CD2 CAR was introduced into primary T cells by retroviral (e.g., lentiviral) transduction or electroporation.

FIG. 4 shows the CAR expression.

FIG. 5 shows the function of the anti-CD2 CAR when CD2+ target cells (MOLT-4) were cocultured with Jurkat cells transduced with the anti-CD2 CAR or transduced with a vector containing GFP only. In some cases, the cells were co-cultured at 1:1 E:T. The results show that the 9.6 anti-CD2 CAR-T cells exert cytotoxicity against CD2+ target cells.

FIG. 6 shows exemplary embodiments of anti-CD2 PEBL constructs. 9.6 PEBLs and 9-1 PEBLs were retrovirally transduced into Jurkat cells. The histograms of FIG. 7 show downregulation of CD2 expression.

FIG. 8 shows that the 9.6 PEBL II downregulates CD2 expression in human peripheral blood T cells.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. An engineered immune cell comprising one or more expression vectors encoding:

(i) a CD2 blocking polypeptide comprising a single chain variable fragment (scFv) linked to the N-terminus of a cellular localizing domain, wherein the scFv binds CD2, wherein the cellular localizing domain comprises an endoplasmic reticulum (ER) retention sequence, wherein said CD2 blocking polypeptide remains intracellularly within said engineered immune cell and binds endogenous CD2 within the engineered immune cell, and wherein the CD2 blocking polypeptide comprises SEQ ID NO: 4; and (ii) a chimeric antigen receptor (CAR) comprising a CD2 targeting domain, a transmembrane domain, and a signaling domain, wherein the CAR is an anti-CD2-4-1BB-CD3ζ CAR, wherein the anti-CD2-4-1BB-CD3ζ CAR comprises SEQ ID NO: 5.

2. The engineered immune cell of claim 1, wherein said engineered immune cell induces cytotoxicity of CD2+ cells.

3. The engineered immune cell of claim 1, wherein CD2 surface expression by said engineered immune cell is blocked by the CD2 blocking polypeptide.

4. The engineered immune cell of claim 1, wherein said engineered immune cell is an allogeneic cell.

5. The engineered immune cell of claim 1, wherein said engineered immune cell is an autologous cell.

6. The engineered immune cell of claim 1, wherein said engineered immune cell is selected from the group consisting of an engineered T cell, an engineered gamma-delta T cell, and an engineered NK cell.

7. A method of treating cancer in a subject in need thereof comprising administering a therapeutic amount of a composition comprising the engineered immune cell of claim 1 to the subject, thereby treating cancer in the subject in need thereof; wherein the cancer is a CD2-expressing T-cell malignancy or a CD2-expressing cancer; and wherein the engineered immune cell is autologous or allogeneic to the subject.

8. The method of claim 7, wherein said CD2-expressing T-cell malignancy or said CD2-expressing cancer is selected from the group consisting of T cell leukemia, T cell lymphoma, T-cell acute lymphoblastic leukemia (T-ALL), early T-cell progenitor acute lymphoblastic leukemia (ETP-ALL), T-cell prolymphocytic leukemia, T-cell large granular lymphocytic leukemia, enteropathy-associated T-cell lymphoma, hepatosplenic T-cell lymphoma, subcutaneous panniculitis-like T-cell lymphoma, cutaneous T-cell lymphomas (CTCL), any subtype of CTCL, mycosis fungoides, Sezary syndrome, primary cutaneous gamma-delta T-cell lymphoma, a malignancy with the T lineage subsets of Non-Hodgkin's lymphoma (NHL), peripheral T-cell lymphoma (PTCL) not otherwise specified (PTCL-NOS) and angioimmunoblastic T-cell lymphoma, and anaplastic large cell lymphoma.

9. The method of claim 7, wherein said administration is by intravenous infusion, intra-arterial infusion, intraperitoneal infusion, direct injection into tumor and/or perfusion of tumor bed after surgery, implantation at a tumor site in an artificial scaffold, or intrathecal administration.

10. A polynucleotide encoding a CD2 blocking polypeptide comprising SEQ ID NO: 4.

* * * * *